(12) United States Patent
Erikson

(10) Patent No.: US 6,613,524 B1
(45) Date of Patent: Sep. 2, 2003

(54) AMPEROMETRIC AFFINITY ASSAY AND ELECTRICALLY STIMULATED COMPLEXES OF NUCLEIC ACIDS

(75) Inventor: Glen H. Erikson, Providenciales (TC)

(73) Assignee: Ingeneus Corporation, Bridgetown (BB)

(*) Notice: Subject to any disclaimer, the term of this patent is extended or adjusted under 35 U.S.C. 154(b) by 21 days.

(21) Appl. No.: 09/998,155

(22) Filed: Nov. 29, 2001

Related U.S. Application Data

(63) Continuation-in-part of application No. 09/911,047, filed on Jul. 23, 2001, which is a continuation-in-part of application No. 09/490,273, filed on Jan. 24, 2000, now Pat. No. 6,265,170.

(51) Int. Cl.$^7$ .......................... C12Q 1/68; C12P 19/34; G01N 33/00; C07H 21/00

(52) U.S. Cl. .................. 435/6; 435/91.1; 435/91.2; 435/287.2; 536/25.3; 935/77; 935/78; 436/94

(58) Field of Search .......................... 435/6, 91.1, 91.2, 435/94; 536/25.3; 935/77, 78

(56) References Cited

U.S. PATENT DOCUMENTS

| | | |
|---|---|---|
| 4,220,450 A | 9/1980 | Maggio |
| 4,876,187 A | 10/1989 | Duck et al. |
| 4,963,477 A | 10/1990 | Tchen |
| 5,011,769 A | 4/1991 | Duck et al. |
| 5,332,659 A | 7/1994 | Kidwell |
| 5,403,711 A | 4/1995 | Walder et al. |
| 5,538,848 A | 7/1996 | Livak et al. |
| 5,539,082 A | 7/1996 | Nielsen et al. |
| 5,558,998 A | 9/1996 | Hammond et al. |
| 5,660,988 A | 8/1997 | Duck et al. |
| 5,705,346 A | 1/1998 | Okamoto et al. |
| 5,707,801 A | 1/1998 | Bresser et al. |
| 5,731,146 A | 3/1998 | Duck et al. |
| 5,783,063 A | 7/1998 | Clarkson et al. |
| 5,800,984 A | 9/1998 | Vary |
| 5,800,992 A | 9/1998 | Fodor et al. |
| 5,814,447 A | 9/1998 | Ishiguro et al. |
| 5,814,516 A | 9/1998 | Vo-Dinh |
| 5,824,477 A | 10/1998 | Stanley |
| 5,824,557 A | 10/1998 | Burke et al. |
| 5,846,729 A | 12/1998 | Wu et al. |
| 5,861,124 A | 1/1999 | Hosoi et al. |
| 5,874,555 A | 2/1999 | Dervan et al. |
| 5,888,739 A | 3/1999 | Pitner et al. |
| 5,912,332 A | 6/1999 | Agrawal et al. |
| 5,948,897 A | 9/1999 | Sen et al. |
| 6,013,442 A | 1/2000 | Kolesar et al. |
| 6,017,709 A | 1/2000 | Hardin et al. |
| 6,027,880 A | 2/2000 | Cronin et al. |
| 6,046,004 A | 4/2000 | Wu et al. |
| 6,048,690 A | 4/2000 | Heller et al. |
| 6,060,242 A | 5/2000 | Nie et al. |
| 6,107,078 A | 8/2000 | Keese et al. |
| 6,117,657 A | 9/2000 | Usman et al. |
| 6,251,591 B1 | 6/2001 | Wu et al. |
| 6,255,050 B1 | 7/2001 | Nie et al. |
| 6,255,469 B1 | 7/2001 | Seeman et al. |
| 6,265,170 B1 | 7/2001 | Picard et al. |
| 6,287,772 B1 | 9/2001 | Stefano et al. |
| 6,294,333 B1 | 9/2001 | Daksis et al. |

FOREIGN PATENT DOCUMENTS

| | | |
|---|---|---|
| GB | 2333359 A | 7/1999 |
| GB | 2338301 A | 12/1999 |
| WO | WO 95/01370 A1 | 1/1995 |
| WO | WO 97/45539 A1 | 12/1997 |
| WO | WO 99/67628 A1 | 12/1999 |
| WO | WO 00/20633 A1 | 4/2000 |

OTHER PUBLICATIONS

Golankiewicz et al., "Non–bonding base–base interaction in nucleic acids", Bull. Acad. Pol. Sci., Ser. Sci. chim. (1970), vol. 18(8), pp. 449–454.*
Abstract of JP 5237000, Yoshitami (Sep. 17, 1993).
Abstract of Giese, *J. Biomolecular Structure & Dynamics* (Jun., 2000).
Baran et al., *Nucleic Acids Research* 25:297–303 (1997).
Bohmann et al., *Science*, 238:1386–1392 (Dec. 1987).
Carlsson et al., 380 *Nature* 207 (Mar. 21, 1996).
Chan et al., *J. Mol. Med.* 75 Issue 4:267–282 (1997).
Dalrymple et al., *Nucleic Acids Research*, vol. 13, No. 21, pp. 7865–7879 (1985).
Drozdov–Tikhomirov et al., *J. Biomolecular Structure & Dynamics*, vol. 19, No. 2, pp. 279–284 (2001).
Durland et al., *Biochemistry*, 30:9246–9255 (1991).
Egholm et al., 365 *Nature* 566 (Oct. 7, 1993).
Floris et al., 260 *Eur. J. Biochem.* 801–809 (1999).
Giese et al., *Nature* 412, p. 318 (Jul. 19, 2001).
Hill et al., *Methods in Enzymology*, 278:390–416 (1997).
Johansen and Jacobsen, *J Biomol Struct Dyn*, 16(2):205–22 (Oct. 1998)(Abstract).

(List continued on next page.)

*Primary Examiner*—Gary Benzion
*Assistant Examiner*—Arun Kr. Chakrabarti
(74) *Attorney, Agent, or Firm*—Caesar, Rivise, Bernstein, Cohen & Pokotilow, Ltd.

(57) ABSTRACT

A method for determining an affinity of a first nucleobase-containing sequence for a second nucleobase-containing sequence includes providing a test medium containing the first nucleobase-containing sequence and the second nucleobase-containing sequence, applying a voltage across the test medium, measuring a test electric current through the test medium; and determining the affinity by evaluating whether the test electric current is equivalent to a reference electric current of a reference medium containing a longer of the first nucleobase-containing sequence and the second nucleobase-containing sequence. A complex in an electrically-stimulated phase contains at least two nucleobase-containing sequences in a medium, wherein the electrical conductivity of the medium increases linearly without a plateau as the temperature of the medium approaches and exceeds a Tm of the complex.

9 Claims, 66 Drawing Sheets

OTHER PUBLICATIONS

Kadonaga et al., *Cell*, 51:1079–1090 (Dec. 24, 1987).
Kukreti et al. 25 *Nucleic Acids Research* 4264–4270 (1997).
Marsh et al., *Nucleic Acids Research*, 23:696–700 (1995).
Marsh et al., *Biochemistry* 33:10718–10724 (1994).
U.S. patent application Ser. No. 09/468,679, Daksis et al.
U.S. patent application Ser. No. 09/613,263, Erikson et al.
U.S. patent application Ser. No. 09/664,827, Erikson et al.
U.S. patent application Ser. No. 09/713,177, Erikson et al.
U.S. patent application Ser. No. 09/885,731, Erikson et al.
Mazumder et al., *Biochemistry* 35:13762–13771 (1996).
Porath, et al., 403 *Nature* 635 (Feb. 10, 2000).
Sen et al., *Nature* 334:364–366 (1988).
Sen et al., *Biochemistry* 31:65–70 (1992).
Sturm et al., *Genes & Development*, 2:1582–1599 (1988).
Tomac et al., 118 *J. Am. Chem. Soc.* 5544–5552 (1996).
Watson, James, "A Personal Account of the Discovery of the Structure of DNA," (1968).
Williamson et al., *Cell* 59:871–880 (Dec. 1, 1989).
U.S. patent application Ser. No. 09/909,496, Erikson et al.
U.S. patent application Ser. No. 09/911,047, Erikson et al.
U.S. patent application Ser. No. 09/961,885, Erikson et al.
Wilson et al., *Cell*, 74:115–125 (Jul. 16, 1993).
Zhurkin et al., *J. Mol. Biol.*, vol. 239, 181–200 (1994).

* cited by examiner

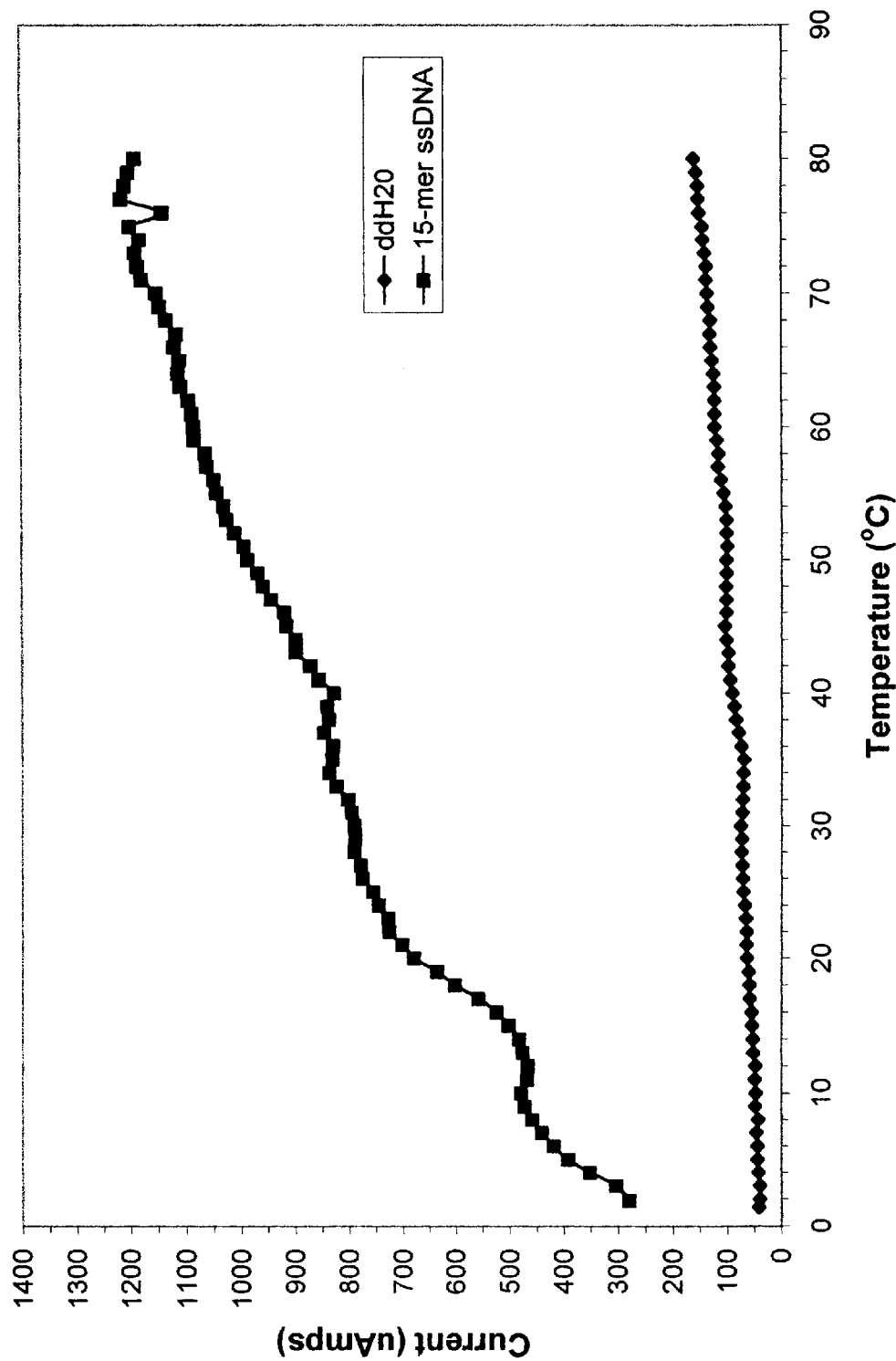
Fig. 1A. Comparison of IPA between ddH₂O and 15-mer ssDNA (8 pmoles/500 ul) at 9V with increasing temperature

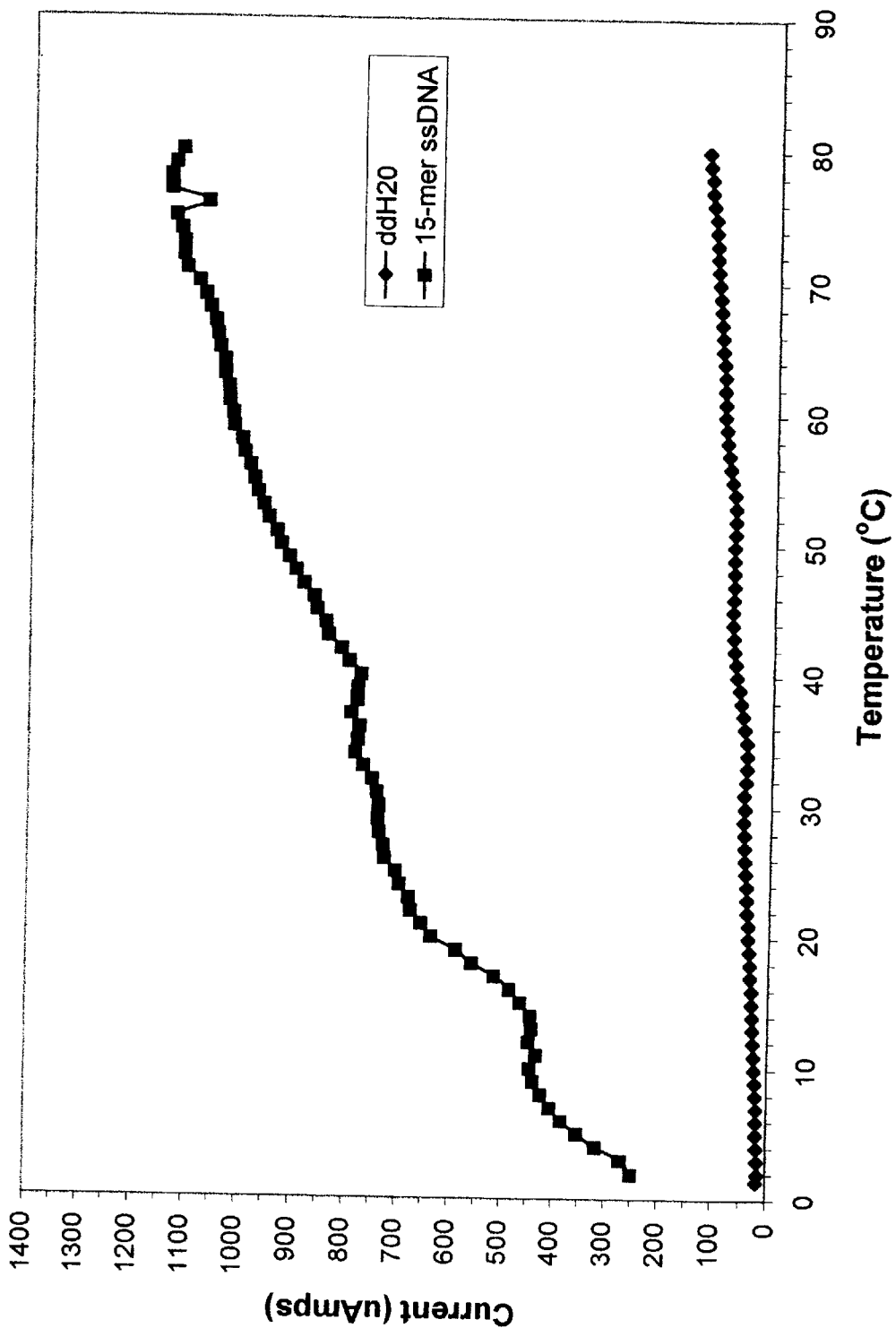
Fig. 1B. Comparison of AA between ddH₂0 and 15-mer ssDNA (8 pmoles/500 ul) at 9V with increasing temperature

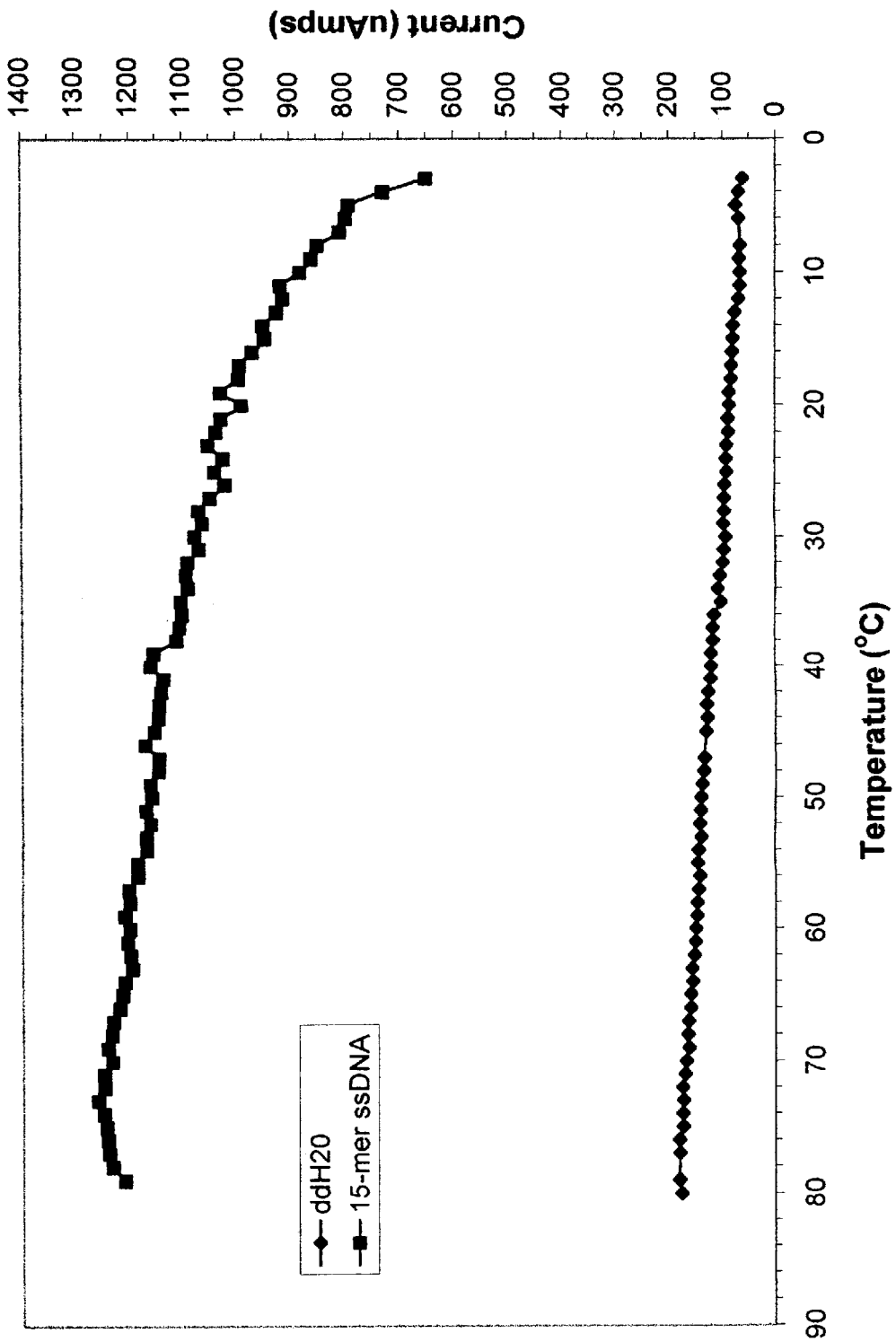

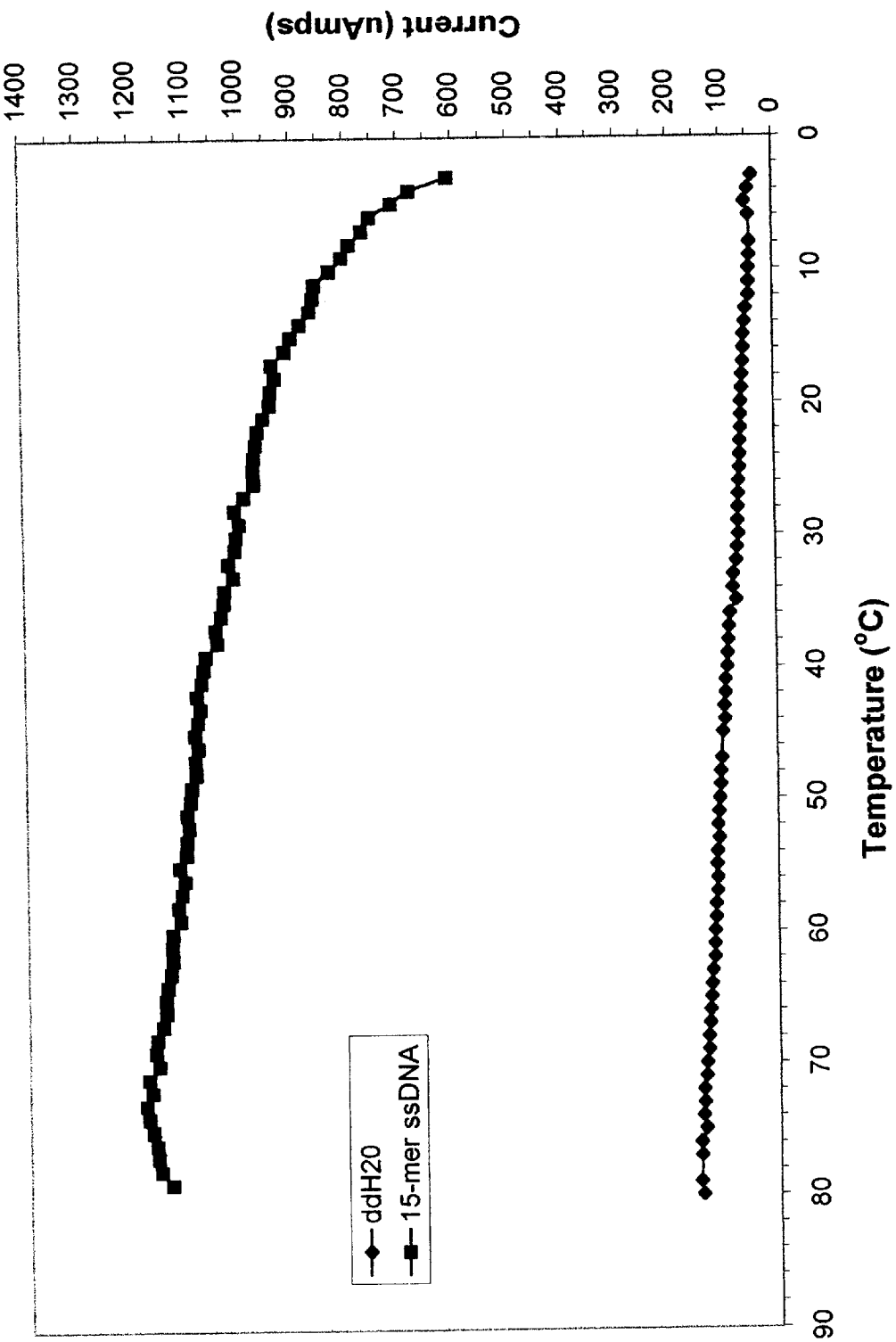
Fig. 2B. Comparison of AA between ddH$_2$O and 15-mer ssDNA (8 pmoles/500 ul) at 9V with decreasing temperature

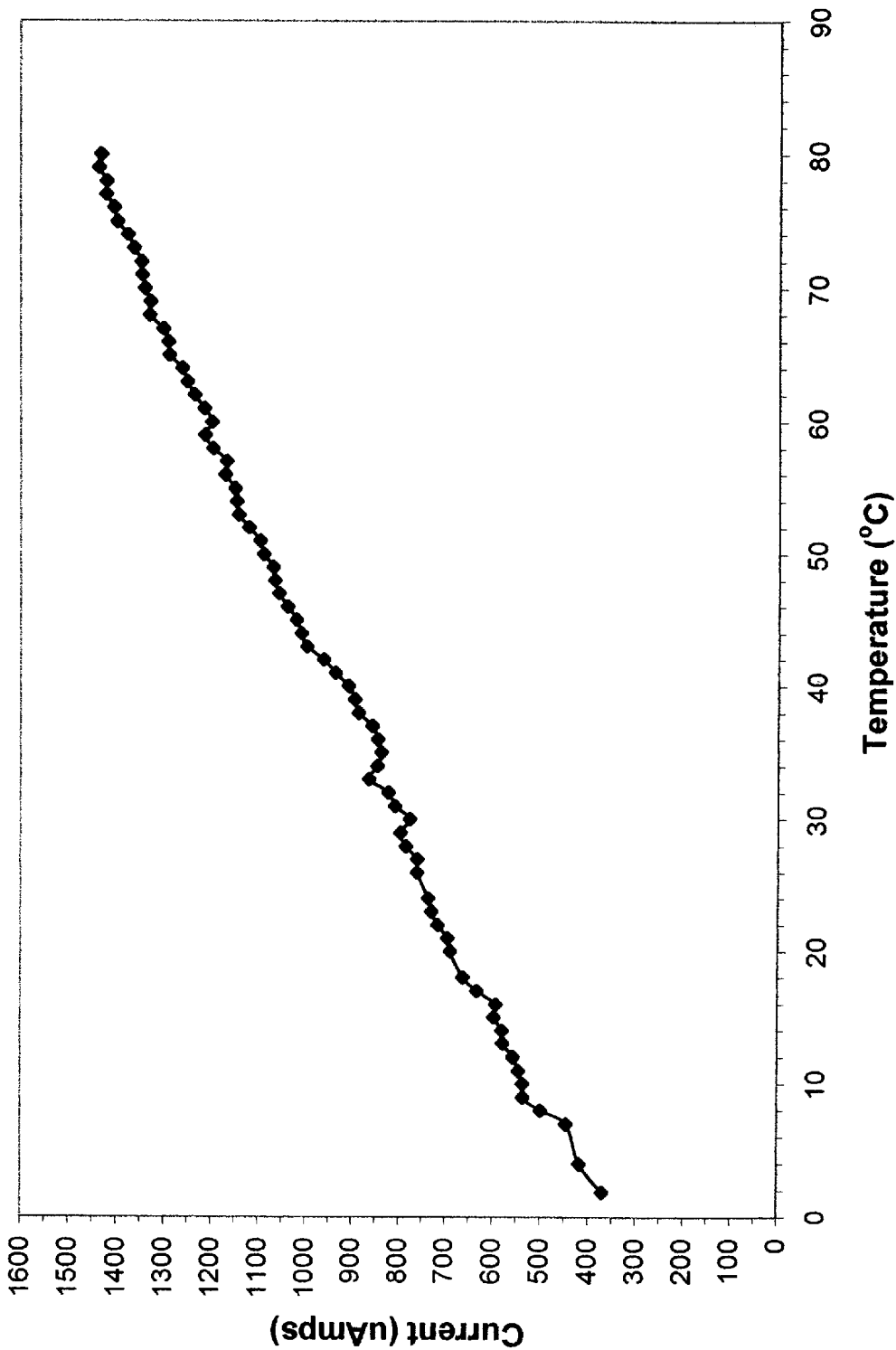
Fig. 3A. IPA of 15-mer dsDNA (8 pmoles/500 ul) at 9V with increasing temperature

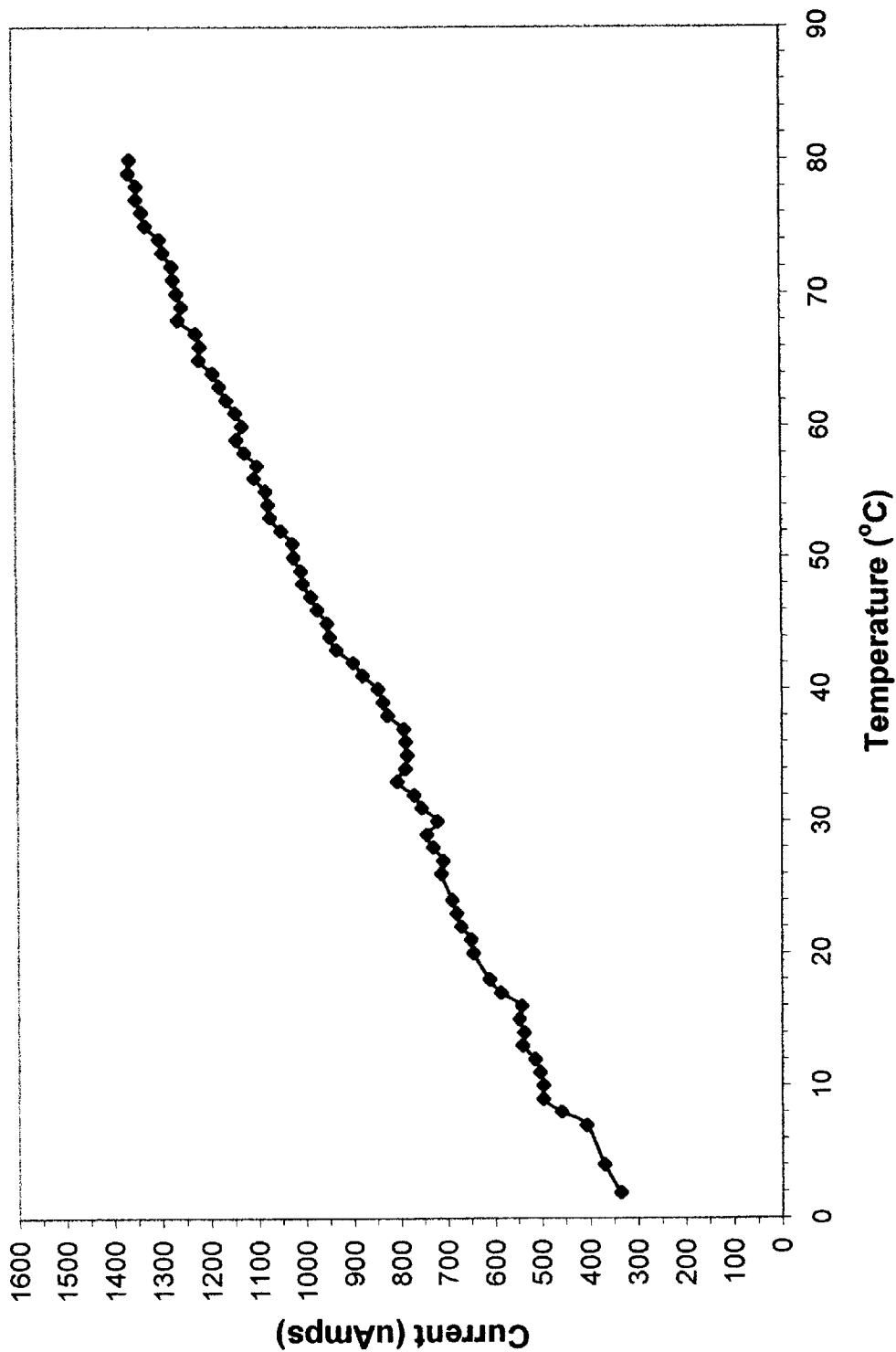

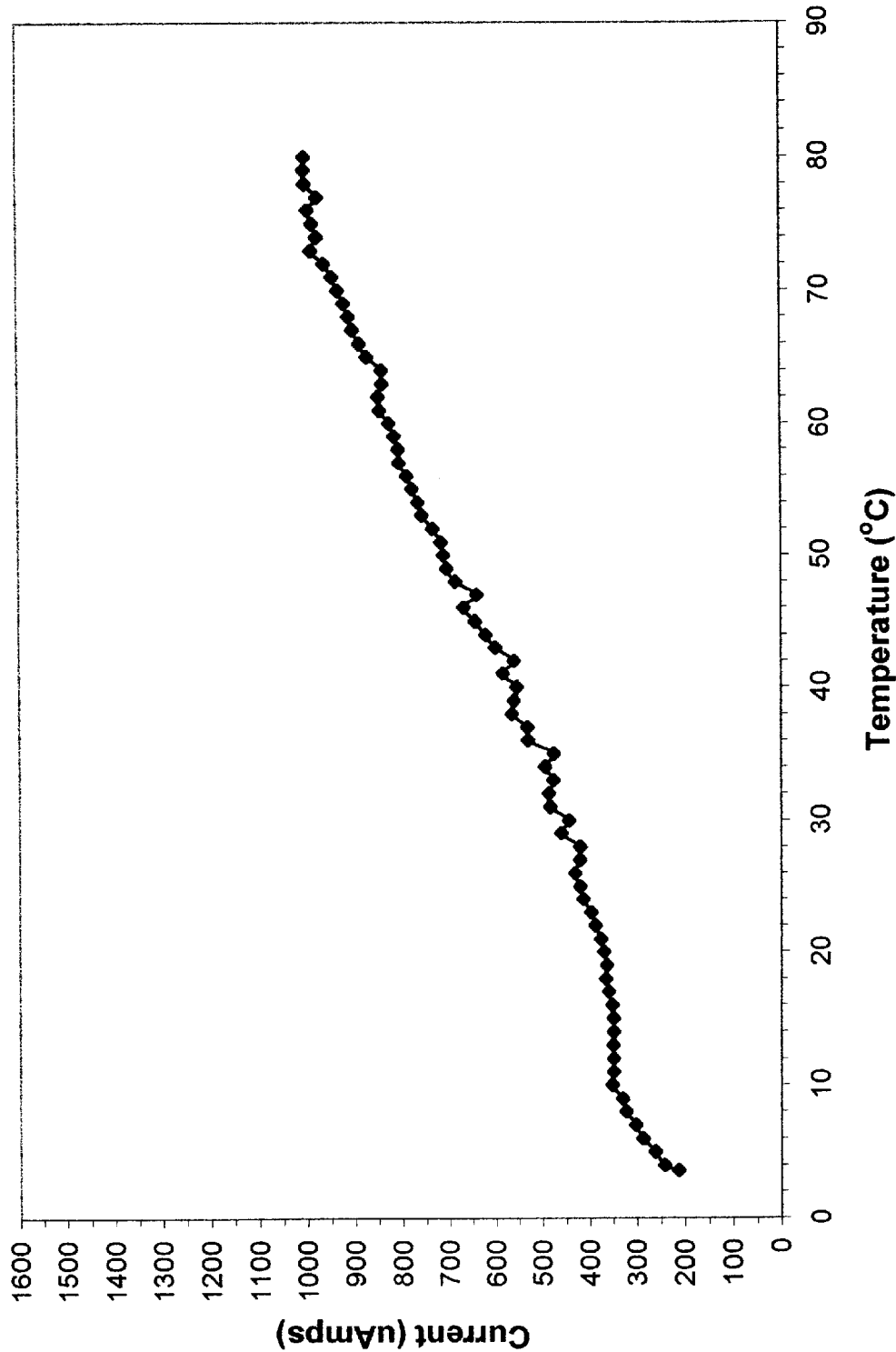
Fig. 3C. IPA of mix of 15-mer ssDNA with antiparallel complementary 15-mer ssDNA (4 pmoles each/500 ul) at 9V with increasing temperature

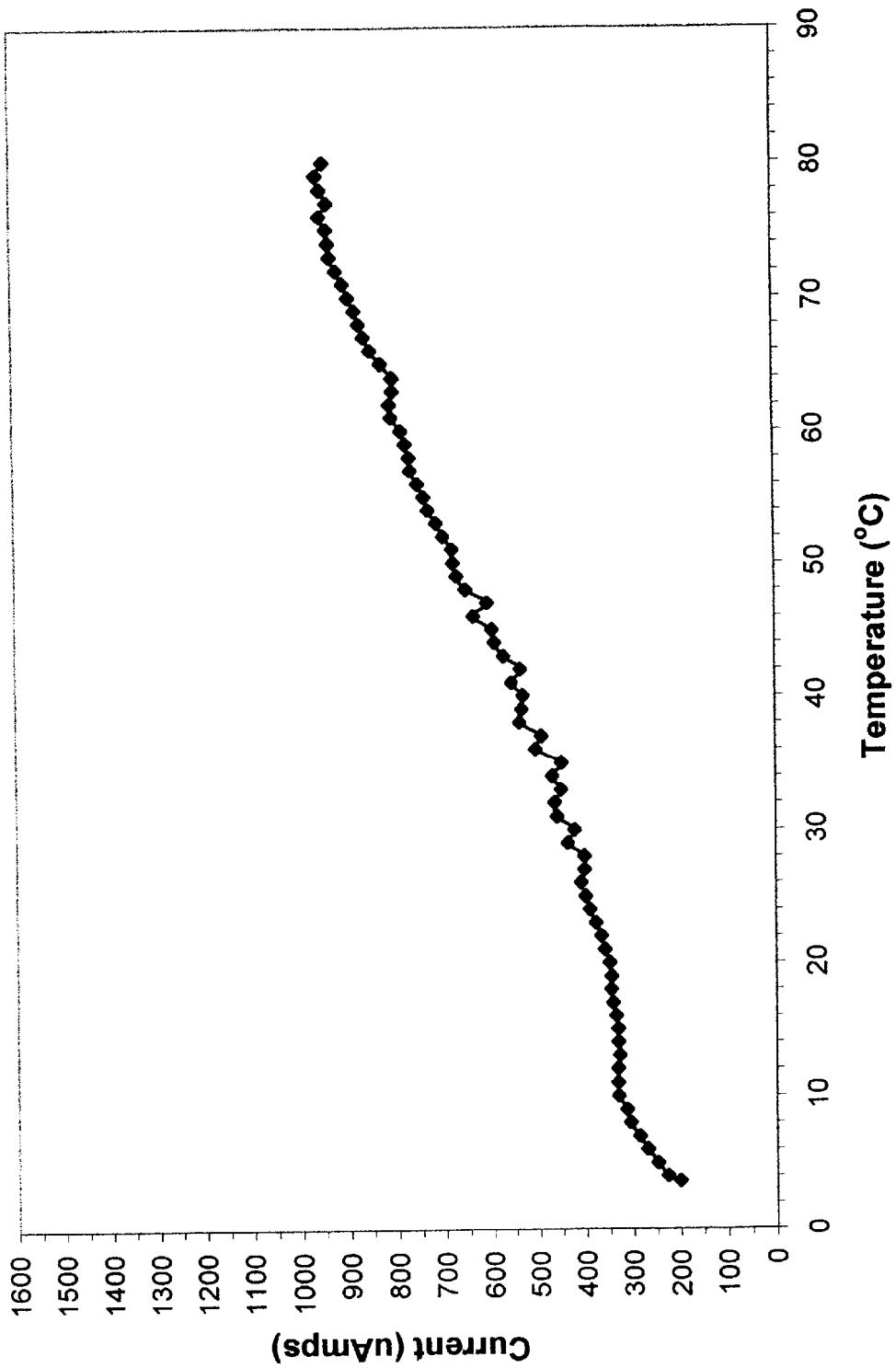
Fig. 3D. AA of mix of 15-mer ssDNA with antiparallel complementary 15-mer ssDNA (4 pmoles each/500 ul) at 9V with increasing temperature

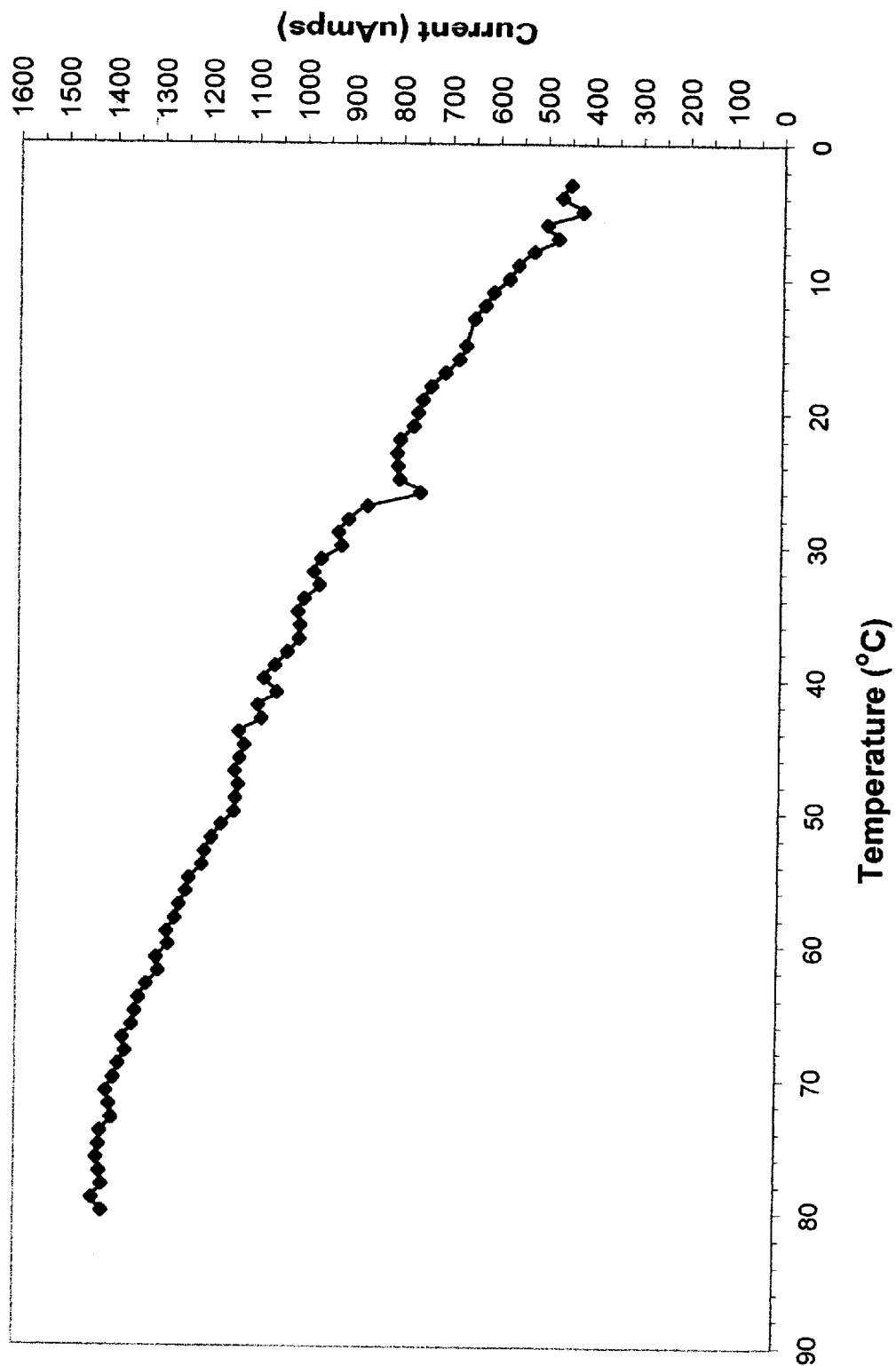
Fig. 4A. IPA of 15-mer dsDNA (8 pmoles/500 ul) at 9V with decreasing temperature

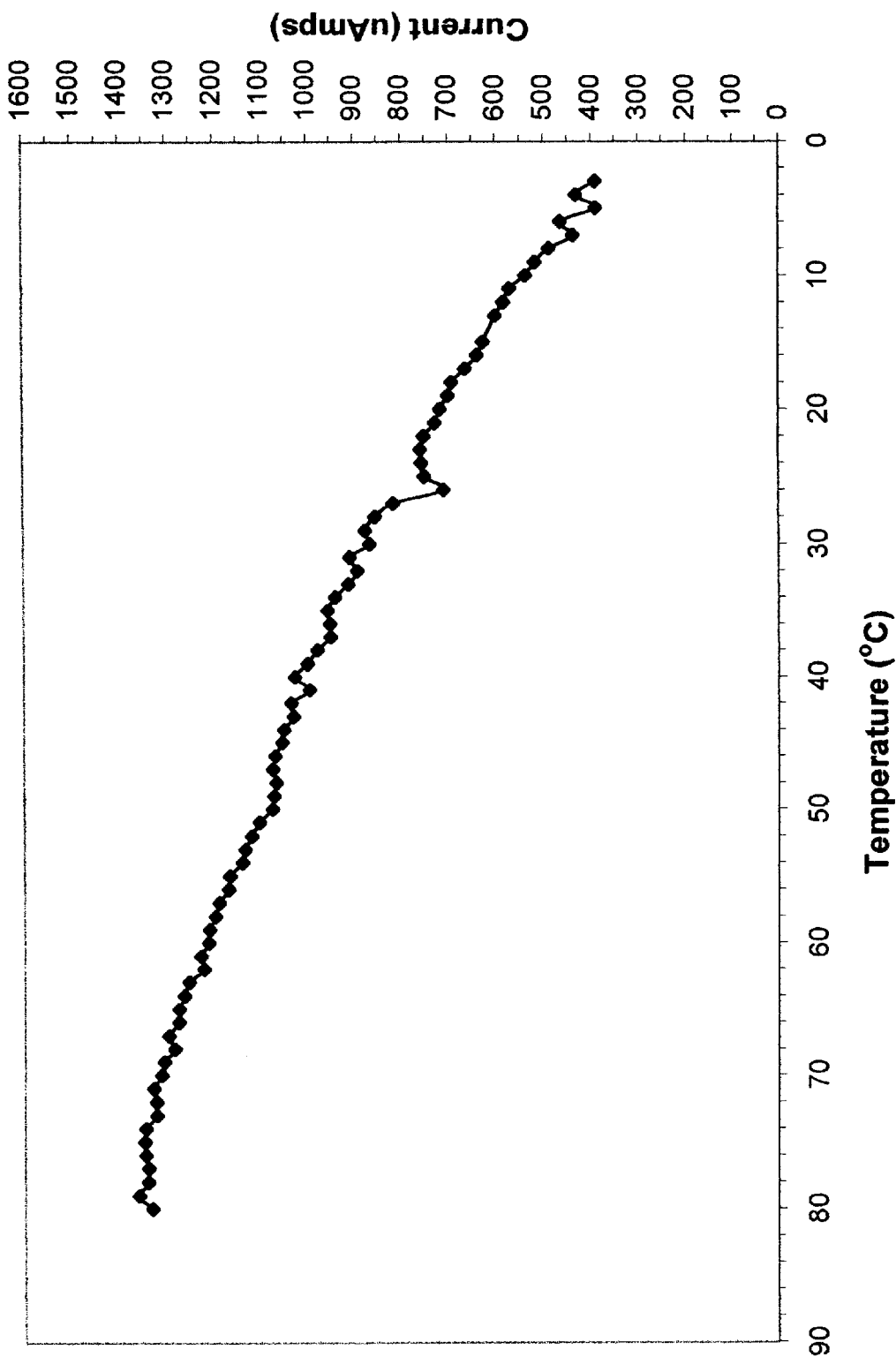
Fig. 4B. AA of 15-mer dsDNA (8 pmoles/500 ul) at 9V with decreasing temperature

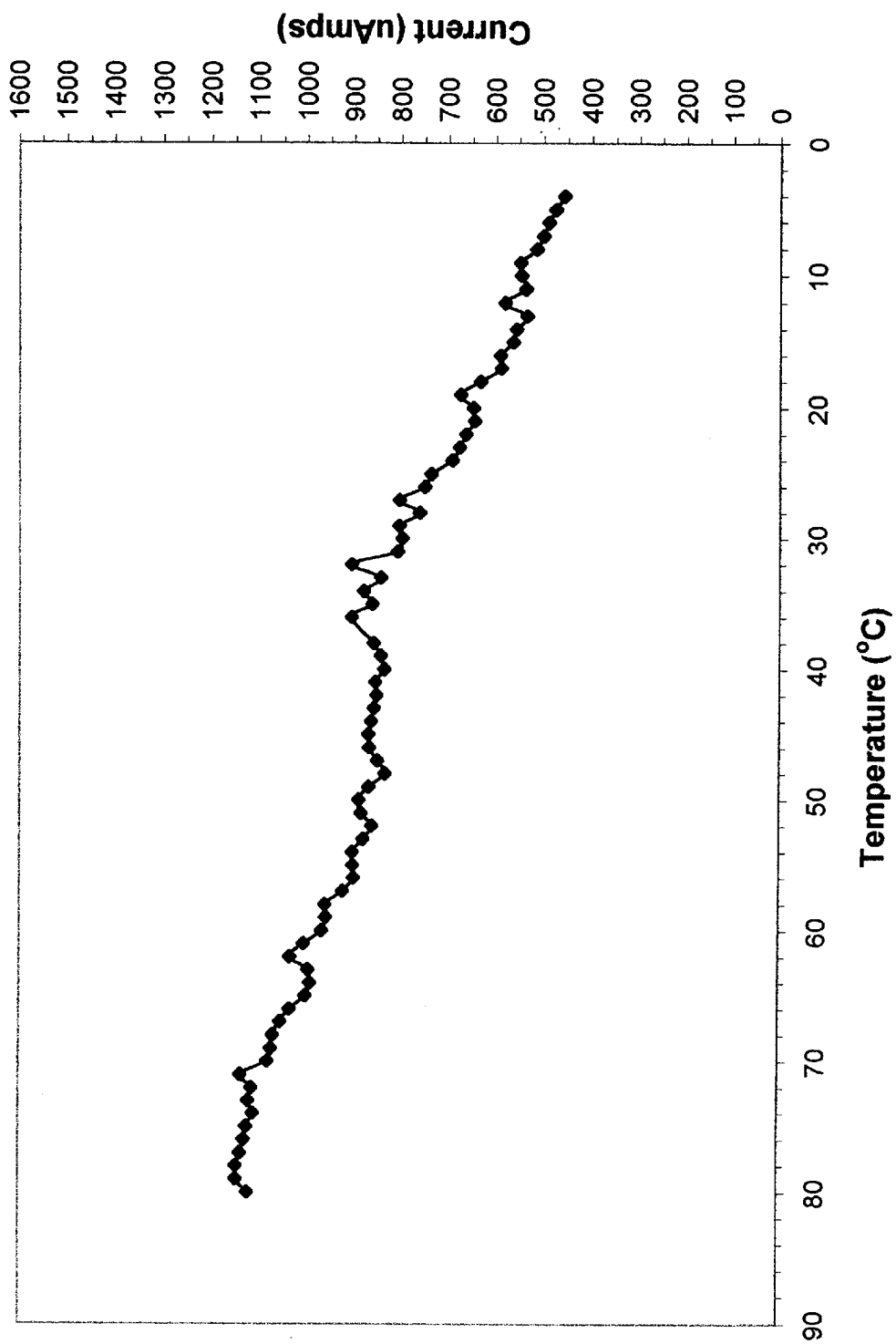
Fig. 4C. IPA of mix of 15-mer ssDNA with antiparallel complementary 15-mer ssDNA (4 pmoles each/500 ul) at 9V with decreasing temperature

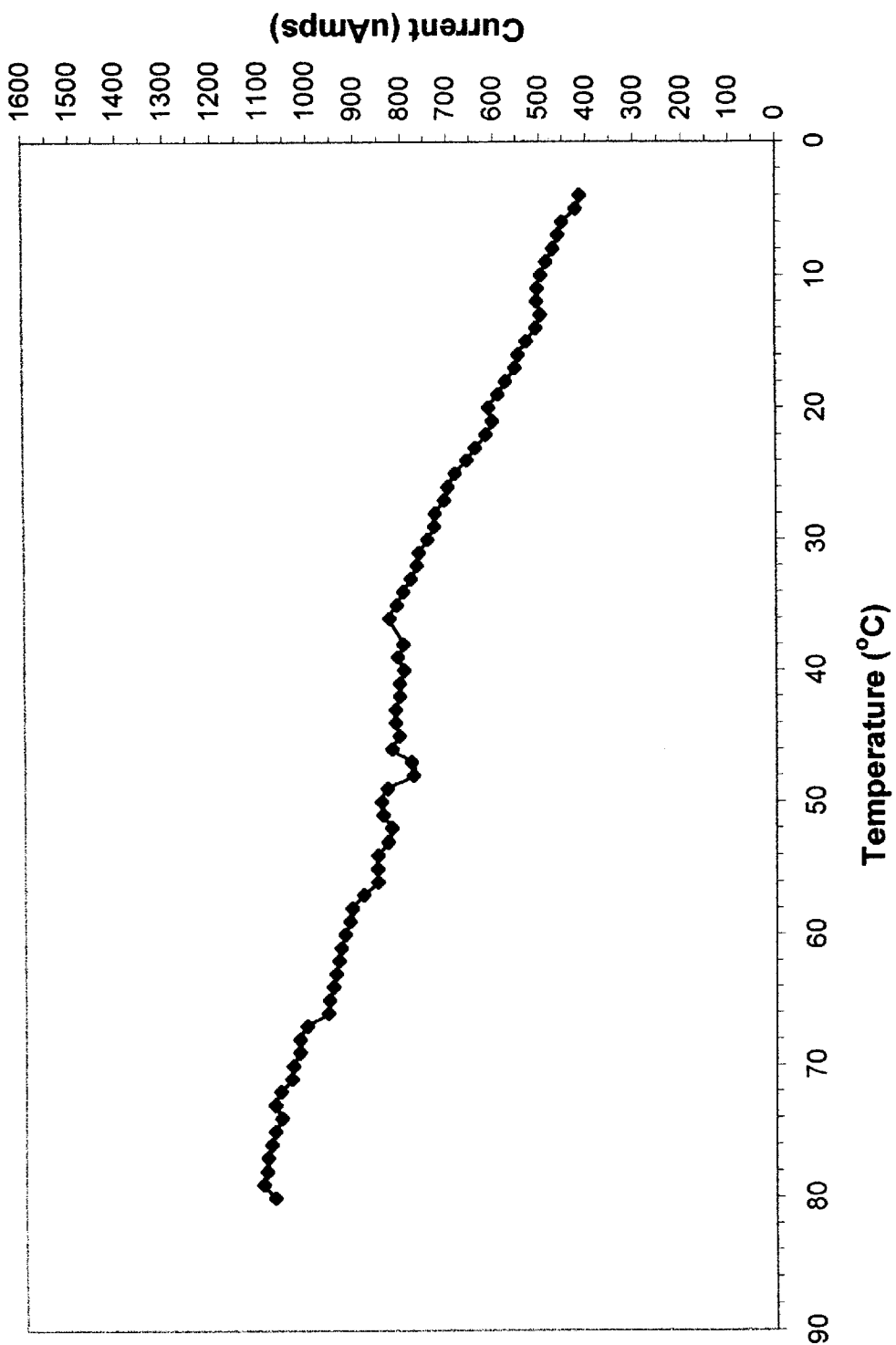
Fig. 4D. AA of mix of 15-mer ssDNA with antiparallel complementary 15-mer ssDNA (4 pmoles each/500 ul) at 9V with decreasing temperature

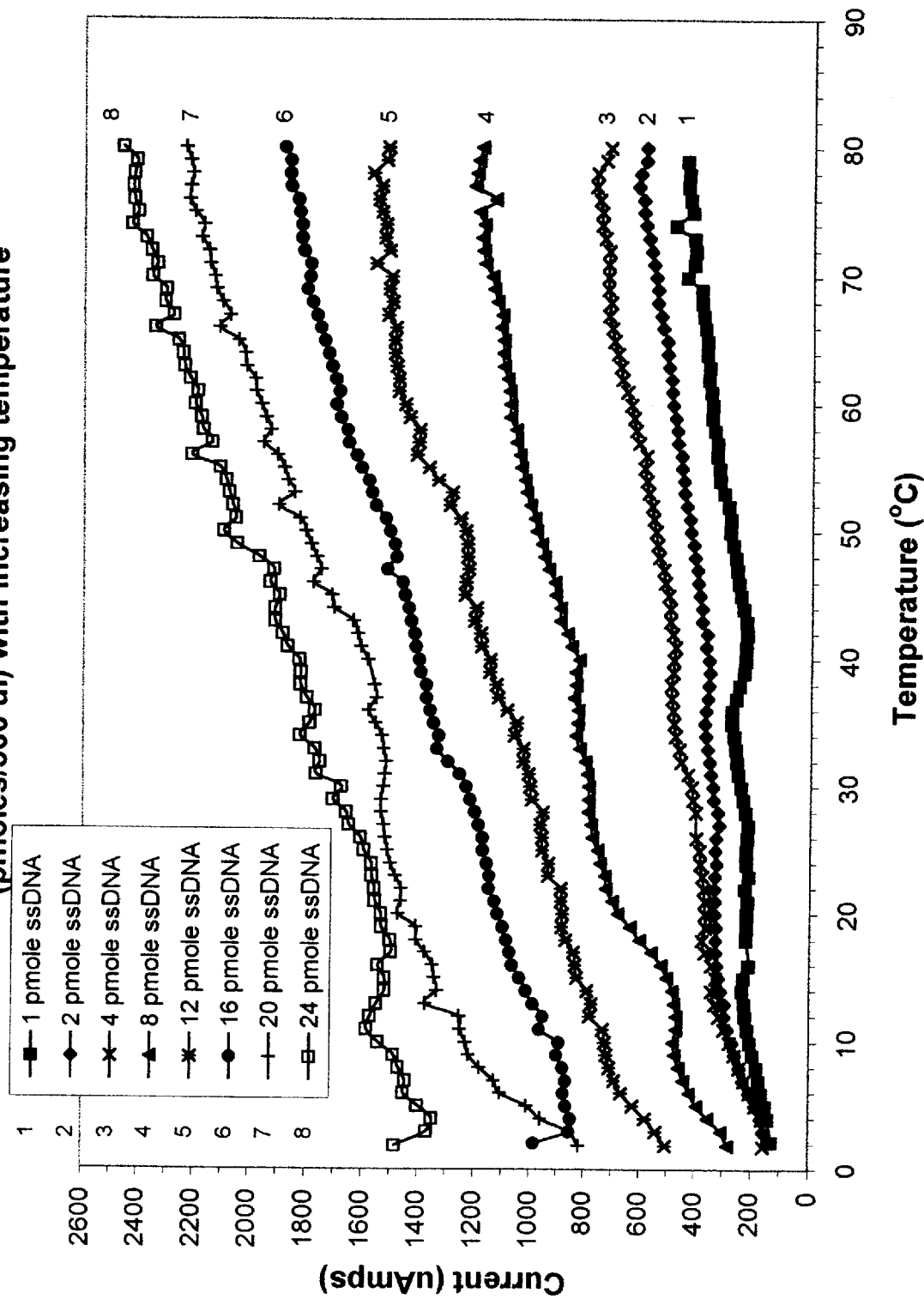

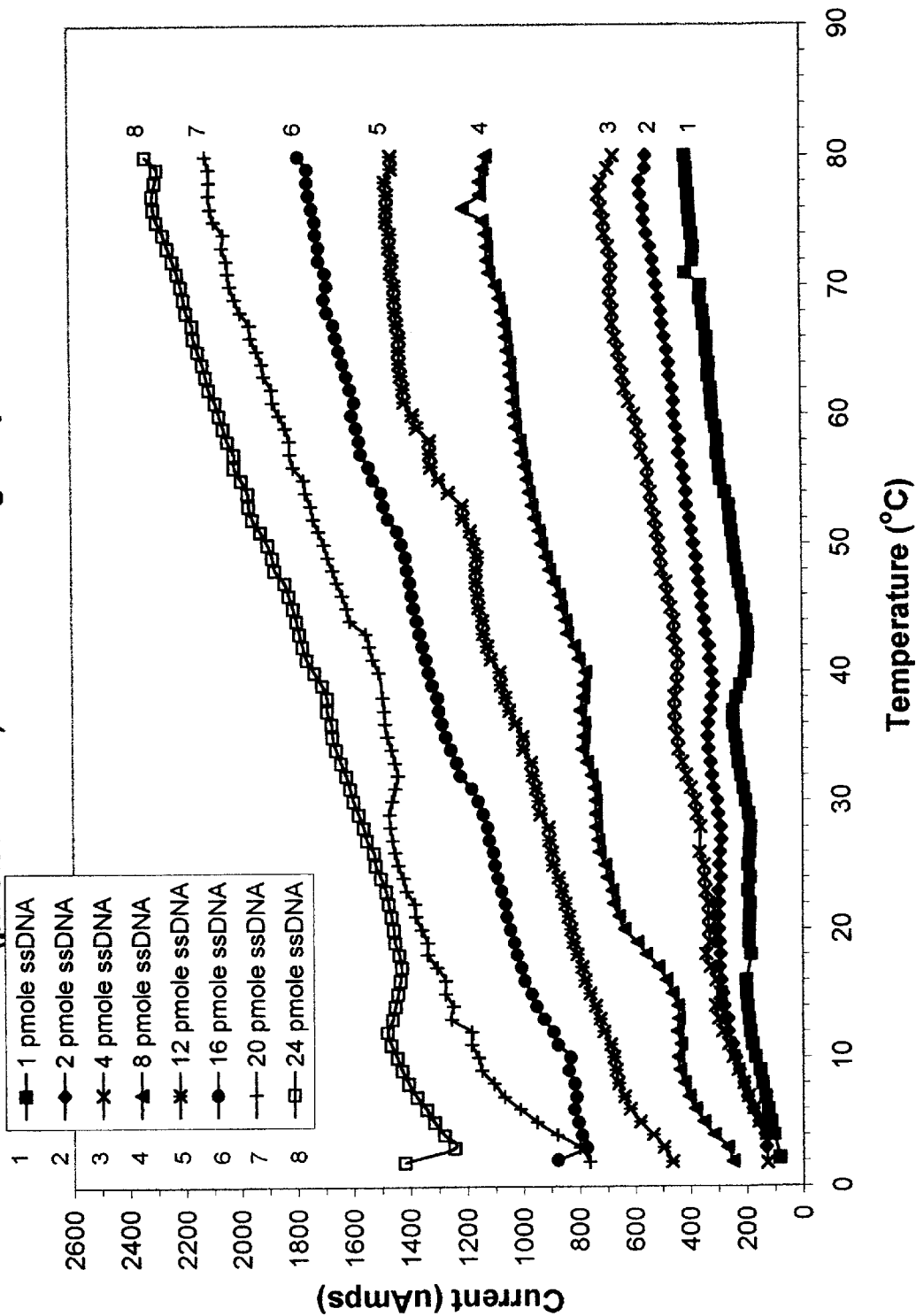

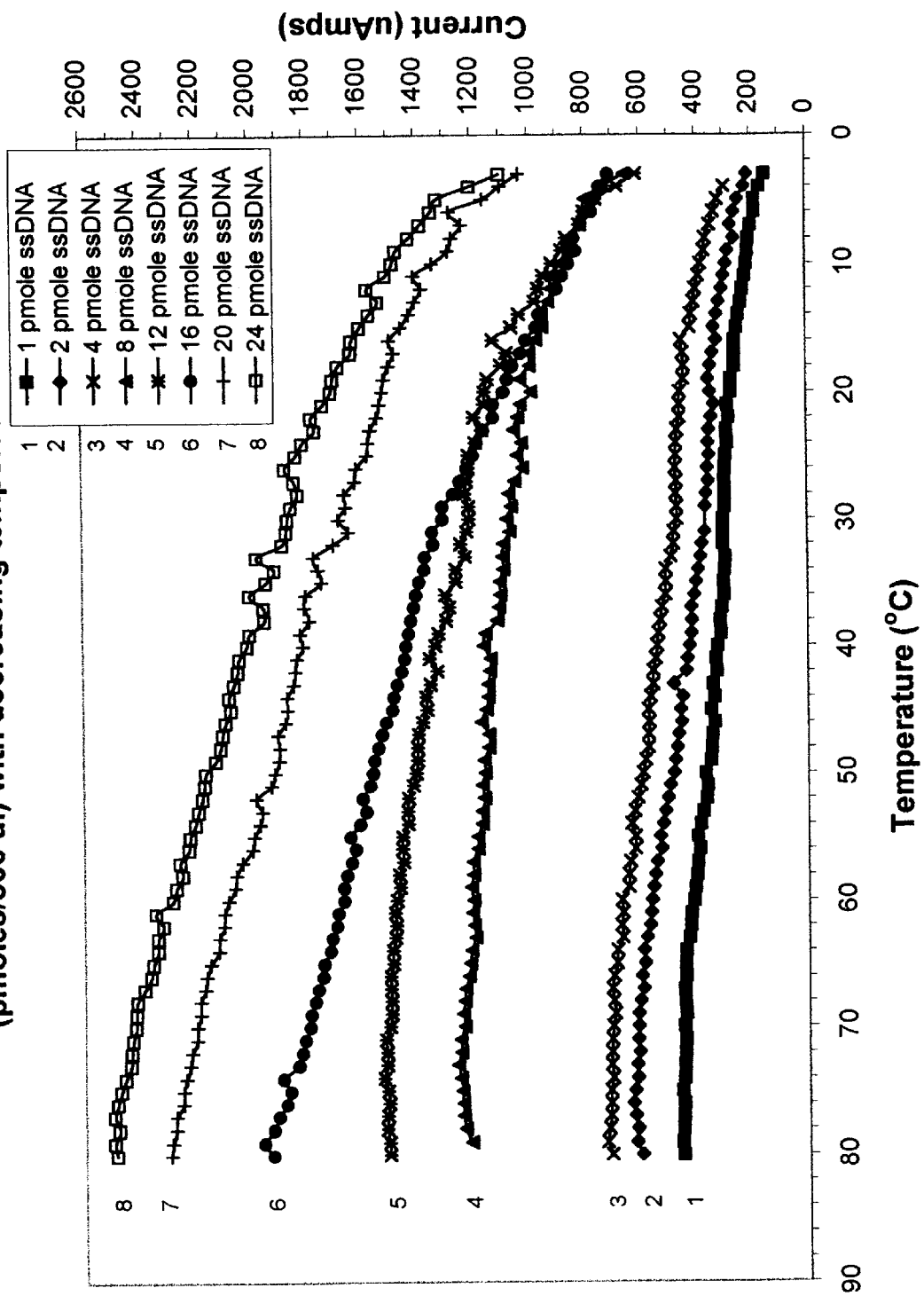

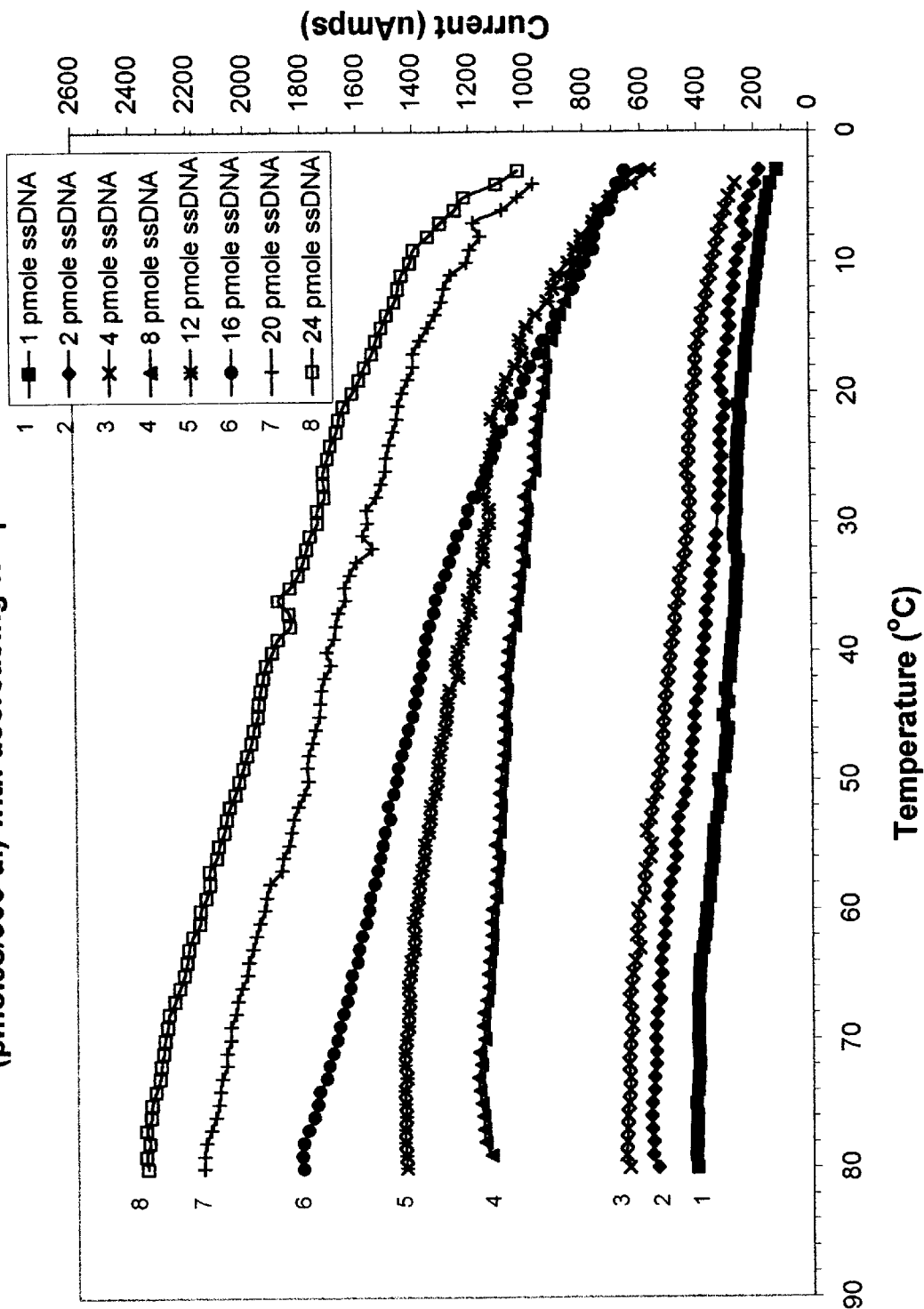

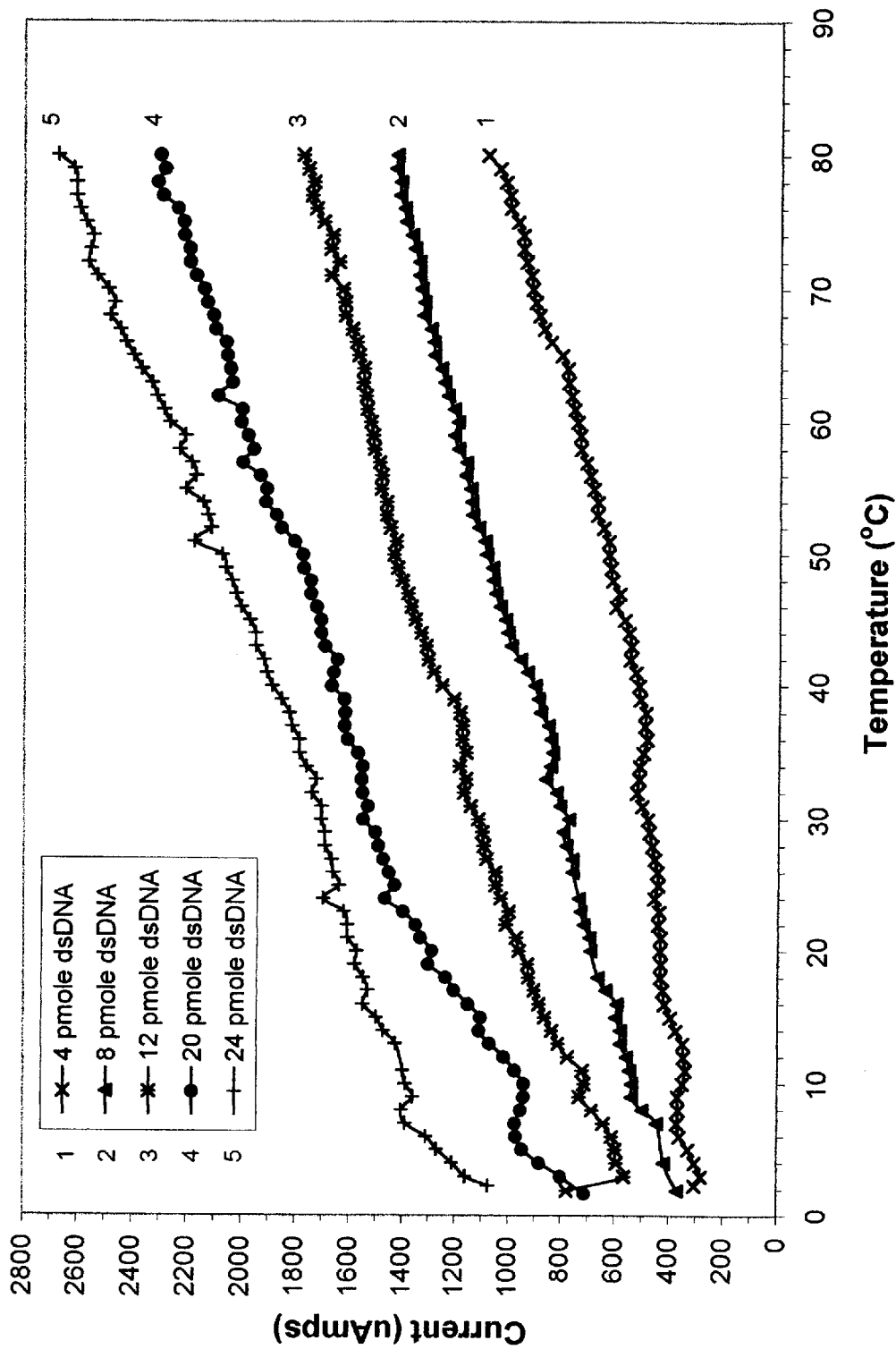
Fig. 7A. Comparison of IPA of different concentrations of 15-mer dsDNA (pmoles/500 ul) with increasing temperature

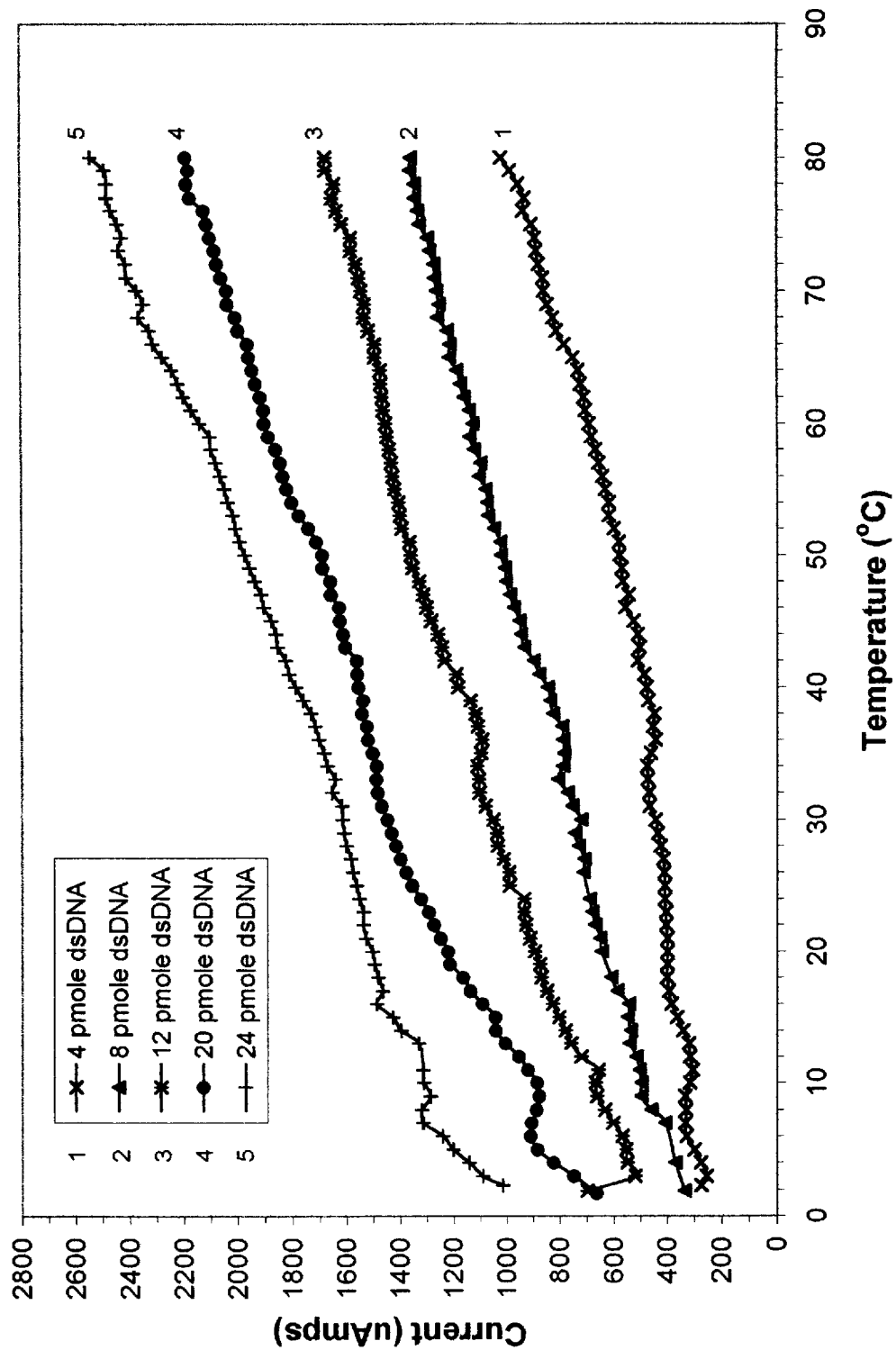

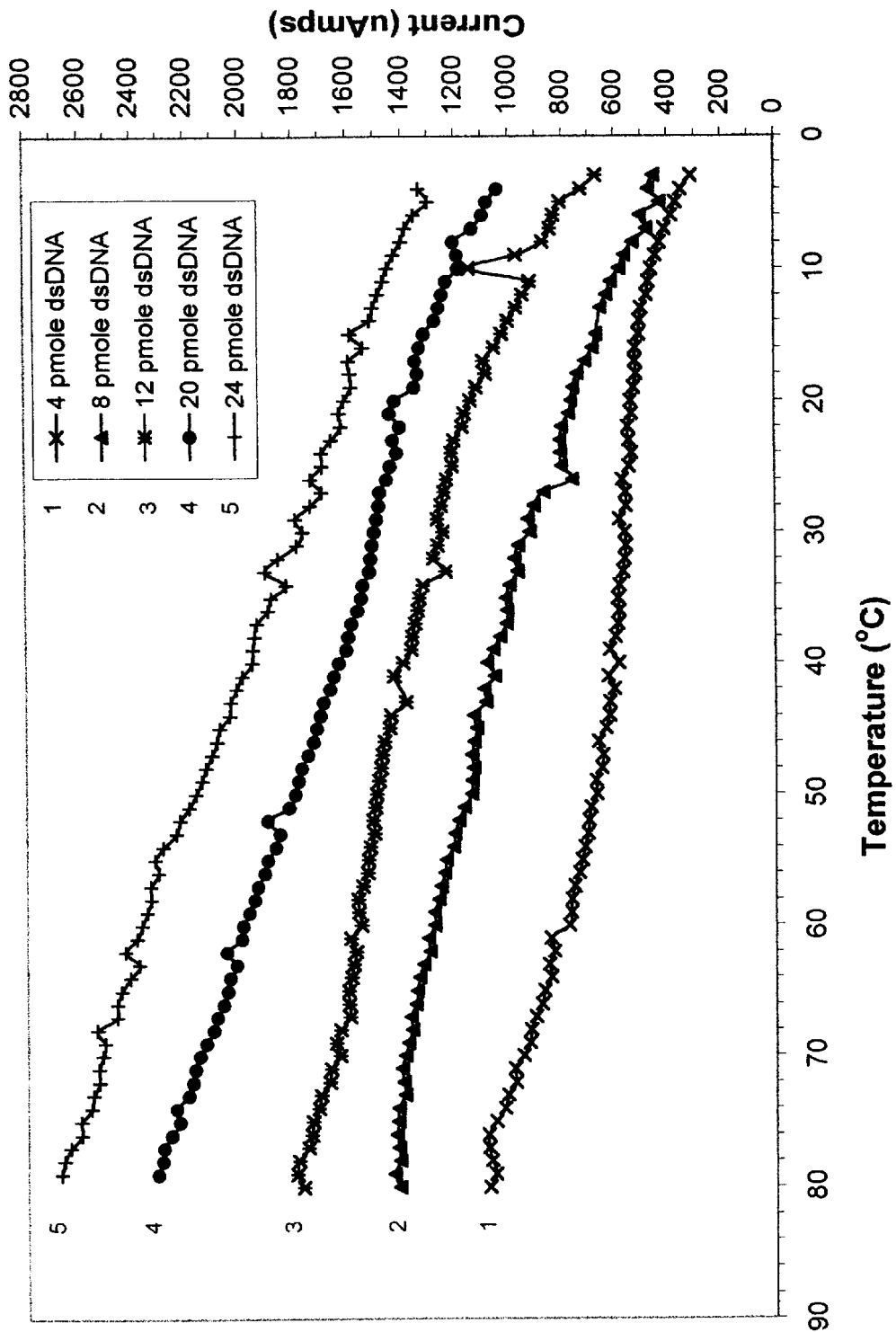
Fig. 8A. Comparison of IPA of different concentrations of 15-mer dsDNA (pmoles/500 ul) with decreasing temperature

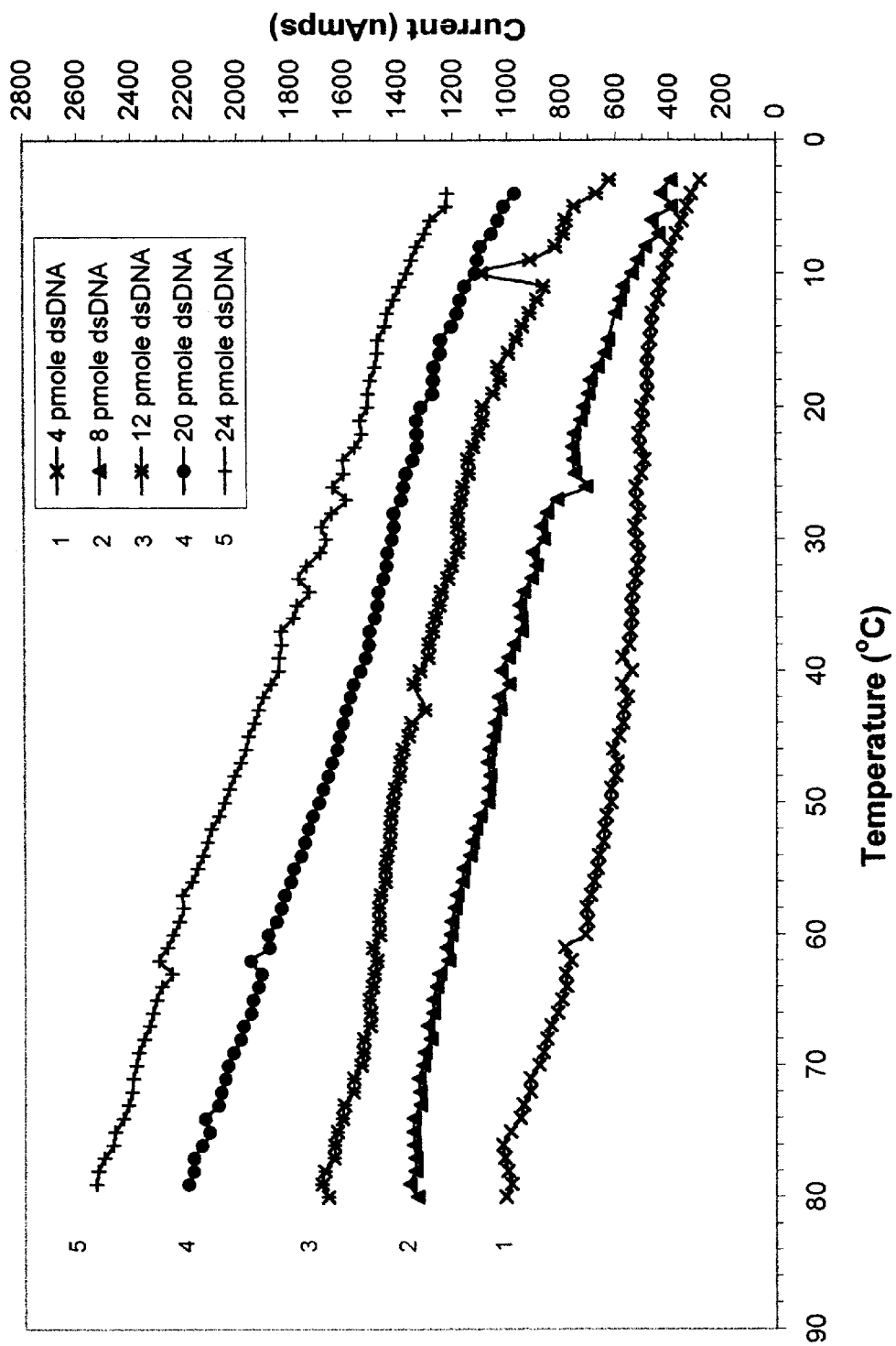

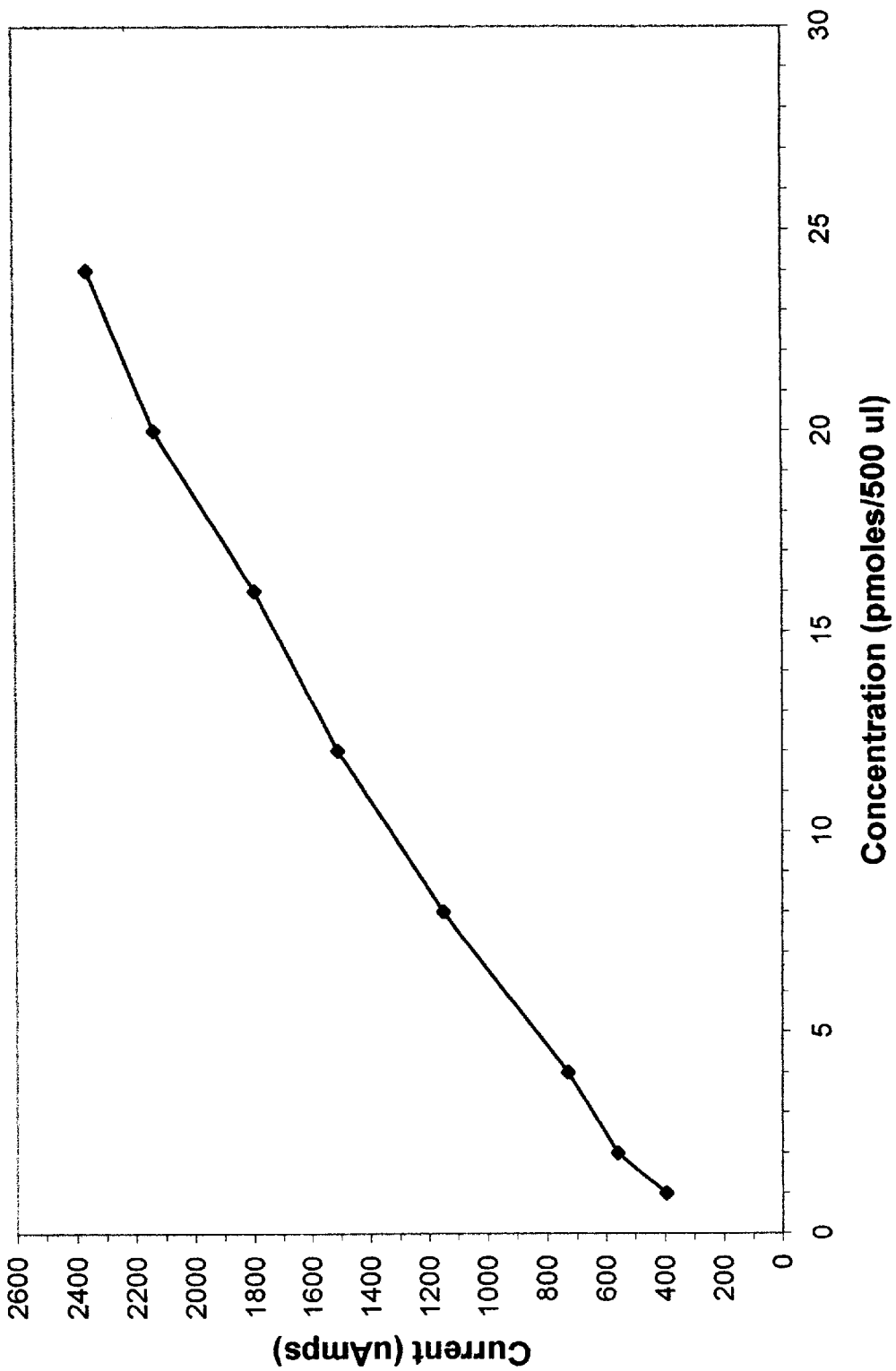
Fig. 9A. IPA of 15-mer ssDNA as a function of ssDNA concentration at 70°C

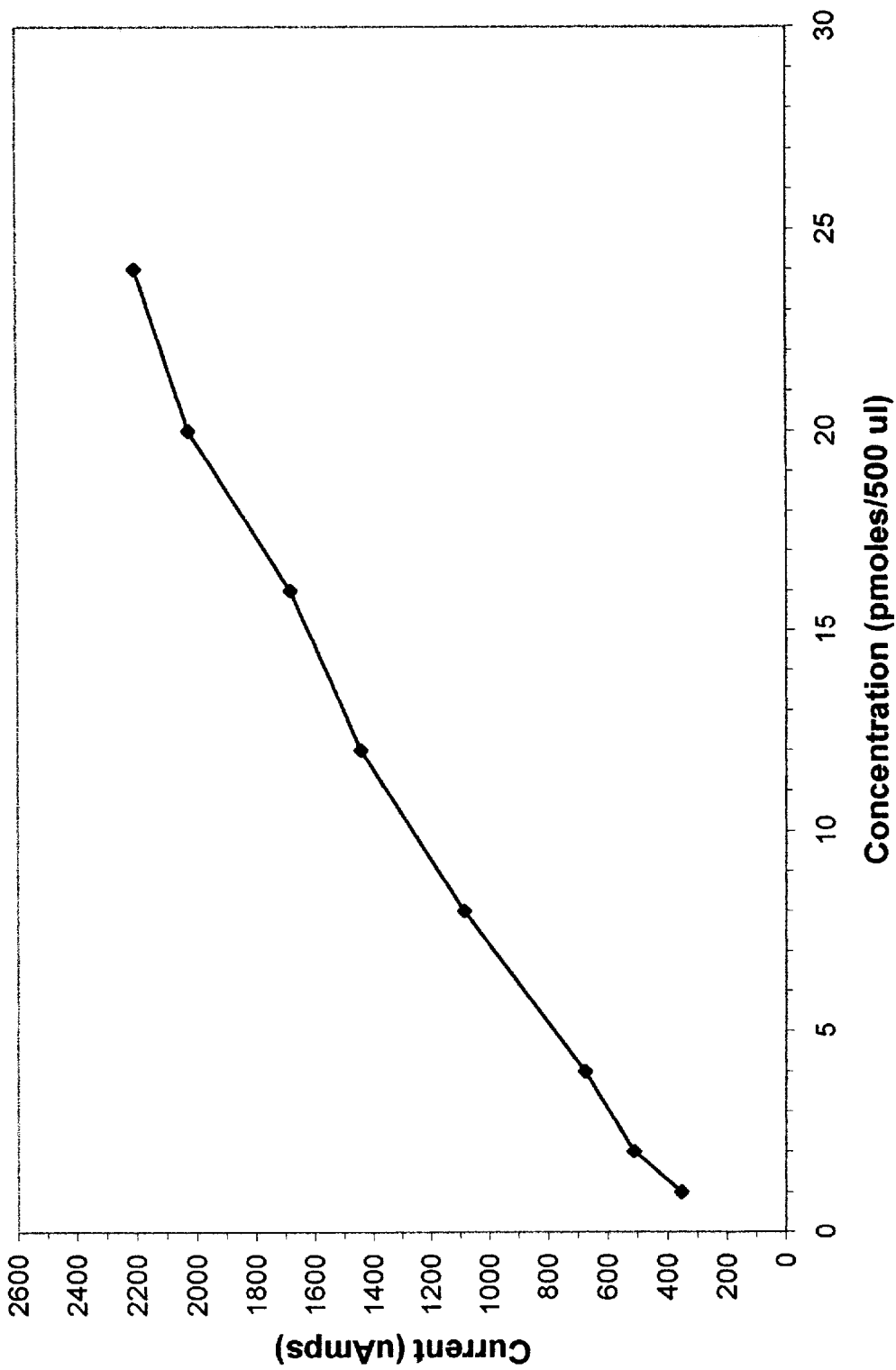
Fig. 9B. AA of 15-mer ssDNA as a function of ssDNA concentration at 70°C

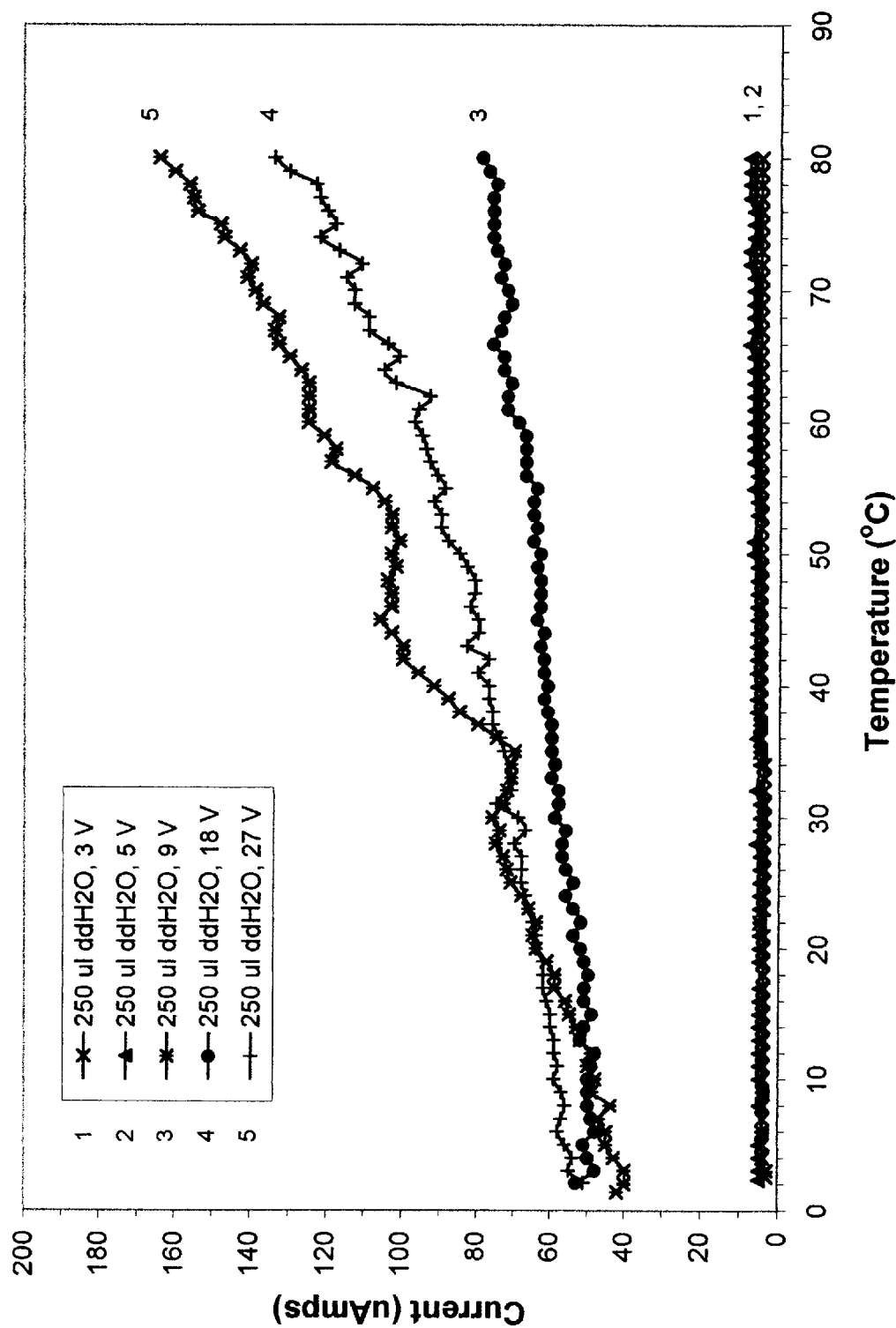

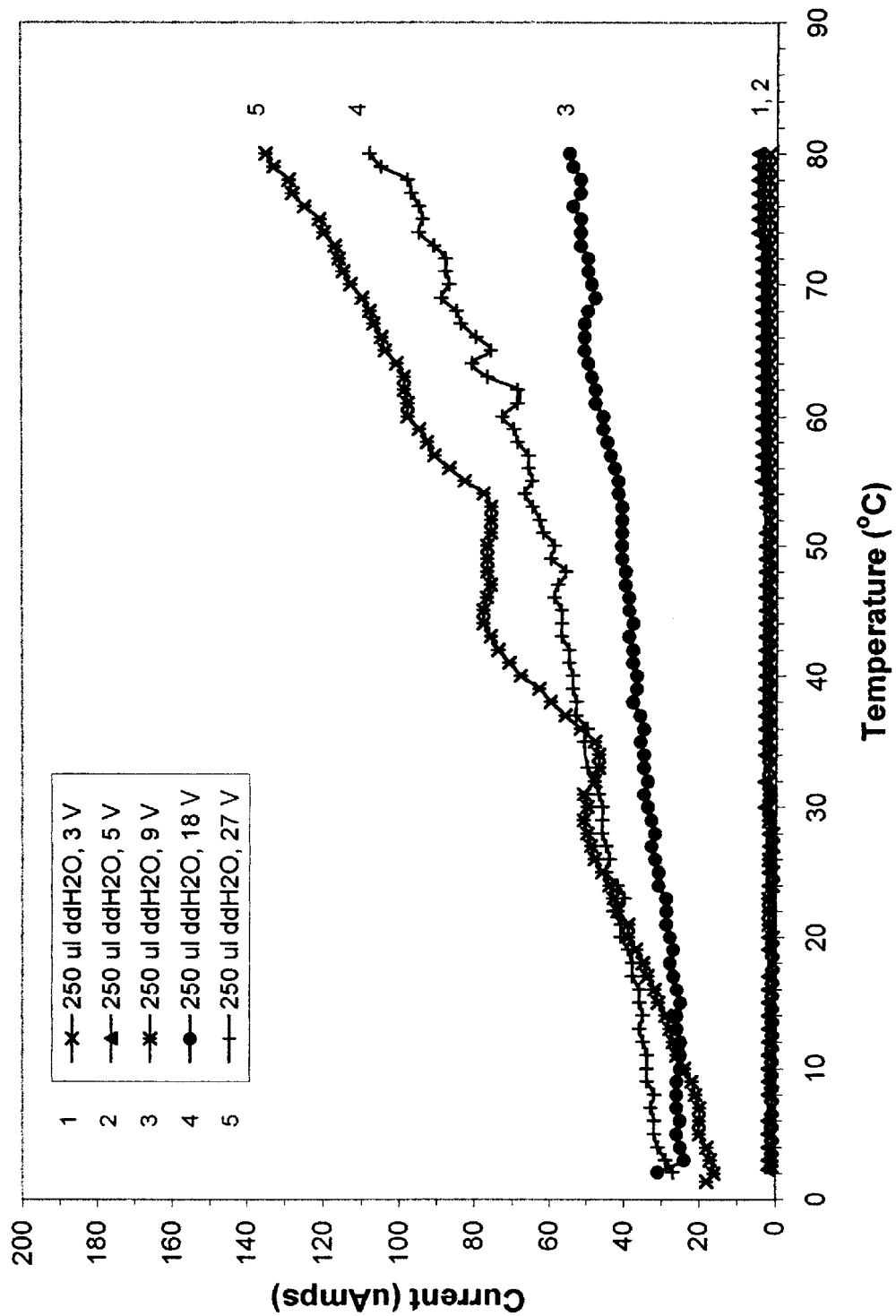
Fig. 10B. AA of ddH$_2$O with increasing temperature during different voltage applications

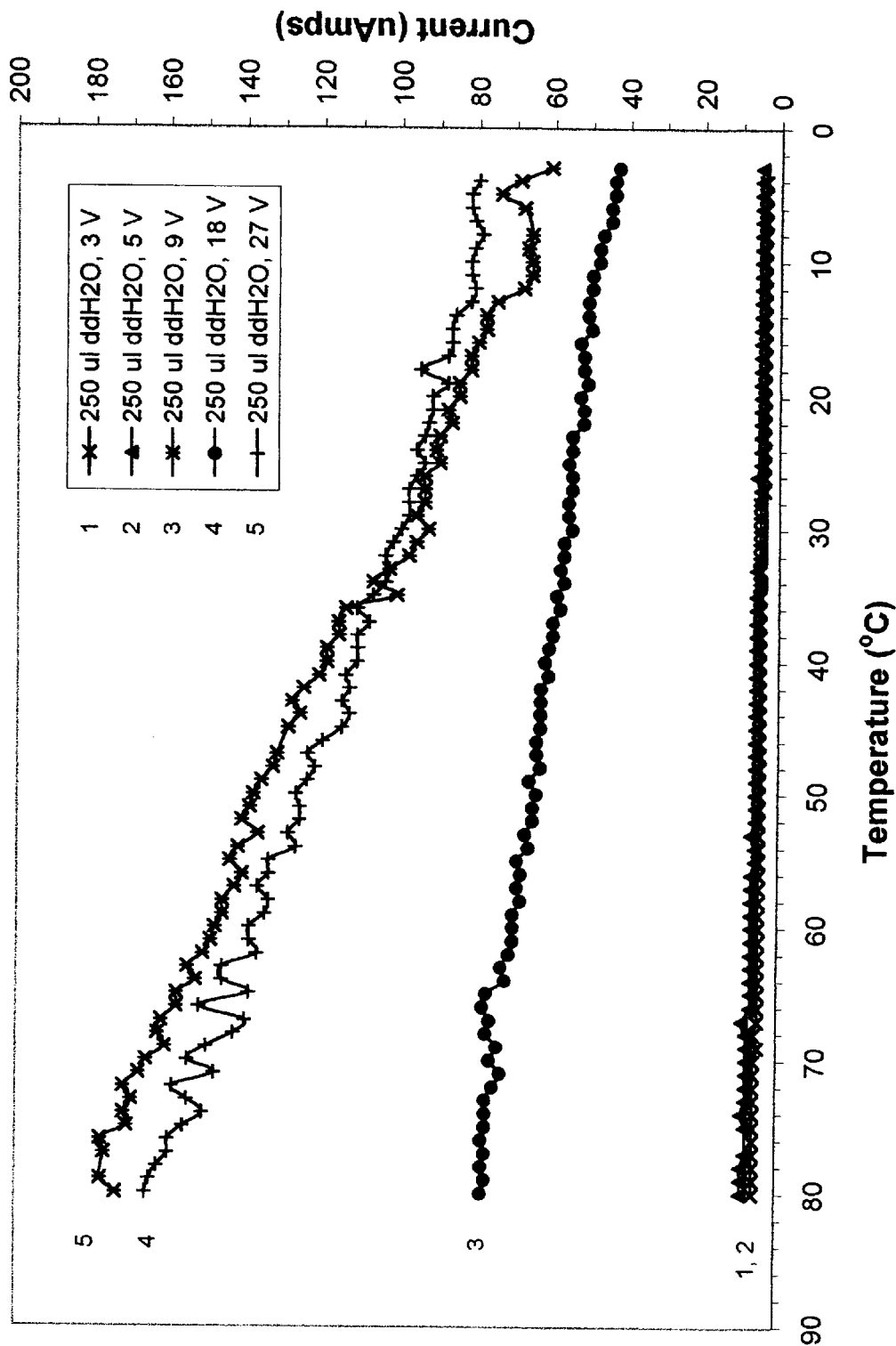
Fig. 11A. IPA of ddH₂O with decreasing temperature during different voltage applications

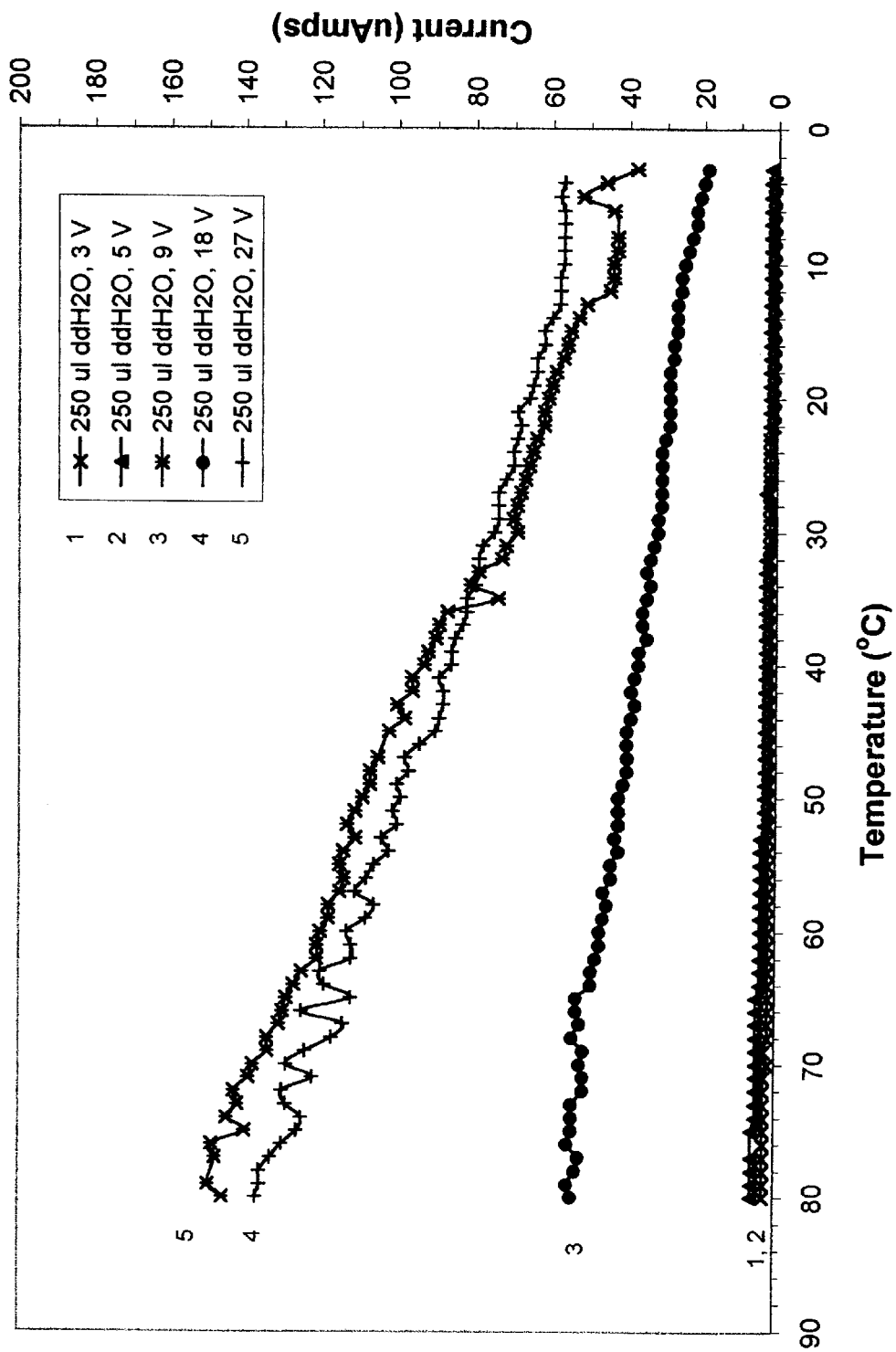
Fig. 11B. AA of ddH₂O with decreasing temperature during different voltage applications

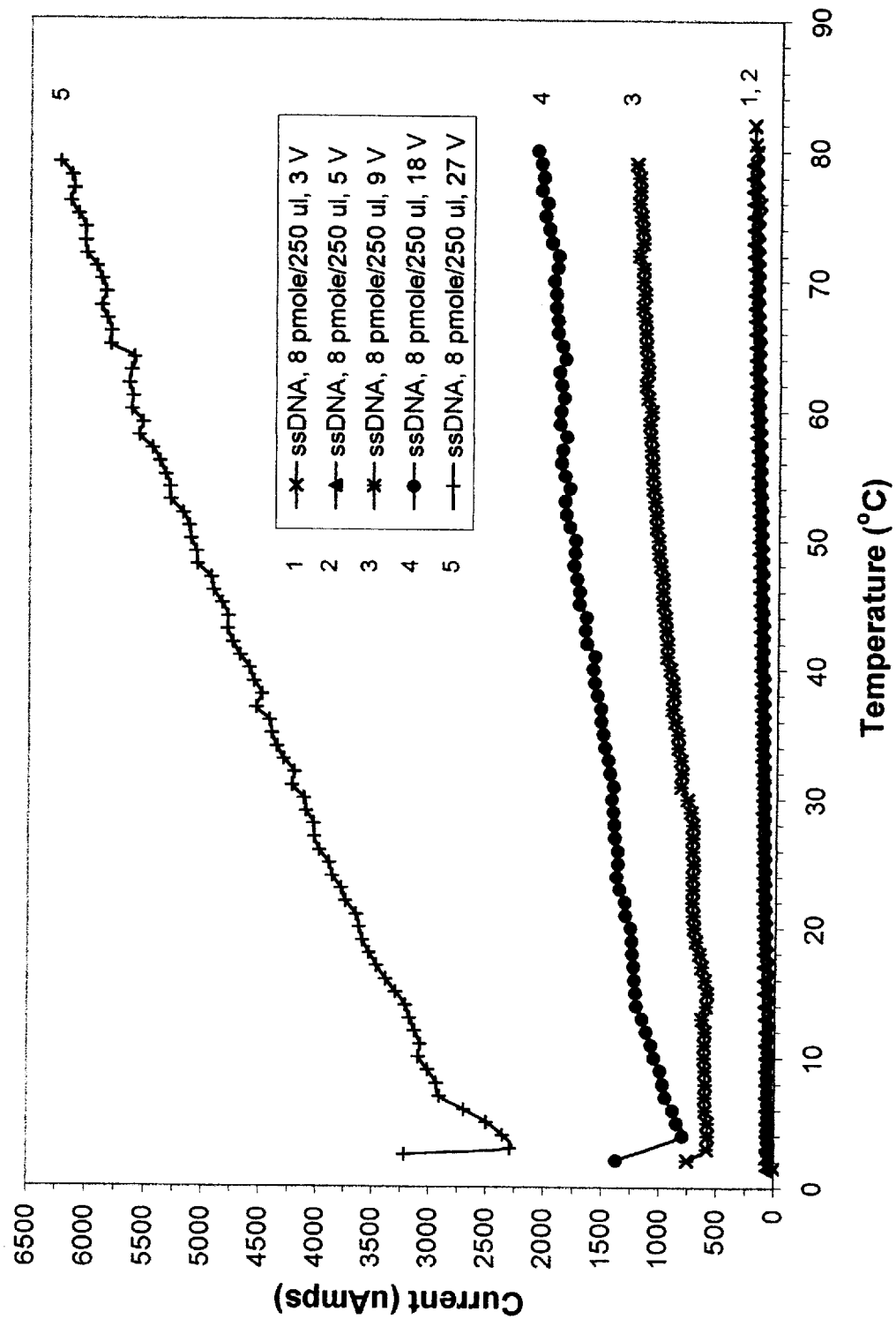
Fig. 12A. IPA of 15-mer ssDNA with increasing temperature during different voltage applications

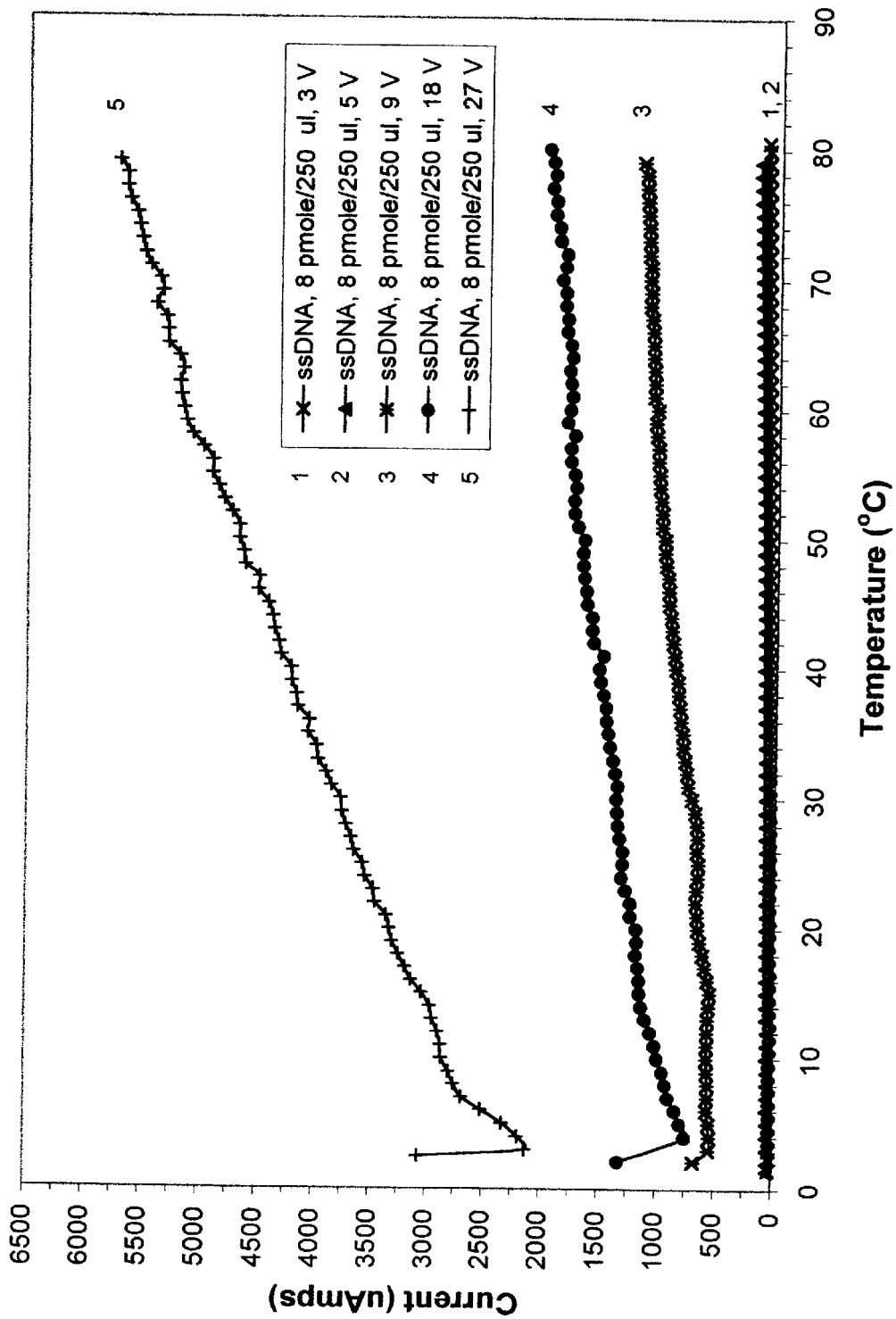
Fig. 12B. AA of 15-mer ssDNA with increasing temperature during different voltage applications

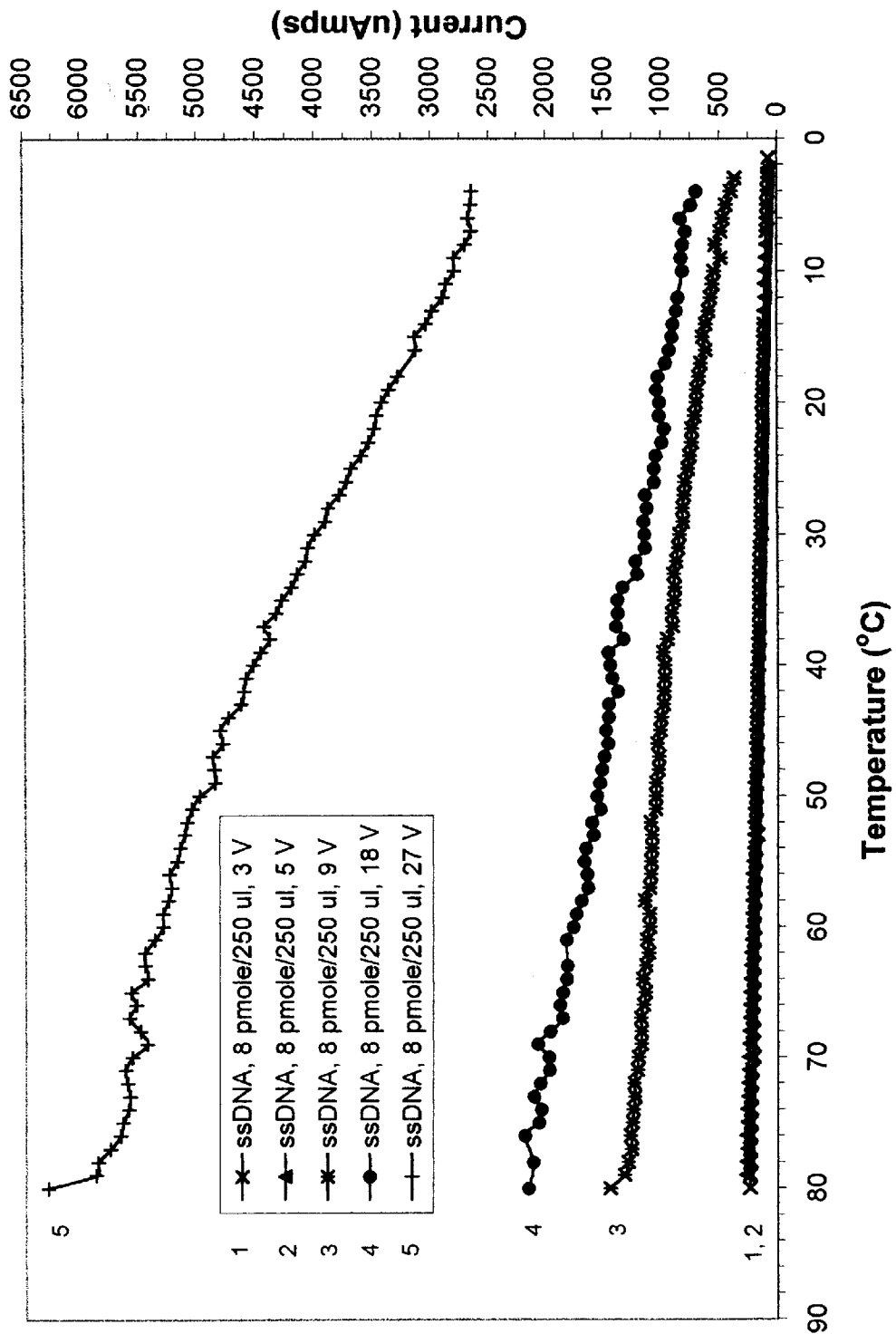
Fig. 13A. IPA of 15-mer ssDNA with decreasing temperature during different voltage applications

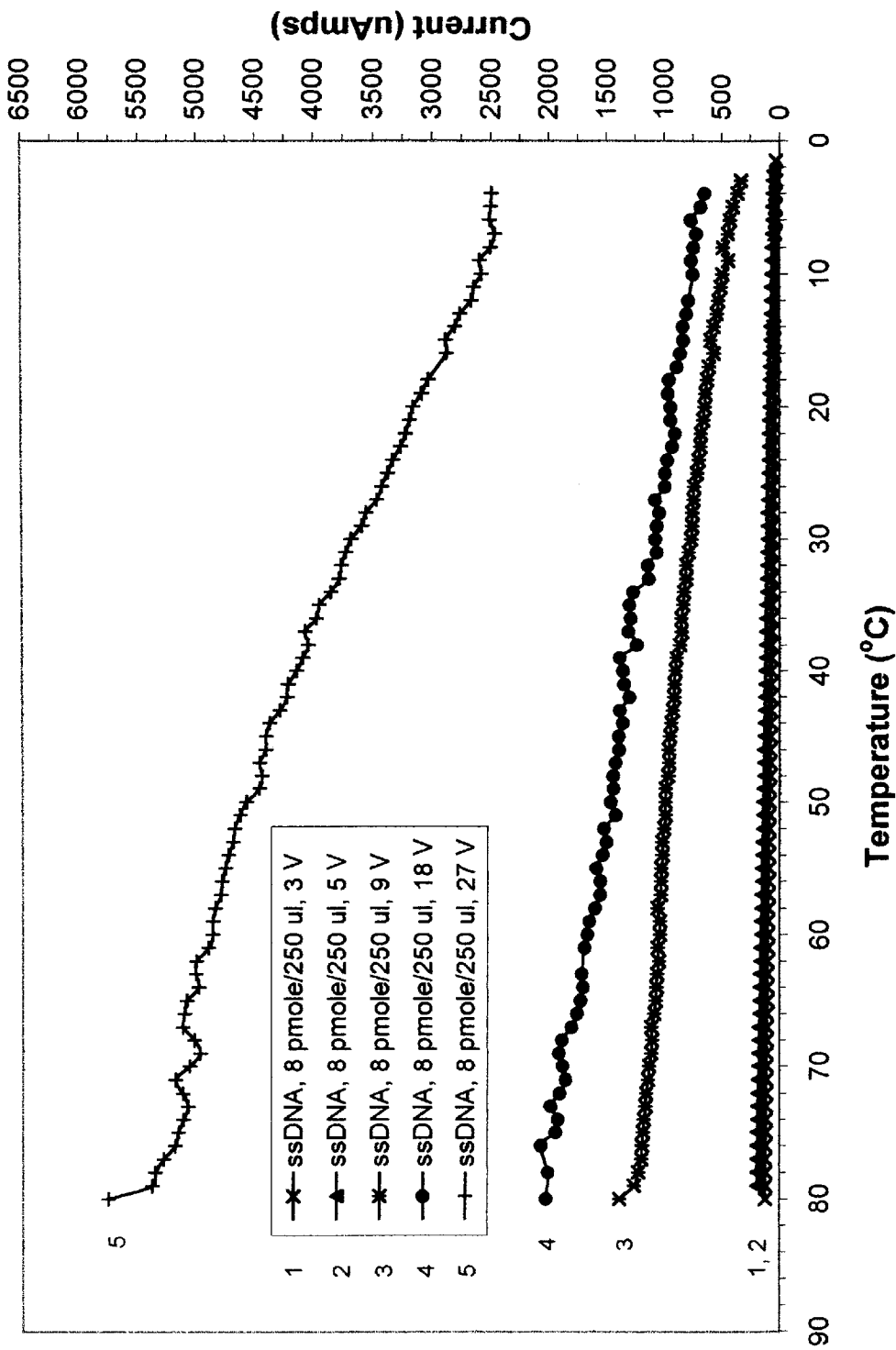
Fig. 13B. AA of 15-mer ssDNA with decreasing temperature during different voltage applications

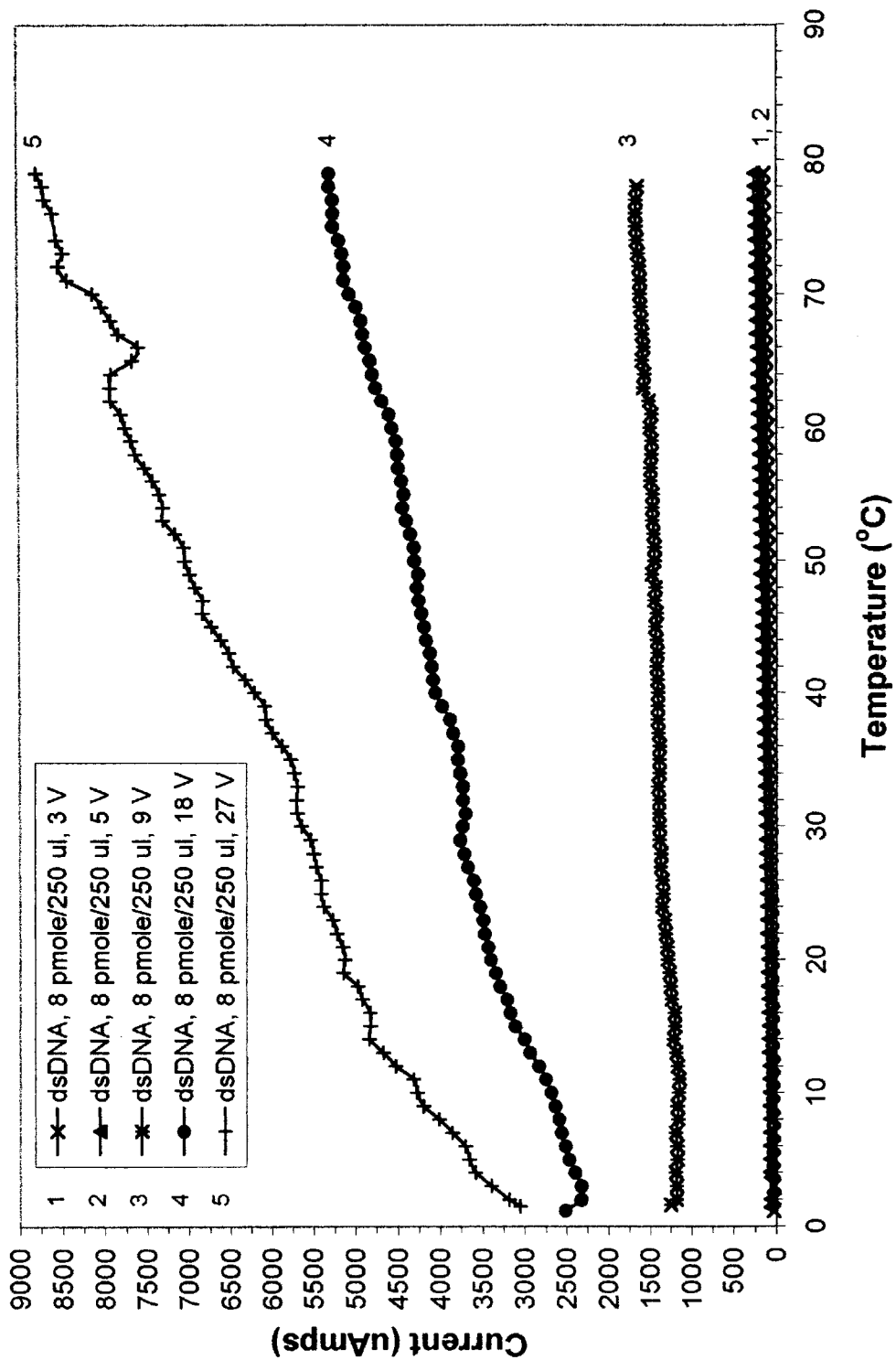

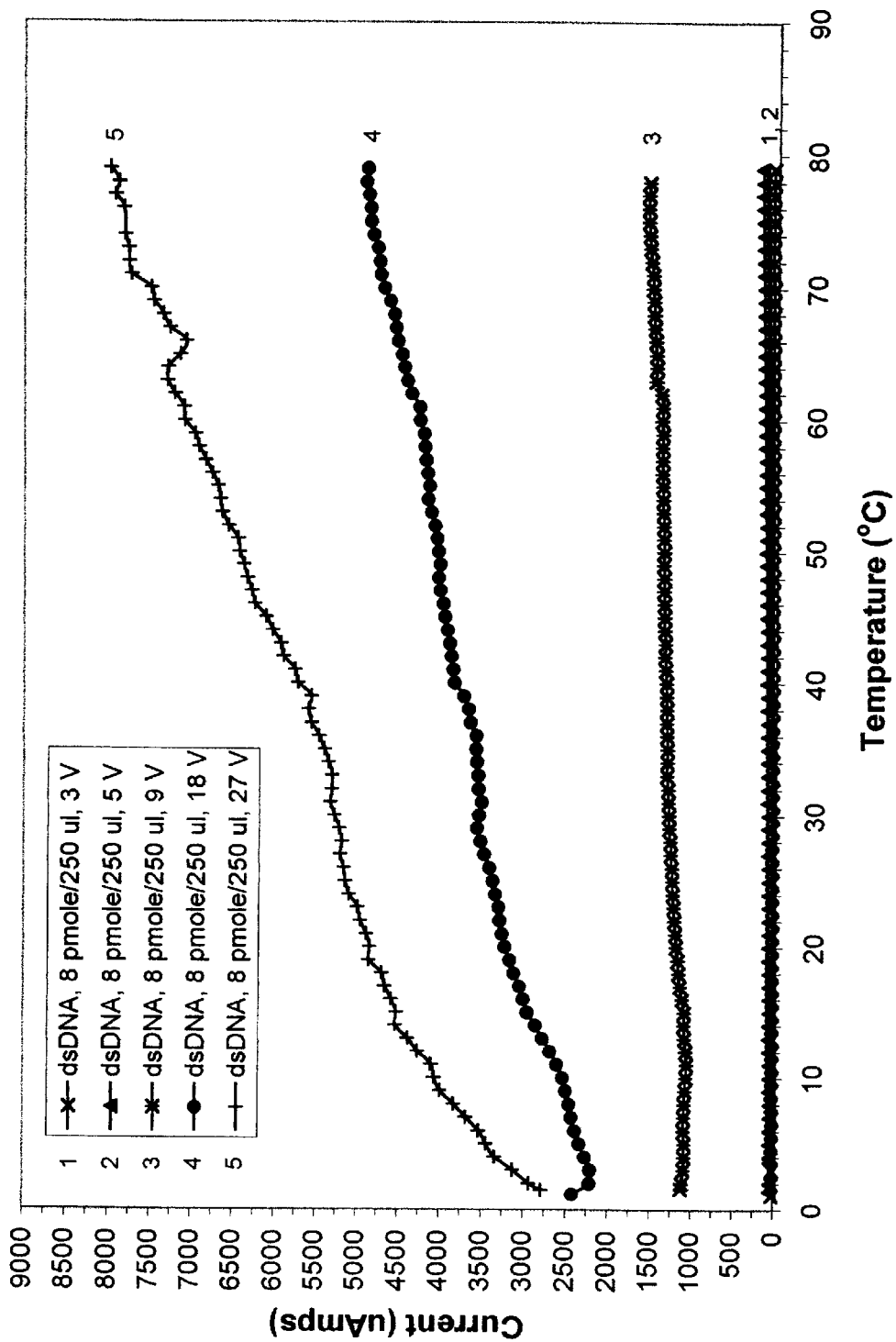
Fig. 14B. AA of 15-mer dsDNA with increasing temperature during different voltage applications

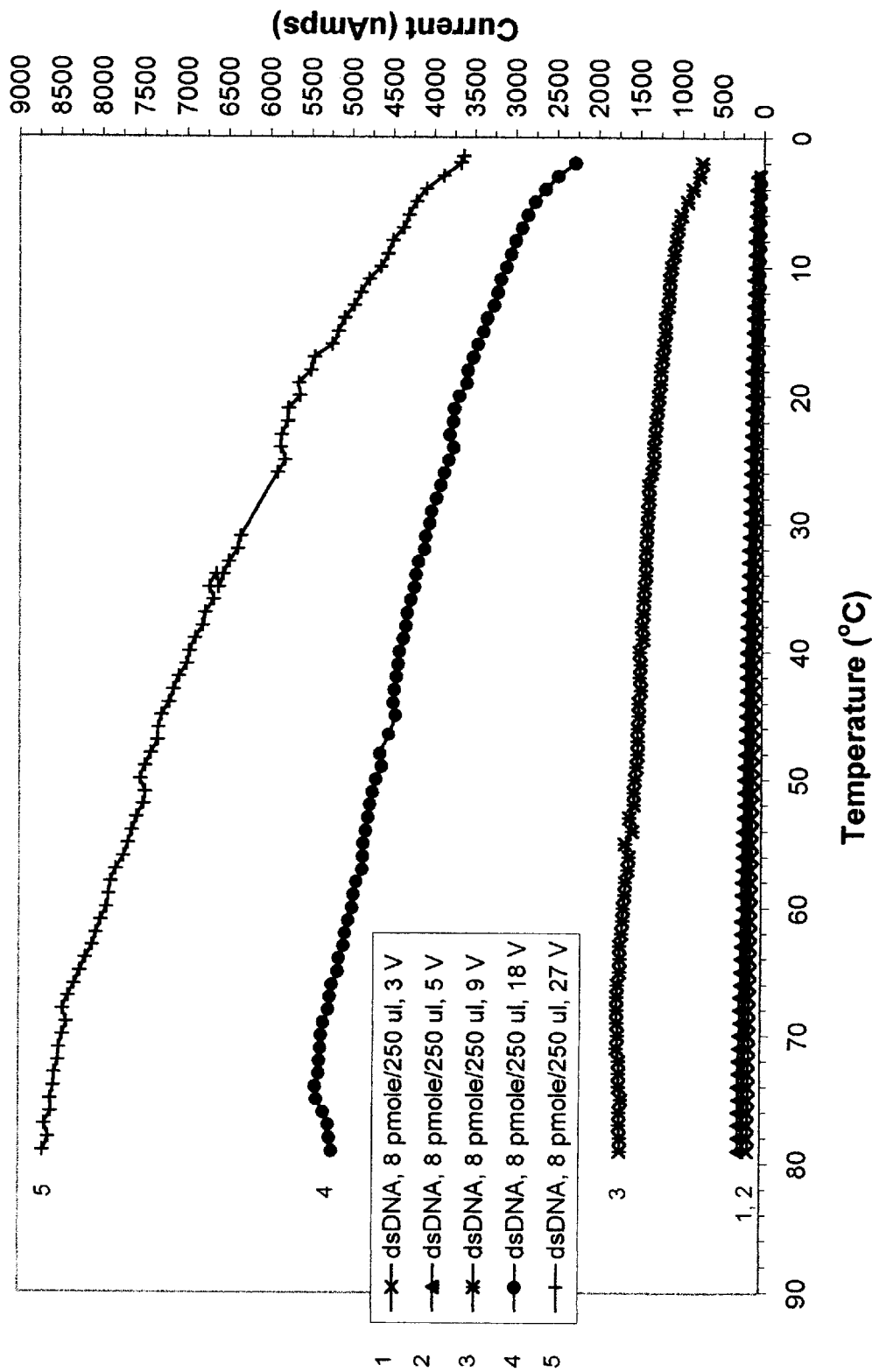
Fig. 15A. IPA of 15-mer dsDNA with decreasing temperature during different voltage applications

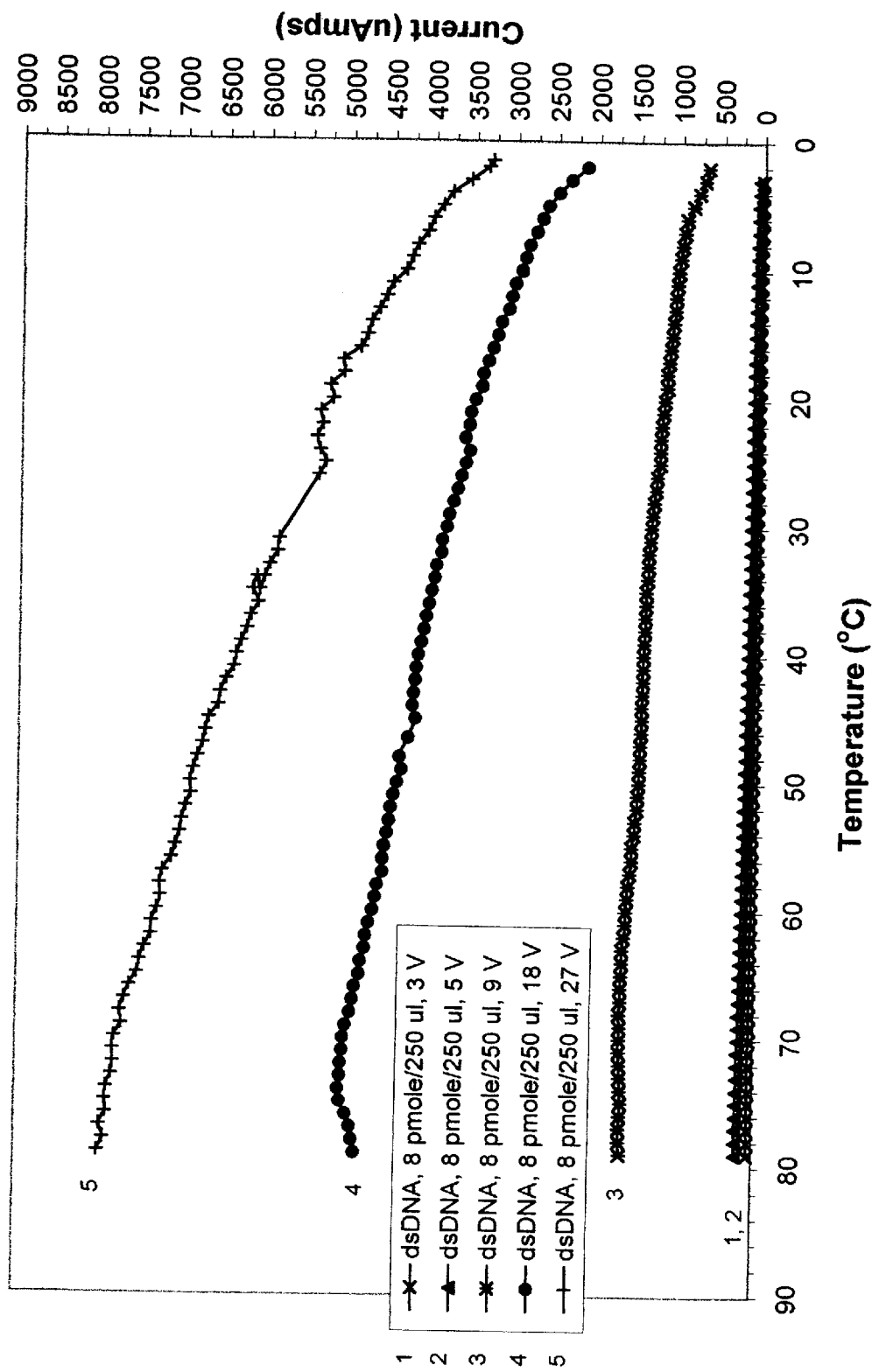
Fig. 15B. AA of 15-mer dsDNA with decreasing temperature during different voltage applications

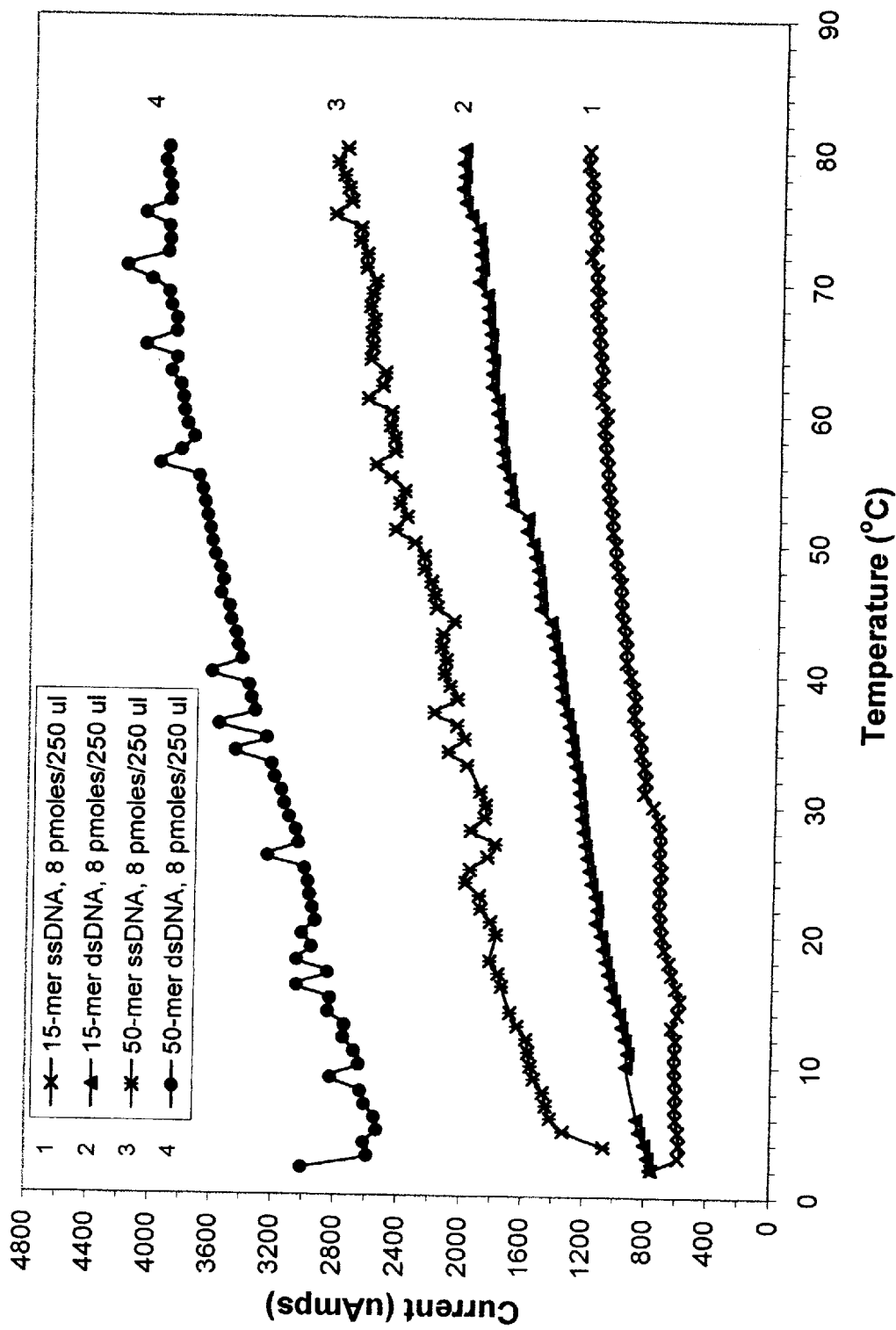
Fig. 16A. Comparison of IPA of 15-mer and 50-mer ssDNA, and 15-mer and 50-mer dsDNA during increasing temperature

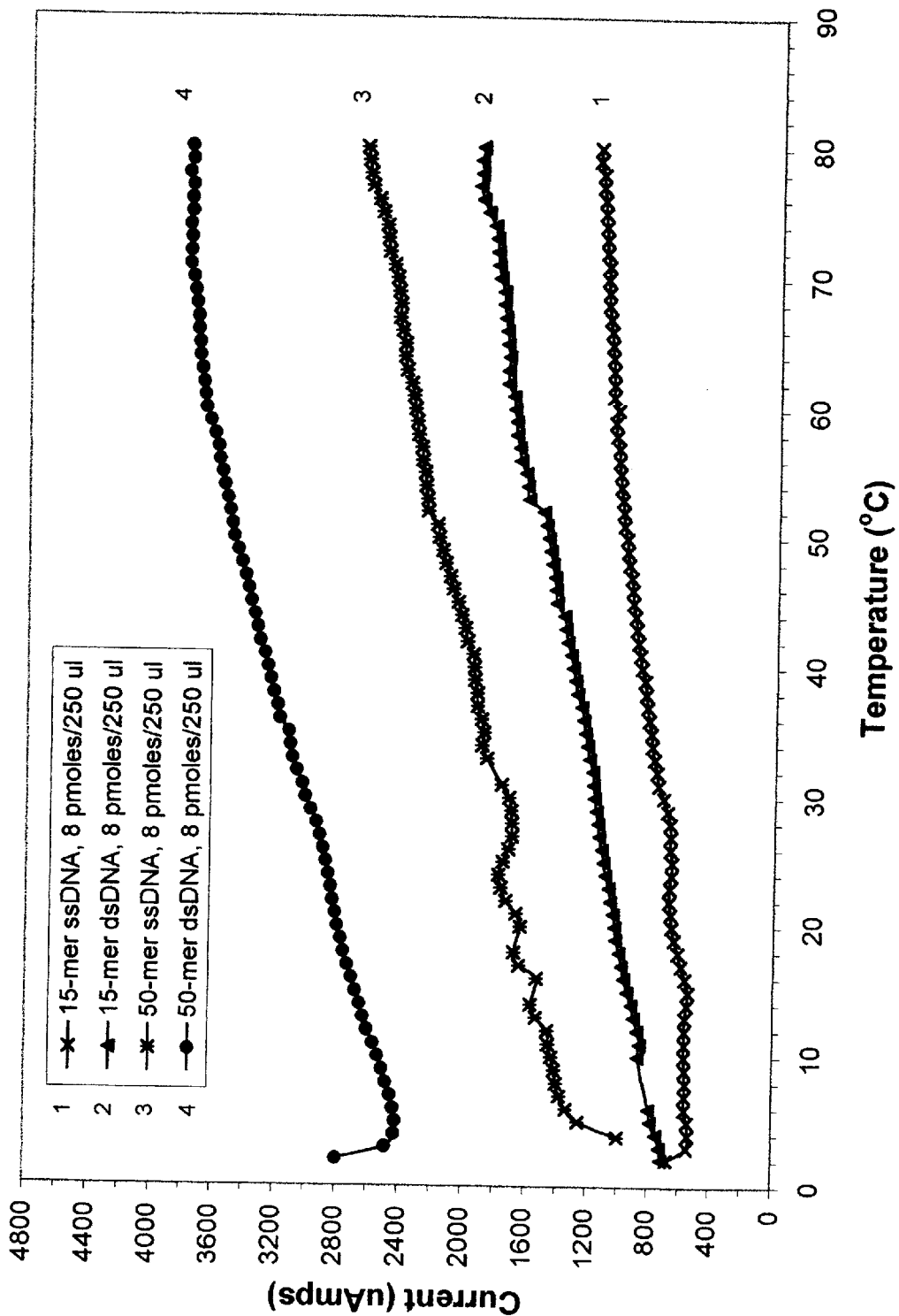
Fig. 16B. Comparison of AA of 15-mer and 50-mer ssDNA, and 15-mer and 50-mer dsDNA during increasing temperature

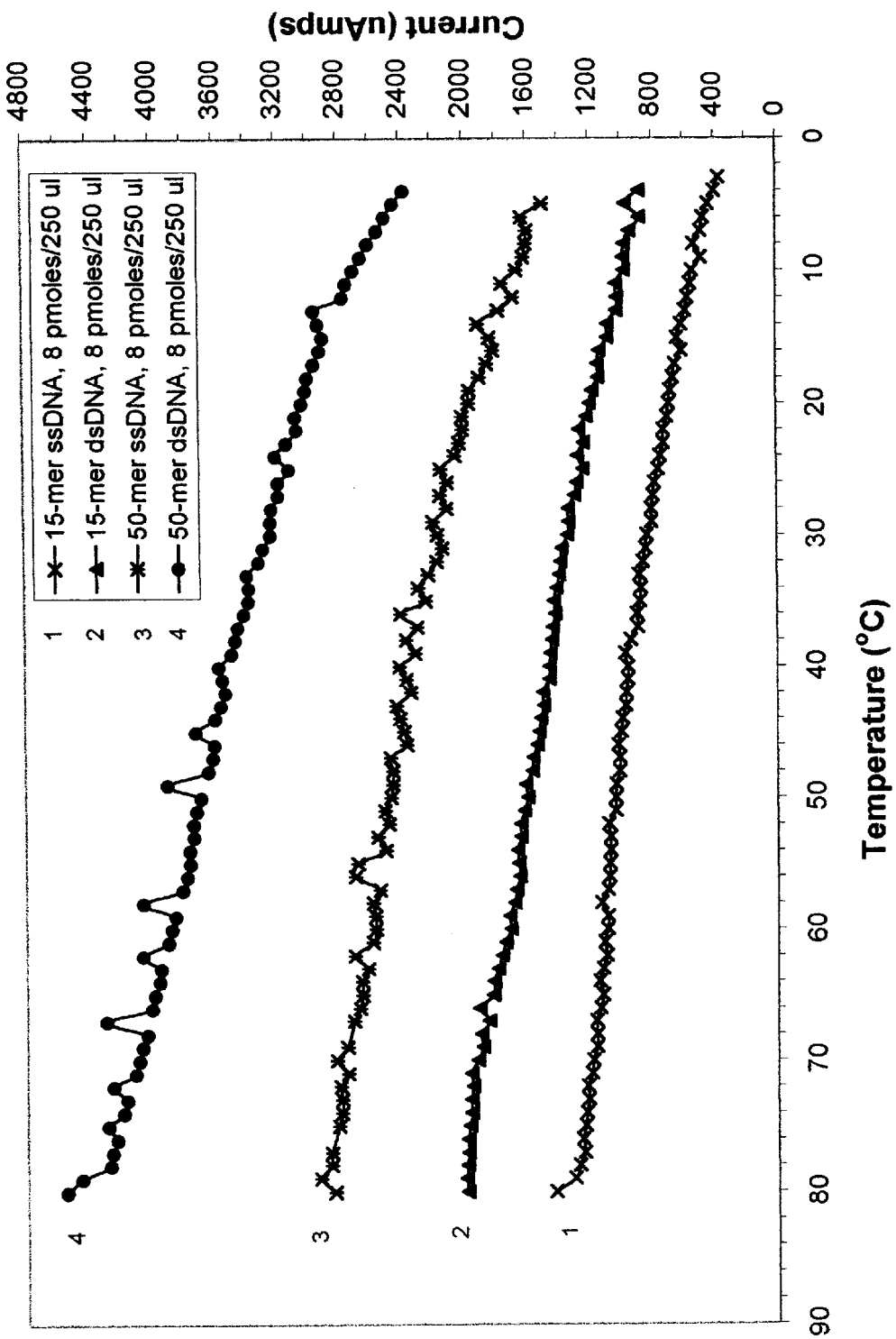
Fig. 17A. Comparison of IPA of 15-mer and 50-mer ssDNA, and 15-mer and 50-mer dsDNA during decreasing temperature

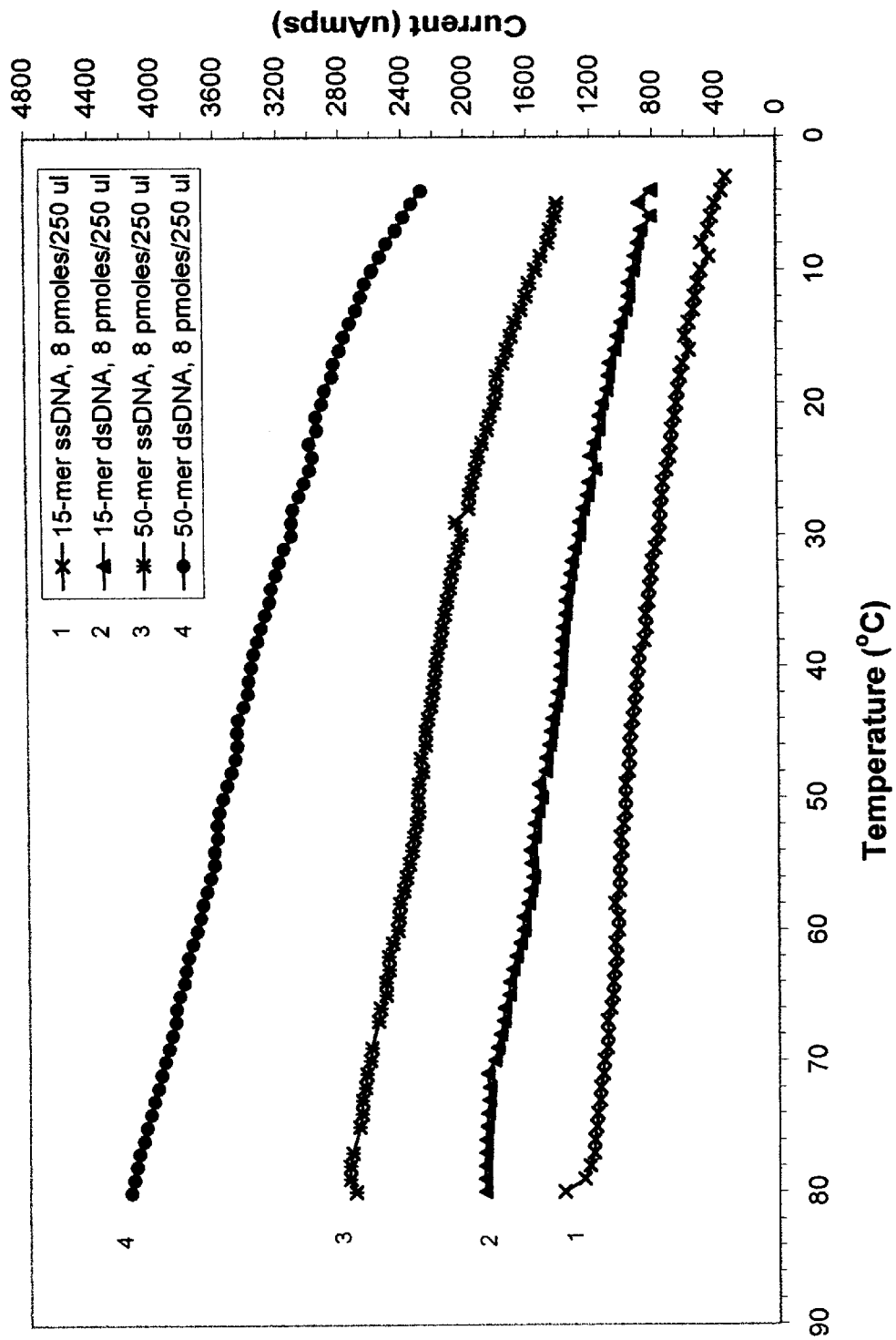
Fig. 17B. Comparison of AA of 15-mer and 50-mer ssDNA, and 15-mer and 50-mer dsDNA during decreasing temperature

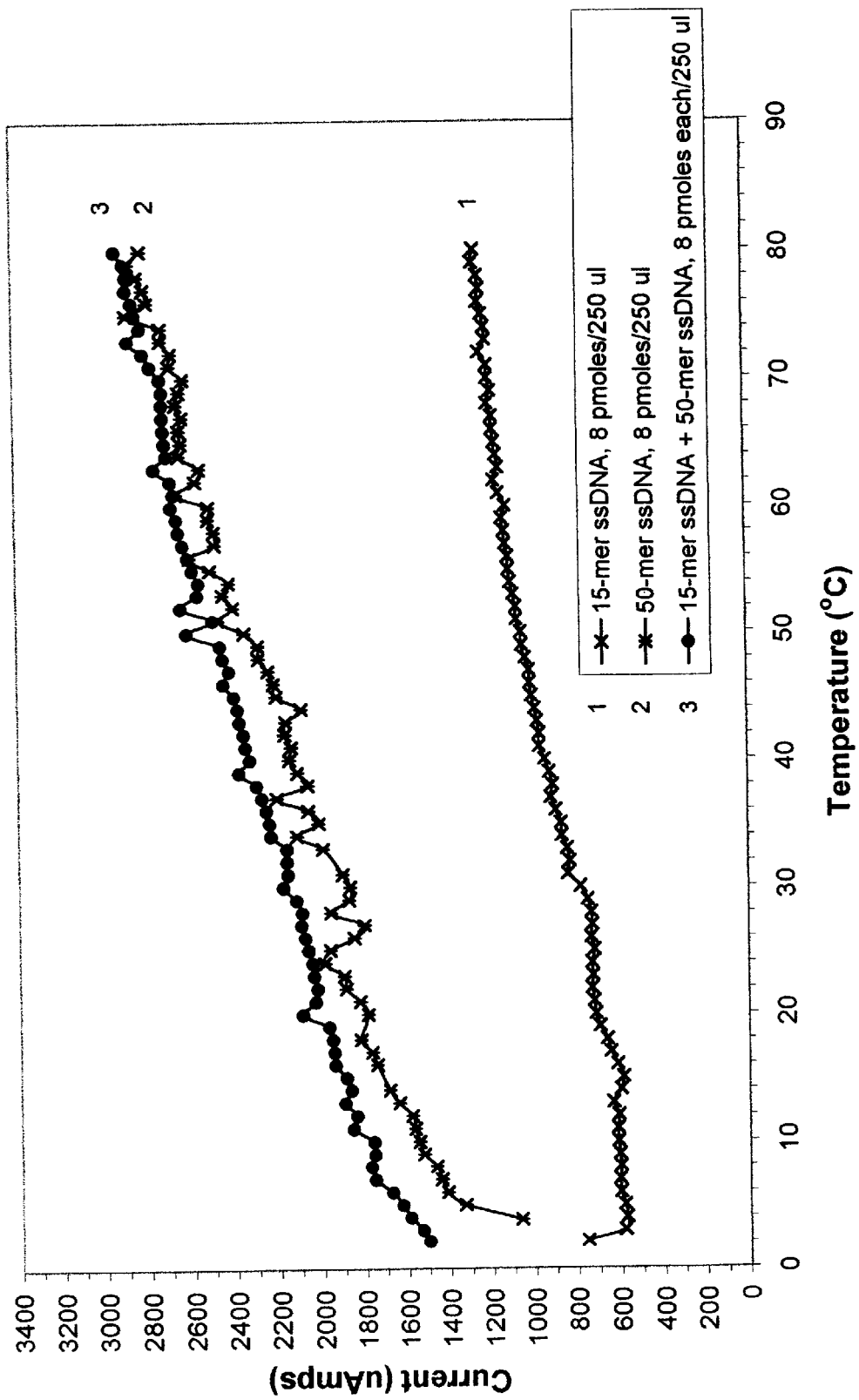
Fig. 18A. Comparison of IPA of 15-mer ssDNA and parallel homologous 50-mer ssDNA with increasing temperature

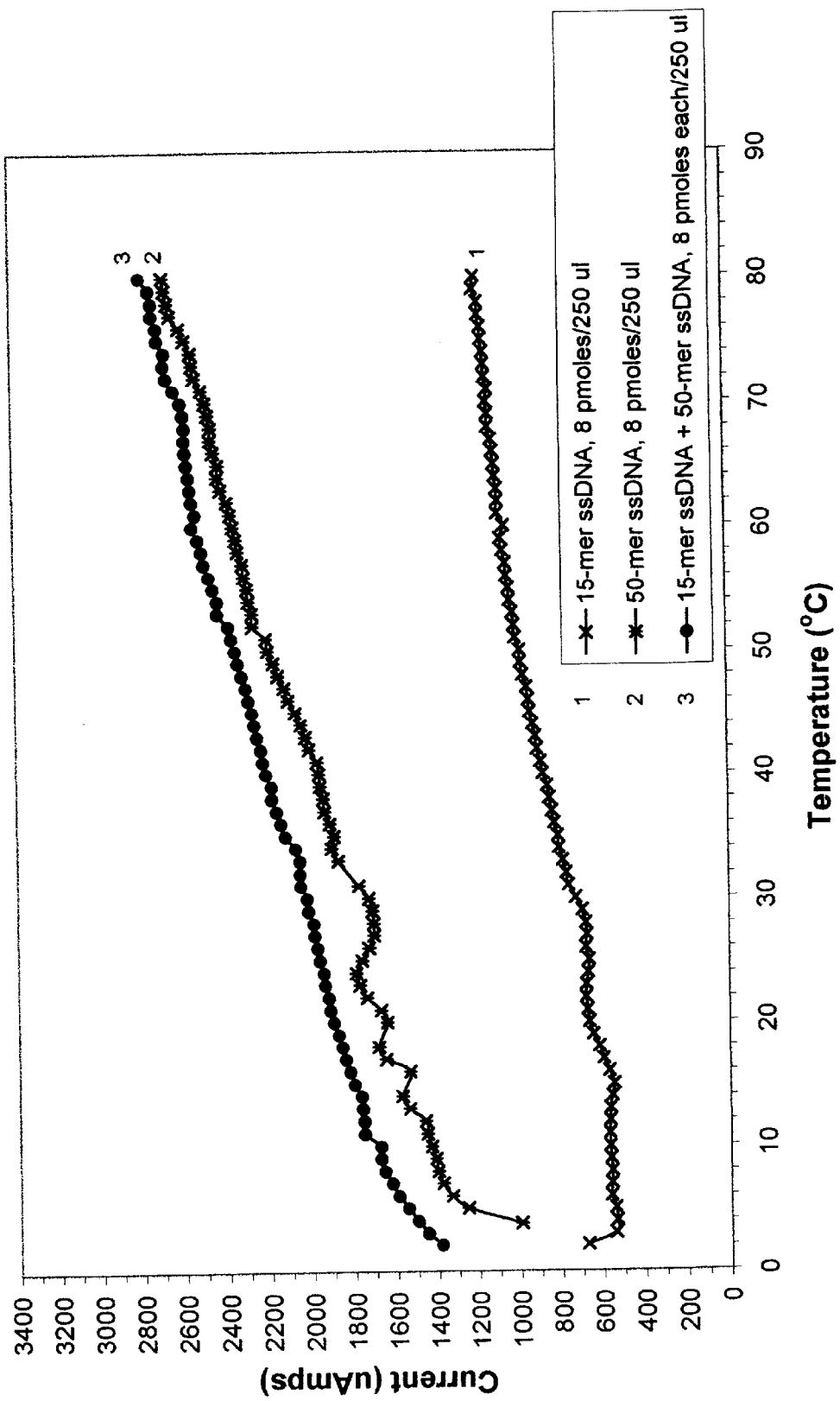

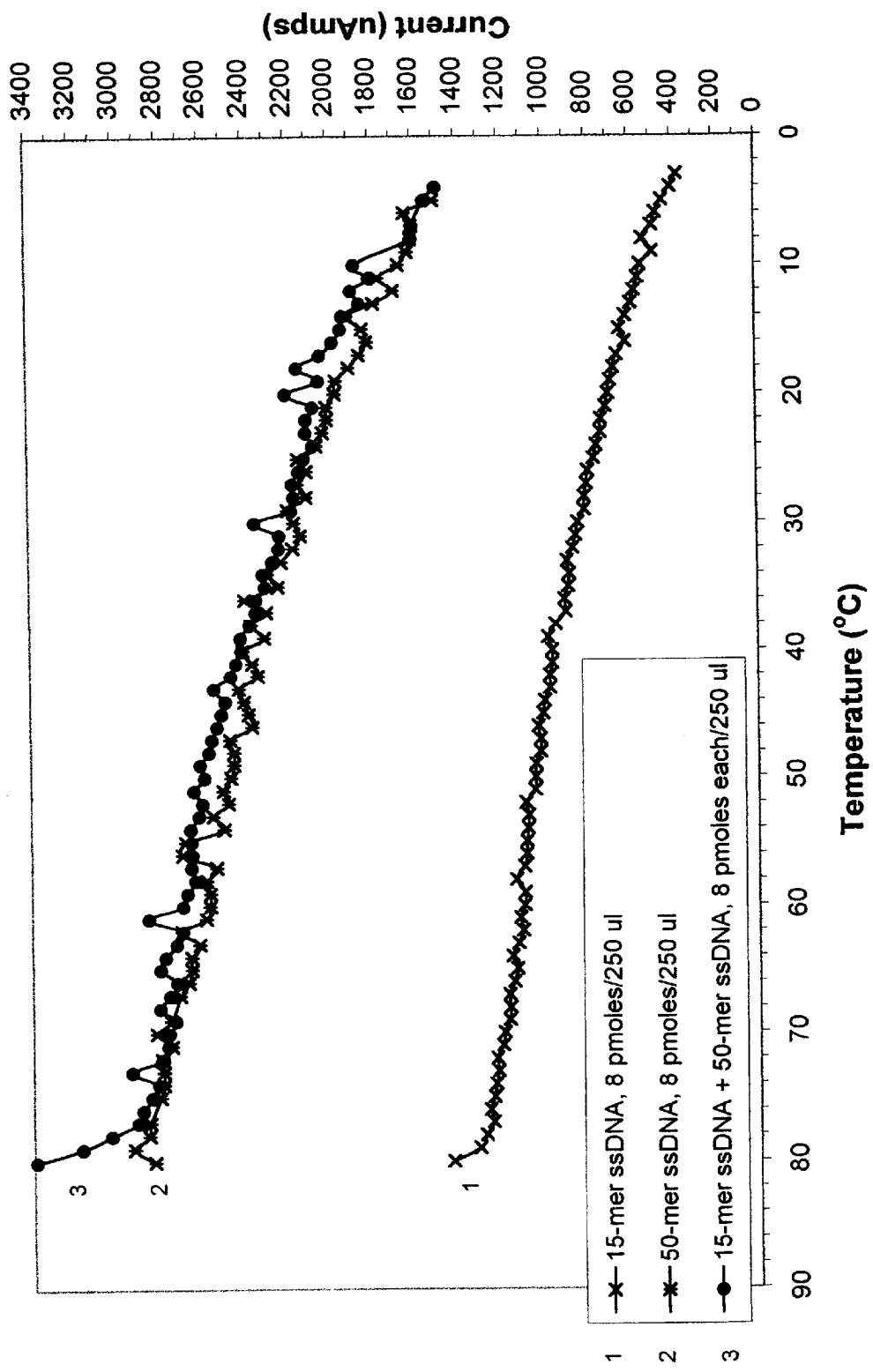
Fig. 19A. Comparison of IPA of 15-mer ssDNA and parallel homologous 50-mer ssDNA with decreasing temperature

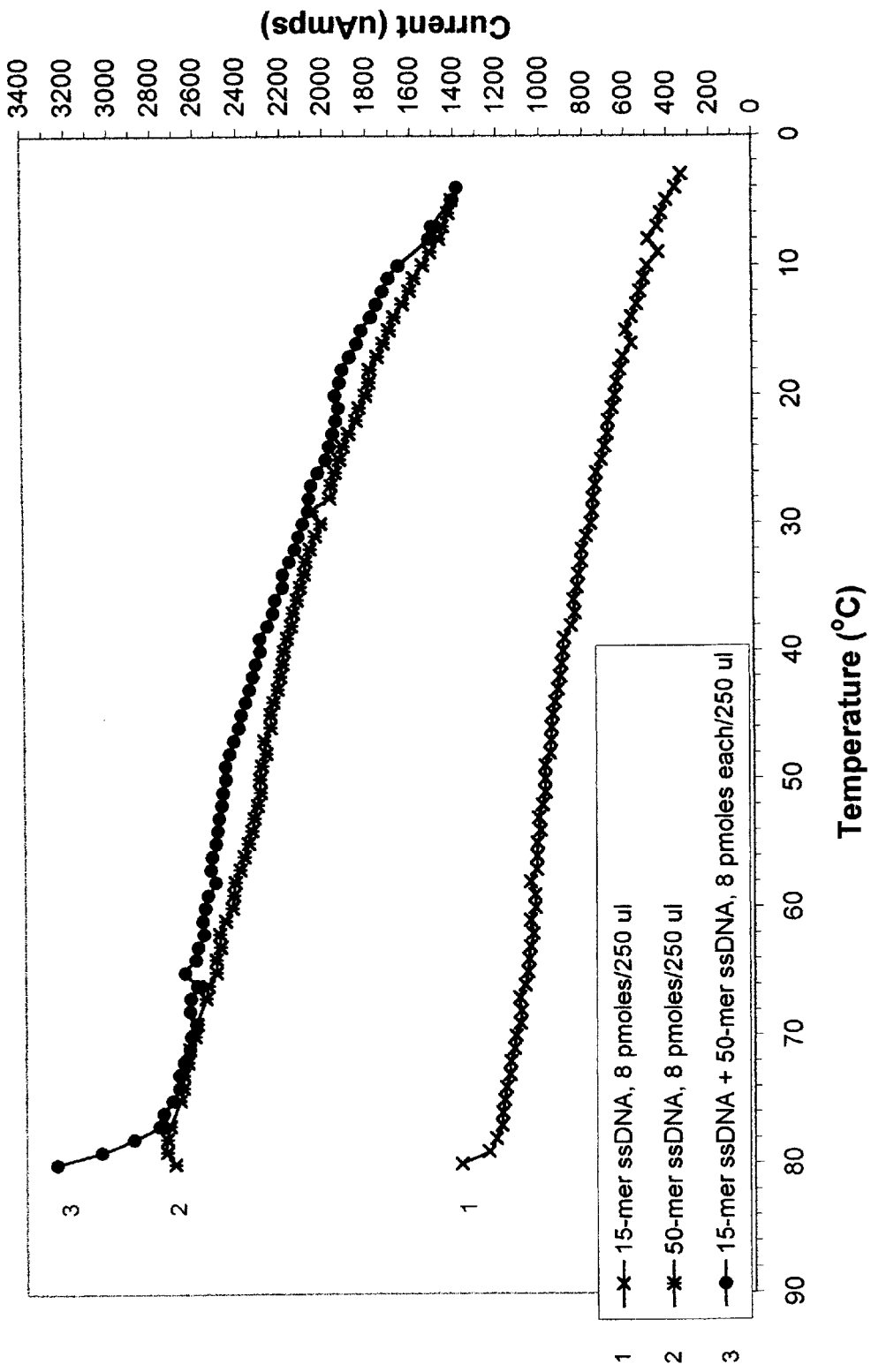
Fig. 19B. Comparison of AA of 15-mer ssDNA and parallel homologous 50-mer ssDNA with decreasing temperature

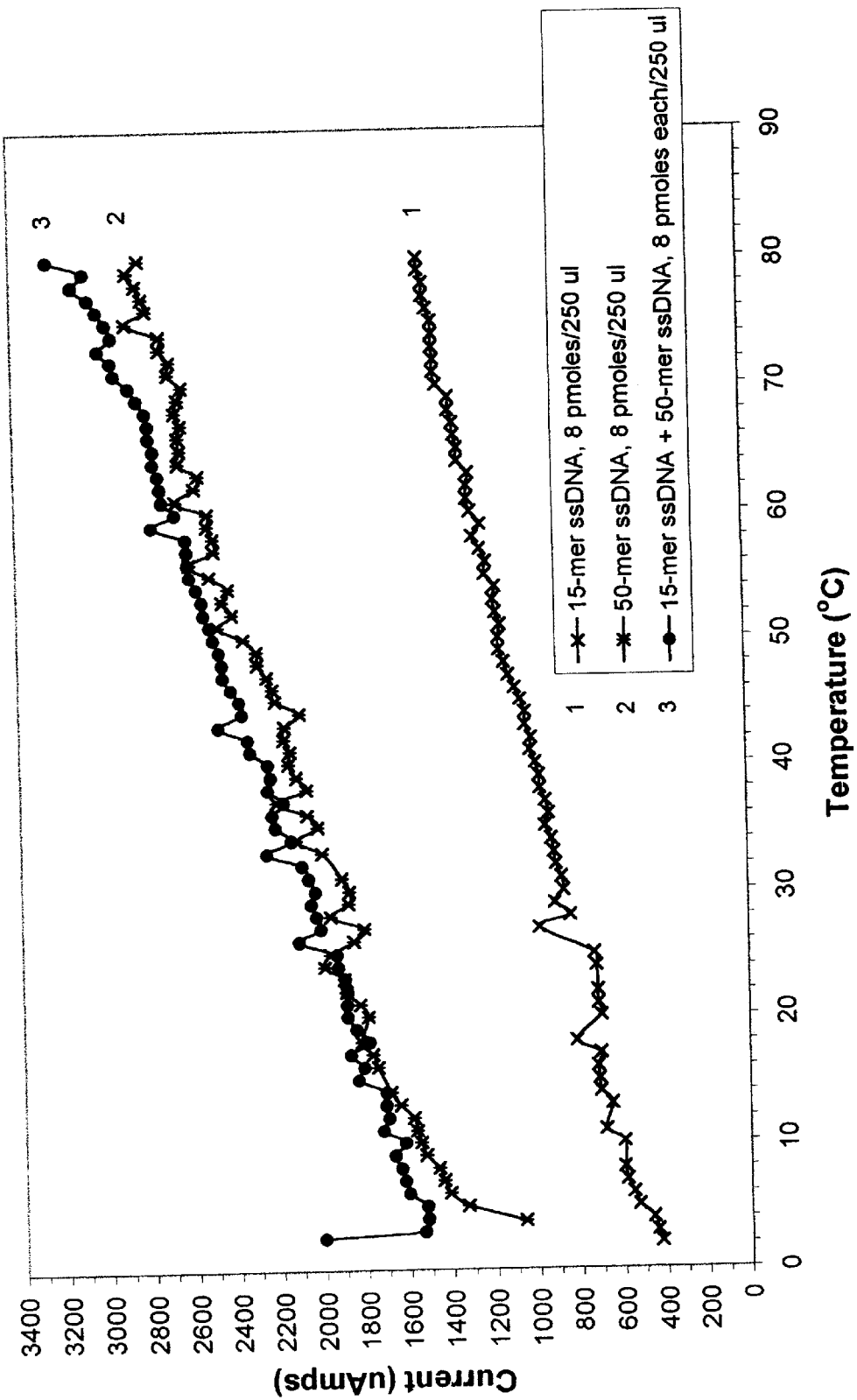
Fig. 20A. Comparison of IPA of 15-mer ssDNA and antiparallel complementary 50-mer ssDNA during increasing temperature

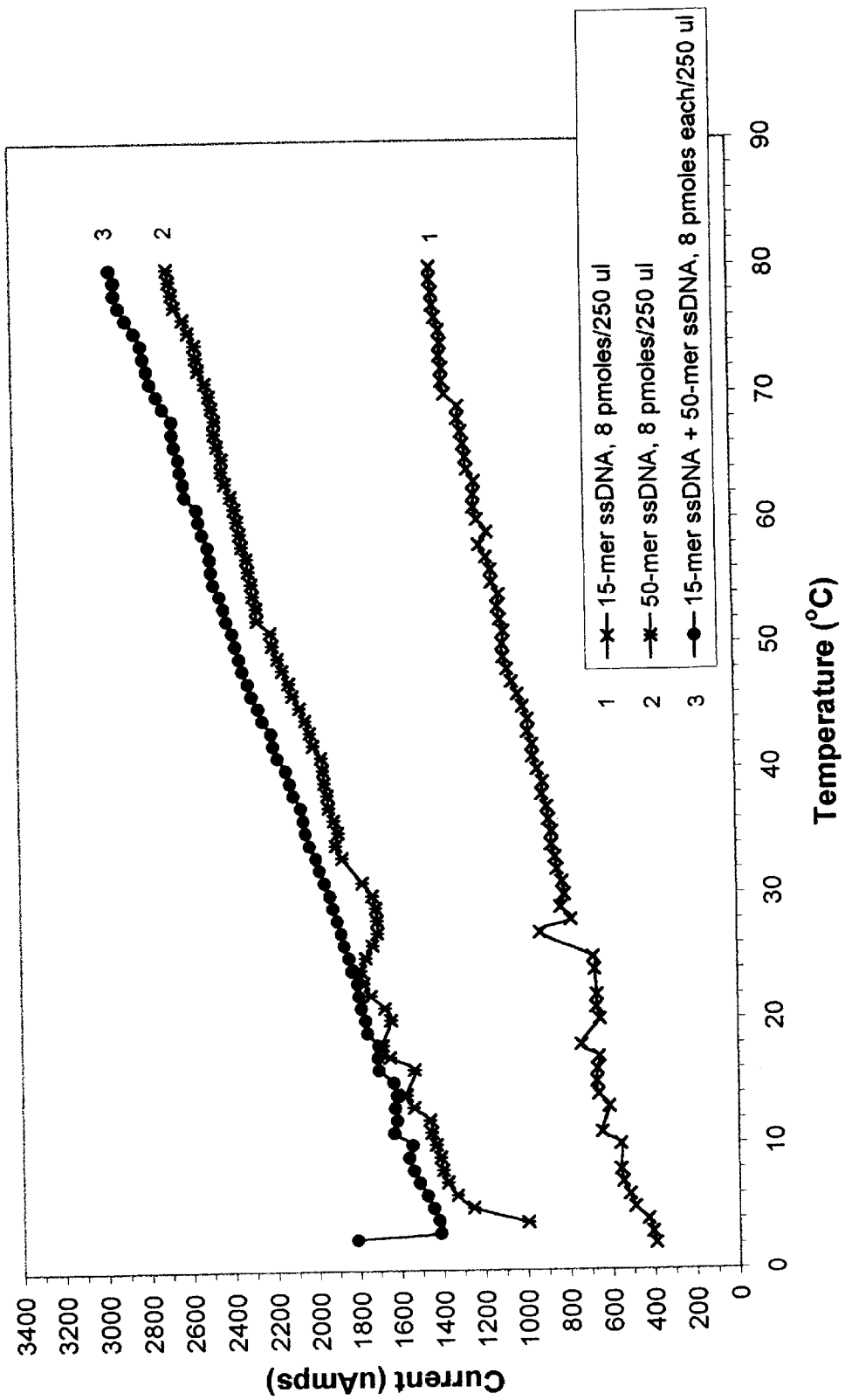

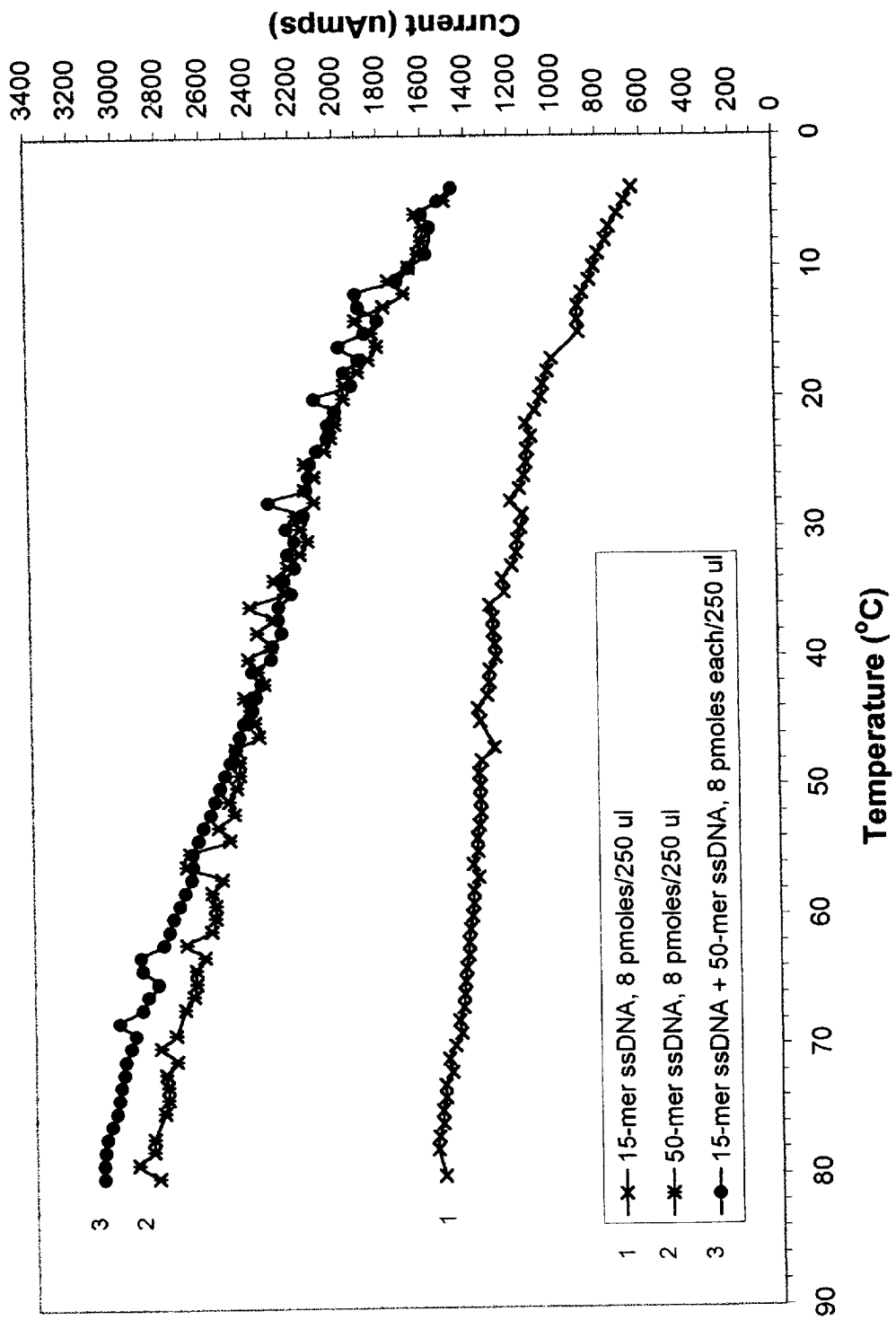
Fig. 21A. Comparison of IPA of 15-mer ssDNA and antiparallel complementary 50-mer ssDNA with decreasing temperature

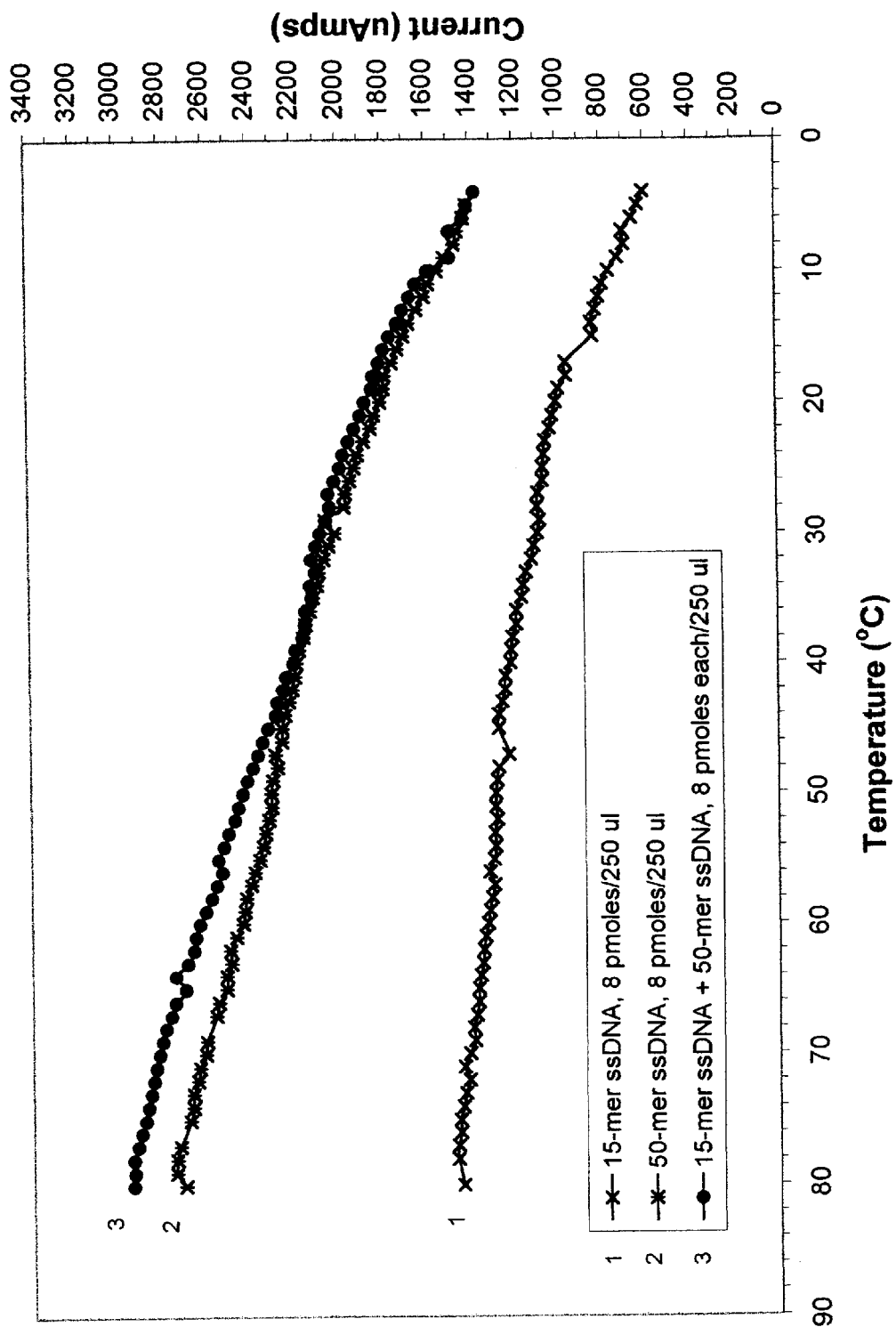
Fig. 21B. Comparison of AA of 15-mer ssDNA and antiparallel complementary 50-mer ssDNA with decreasing temperature

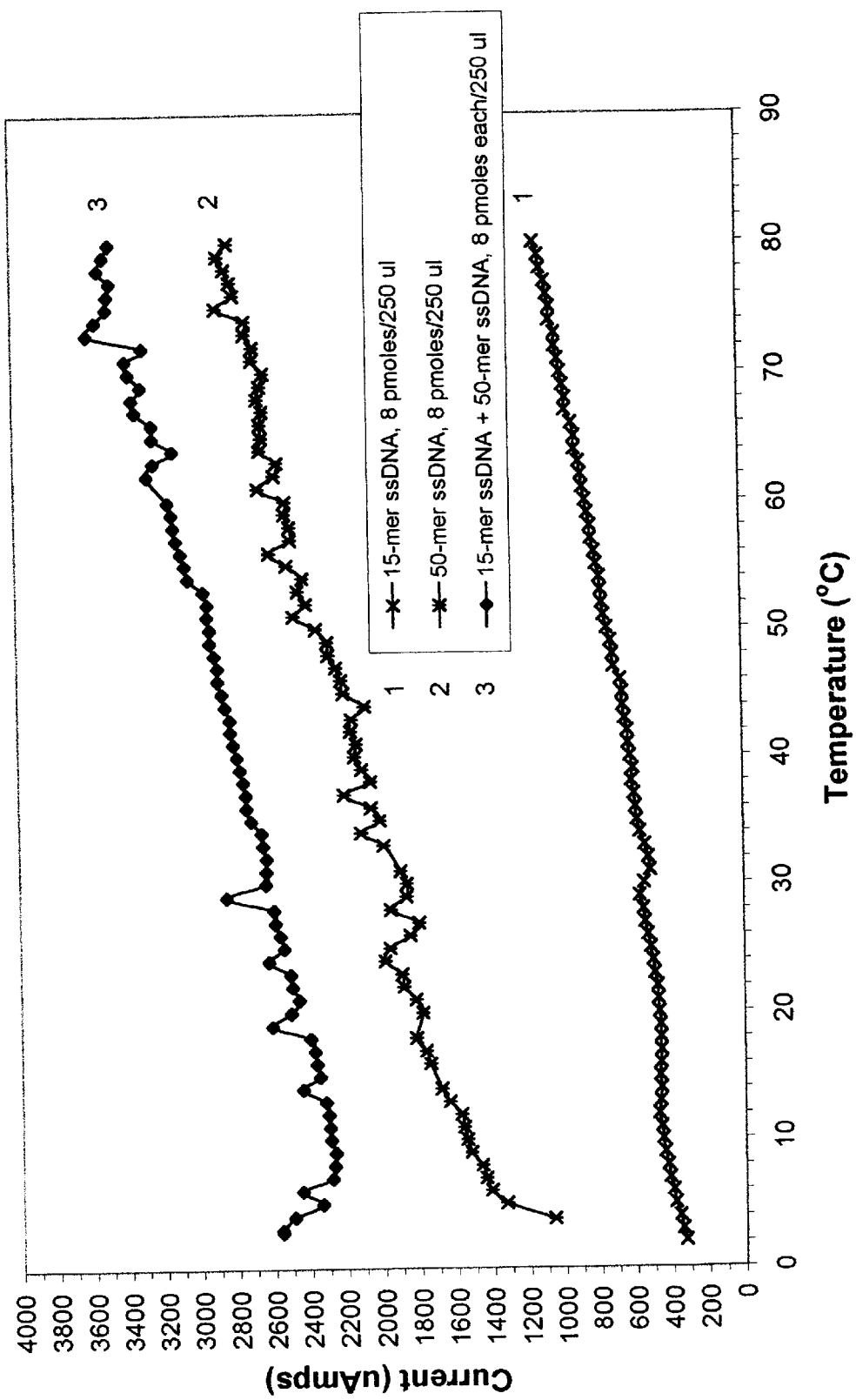
Fig. 22A. Comparison of IPA of 15-mer ssDNA and unrelated 50-mer ssDNA during increasing temperature

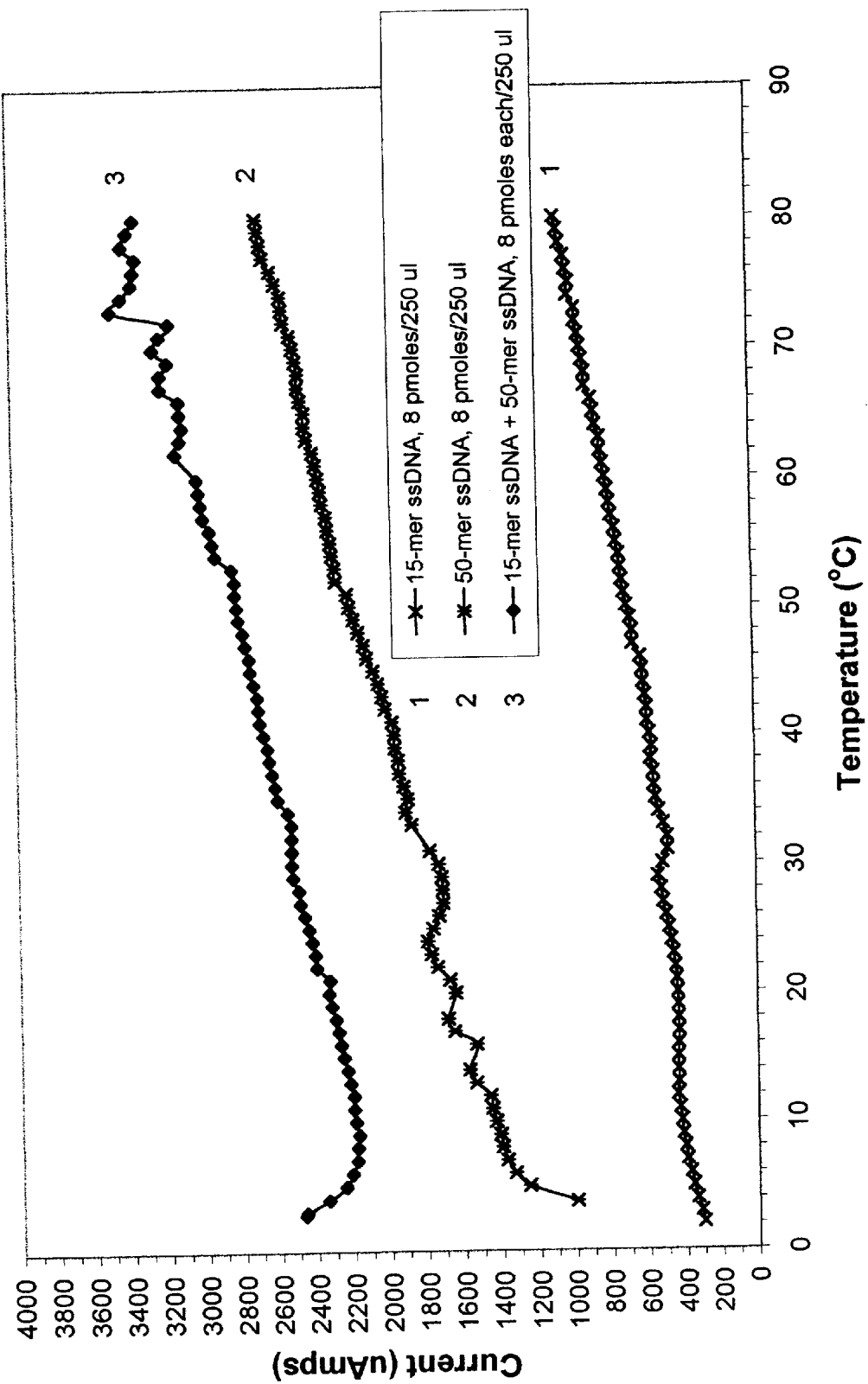

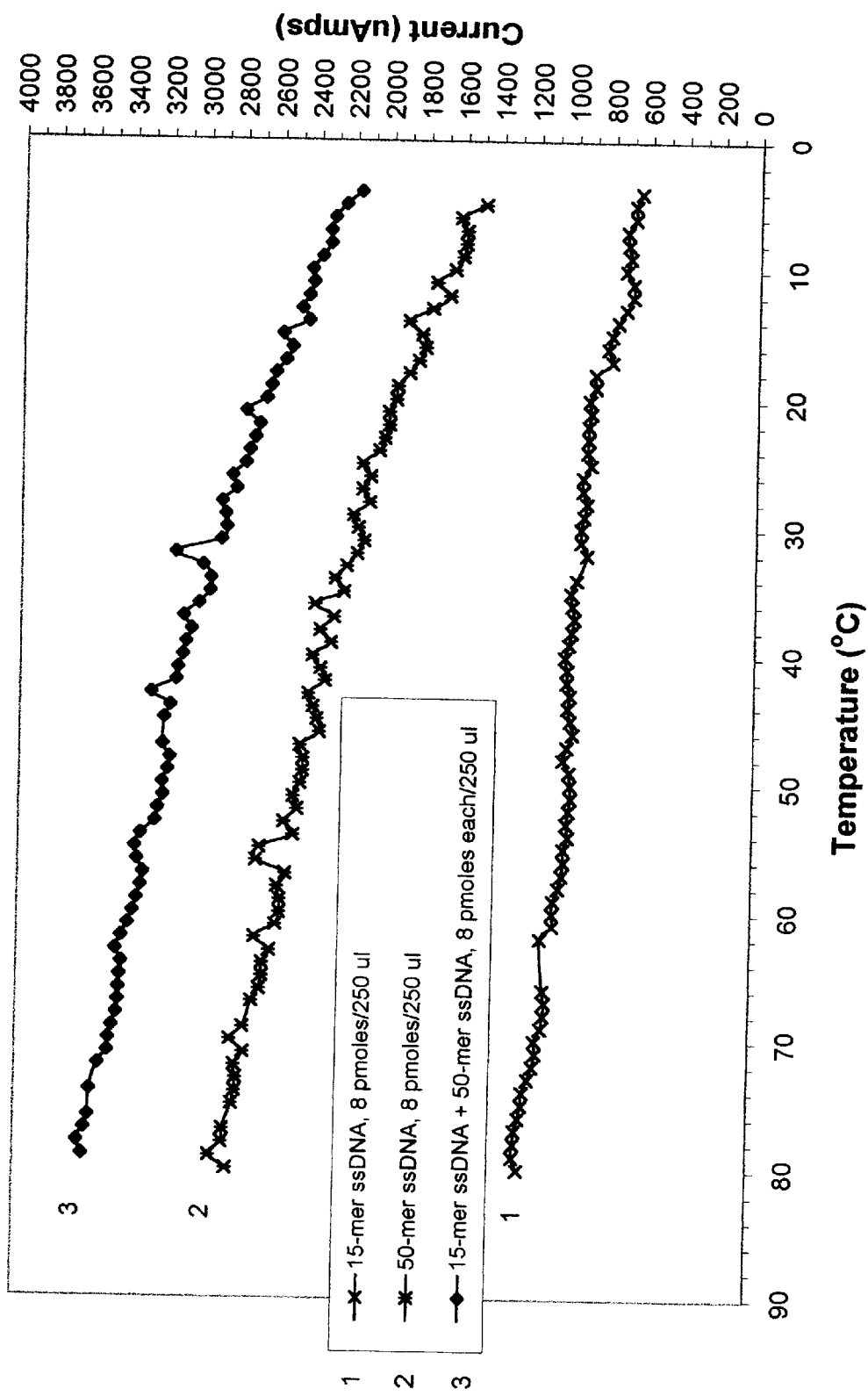
Fig. 23A. Comparison of IPA of 15-mer ssDNA and unrelated 50-mer ssDNA during decreasing temperature

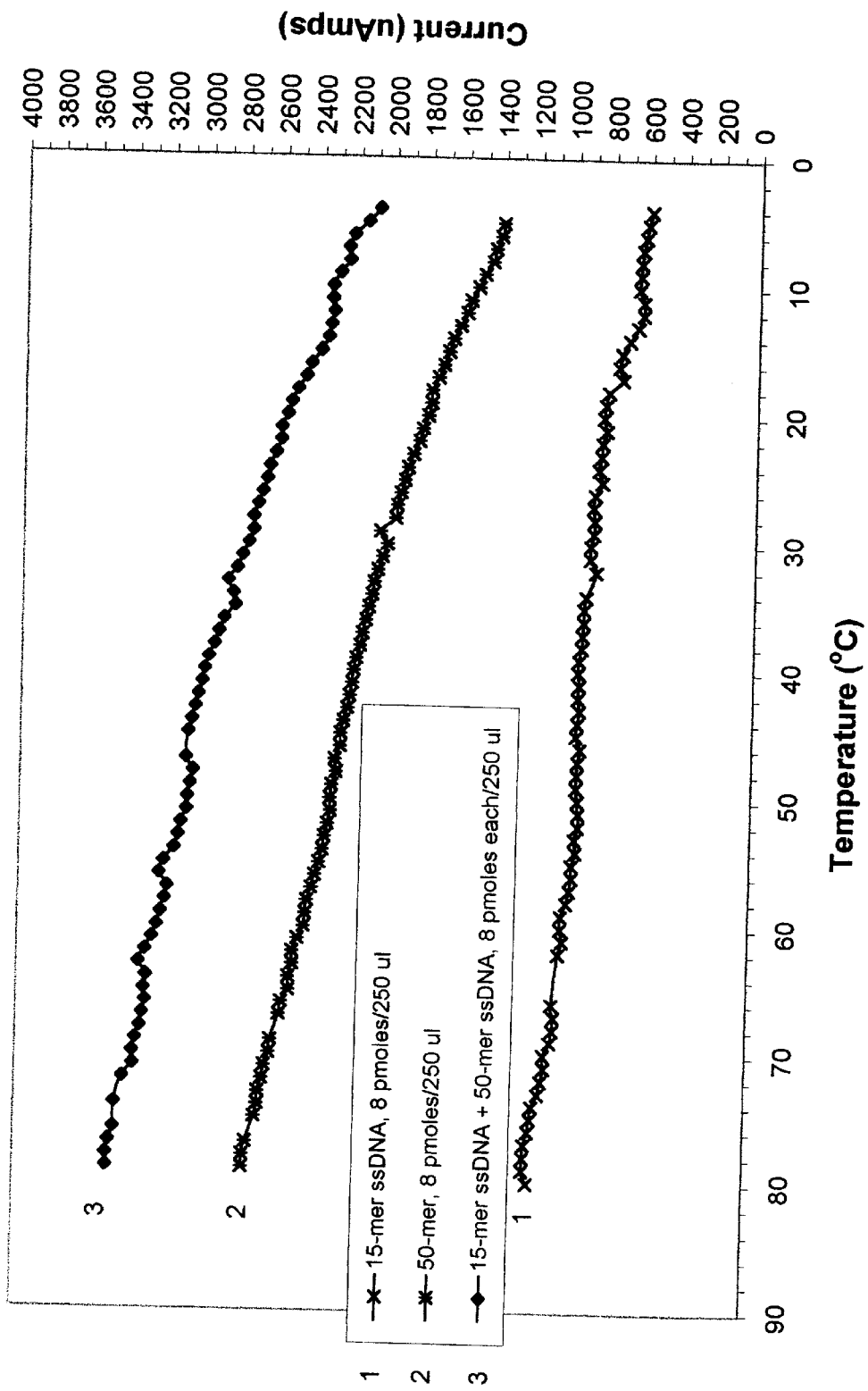
Fig. 23B. Comparison of AA of 15-mer ssDNA and unrelated 50-mer ssDNA during decreasing temperature

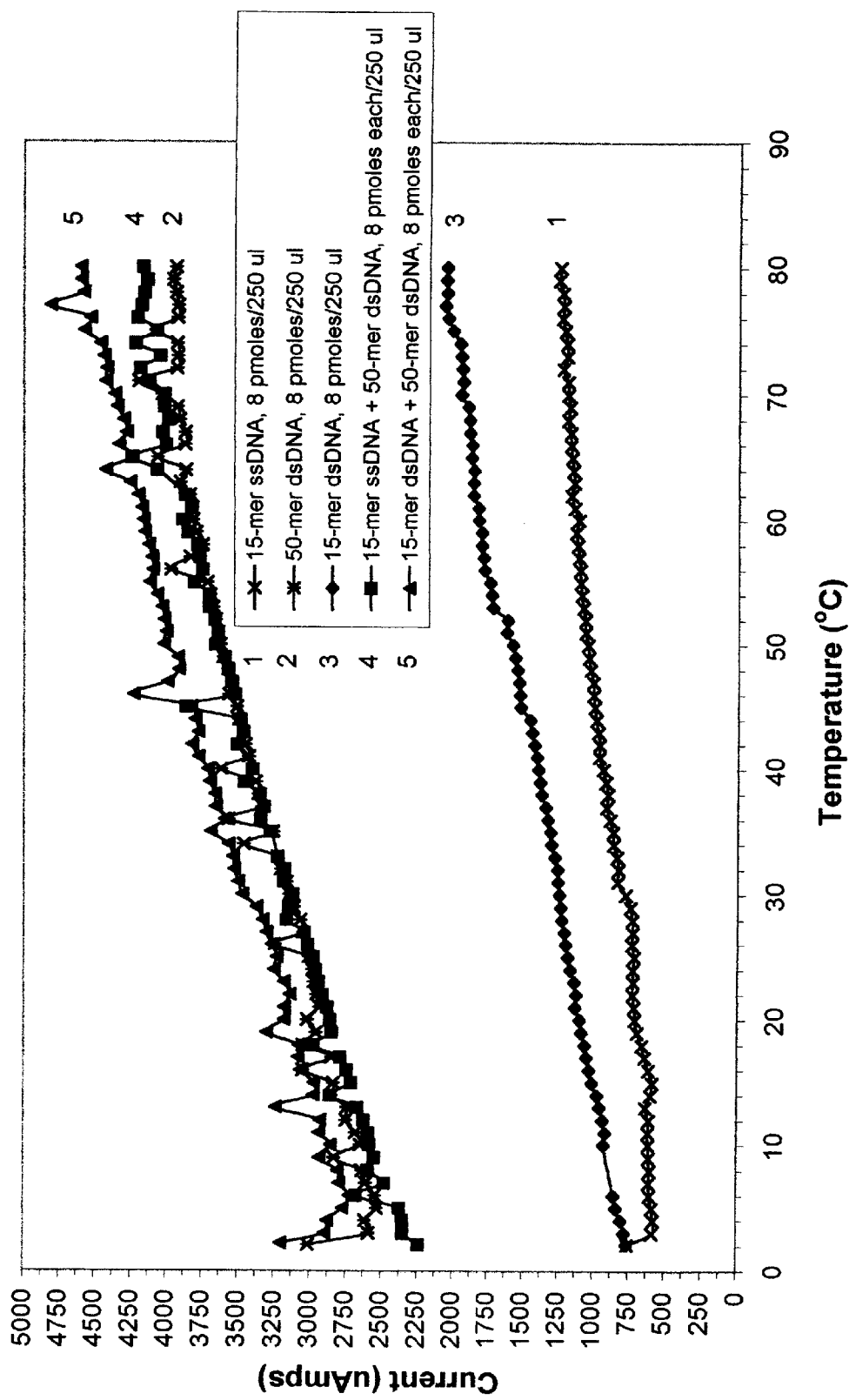
Fig. 24A. Comparison of IPA of mixes of 50-mer dsDNA with antiparallel complementary 15-mer ssDNA or with parallel homologous 15-mer dsDNA during increasing temperature

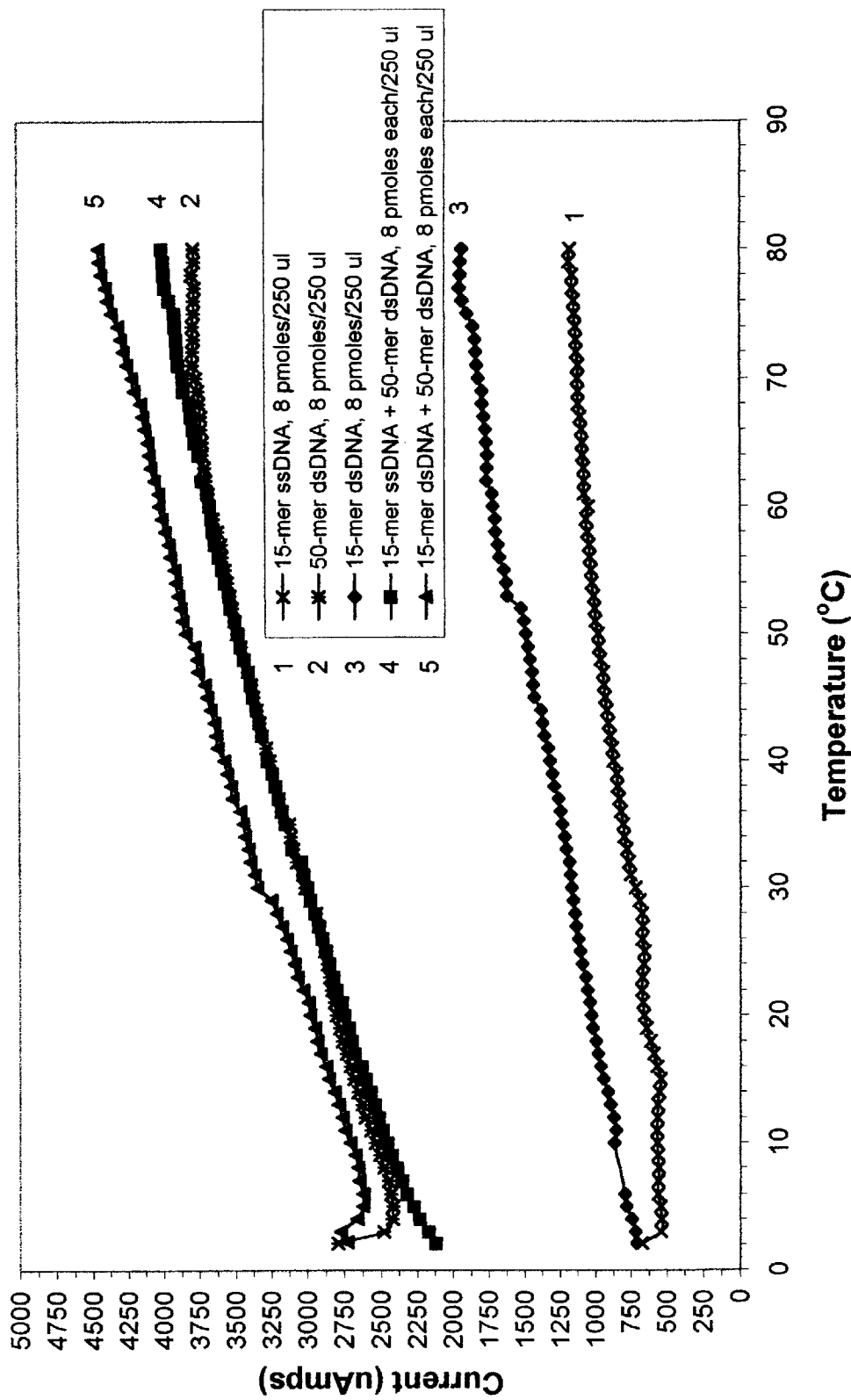
Fig. 24B. Comparison of AA of mixes of 50-mer dsDNA with antiparallel complementary 15-mer ssDNA or with parallel homologous 15-mer dsDNA during increasing temperature

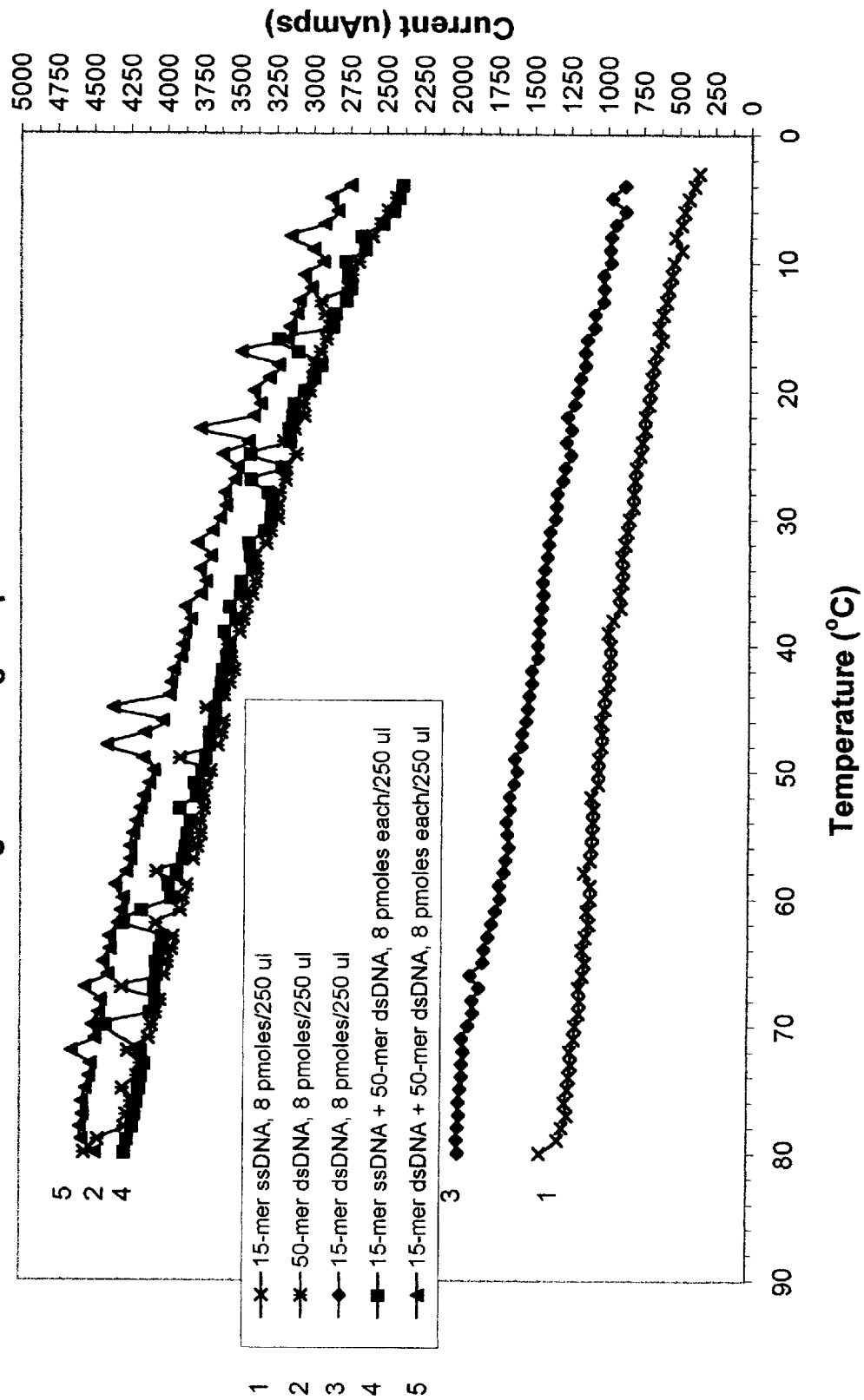
Fig. 25A. Comparison of IPA of mixes of 50-mer dsDNA with antiparallel complementary 15-mer ssDNA or with parallel homologous 15-mer dsDNA during decreasing temperature

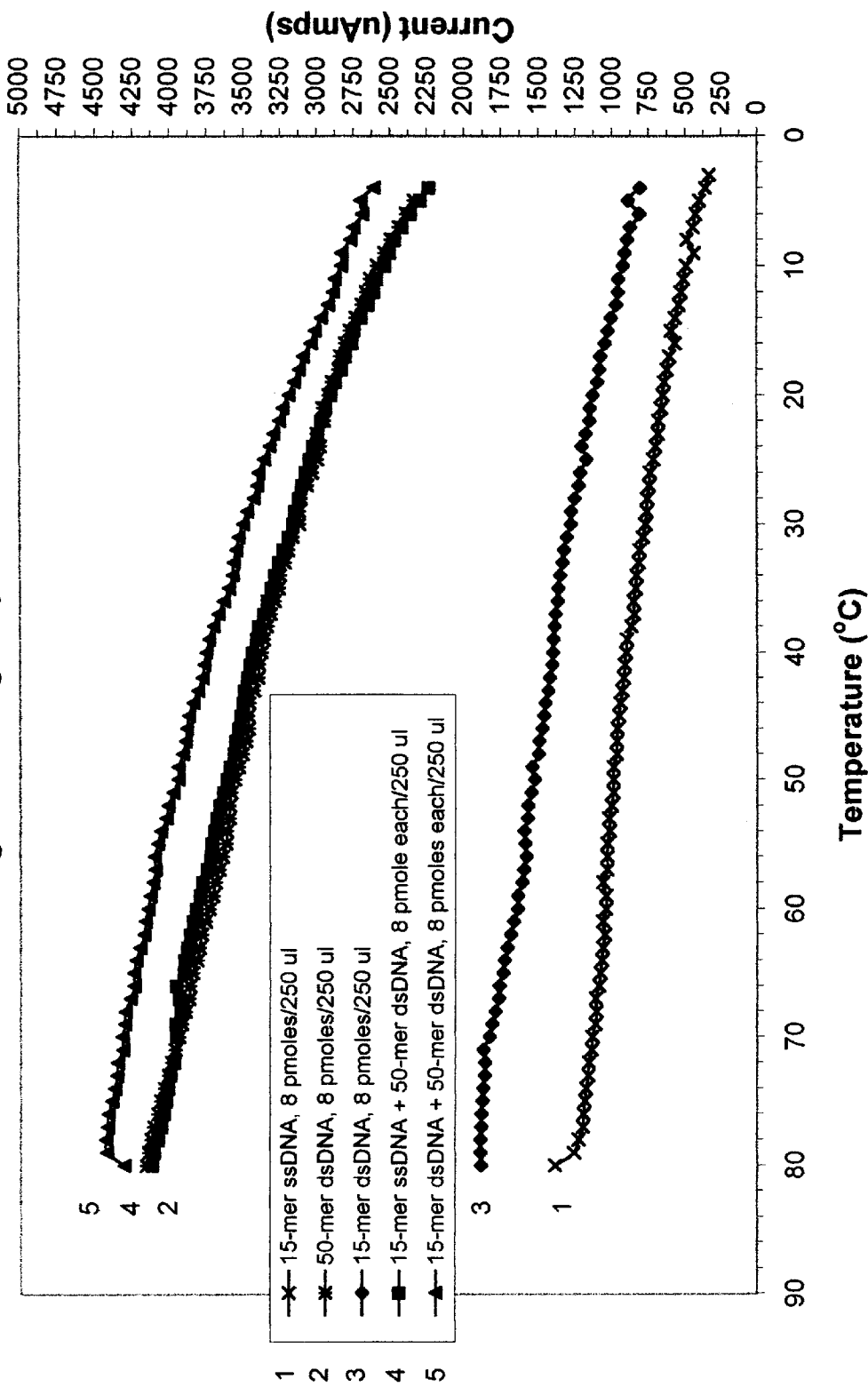
Fig. 25B. Comparison of AA of mixes of 50-mer dsDNA with antiparallel complementary 15-mer ssDNA or with parallel homologous 15-mer dsDNA during decreasing temperature

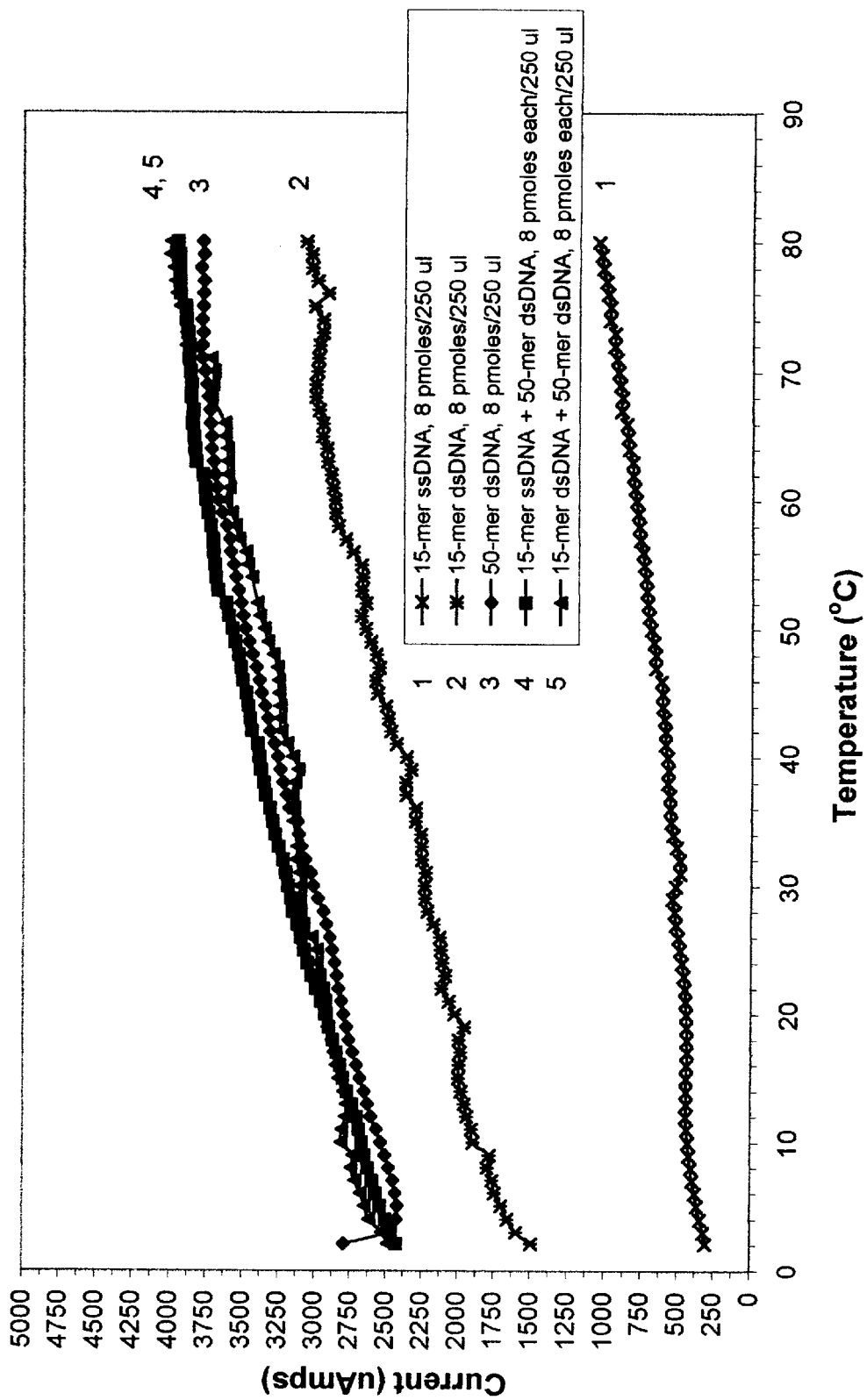
Fig. 26B. Comparison of AA of mixes of 50-mer dsDNA with unrelated 15-mer ssDNA or with unrelated 15-mer dsDNA during increasing temperature

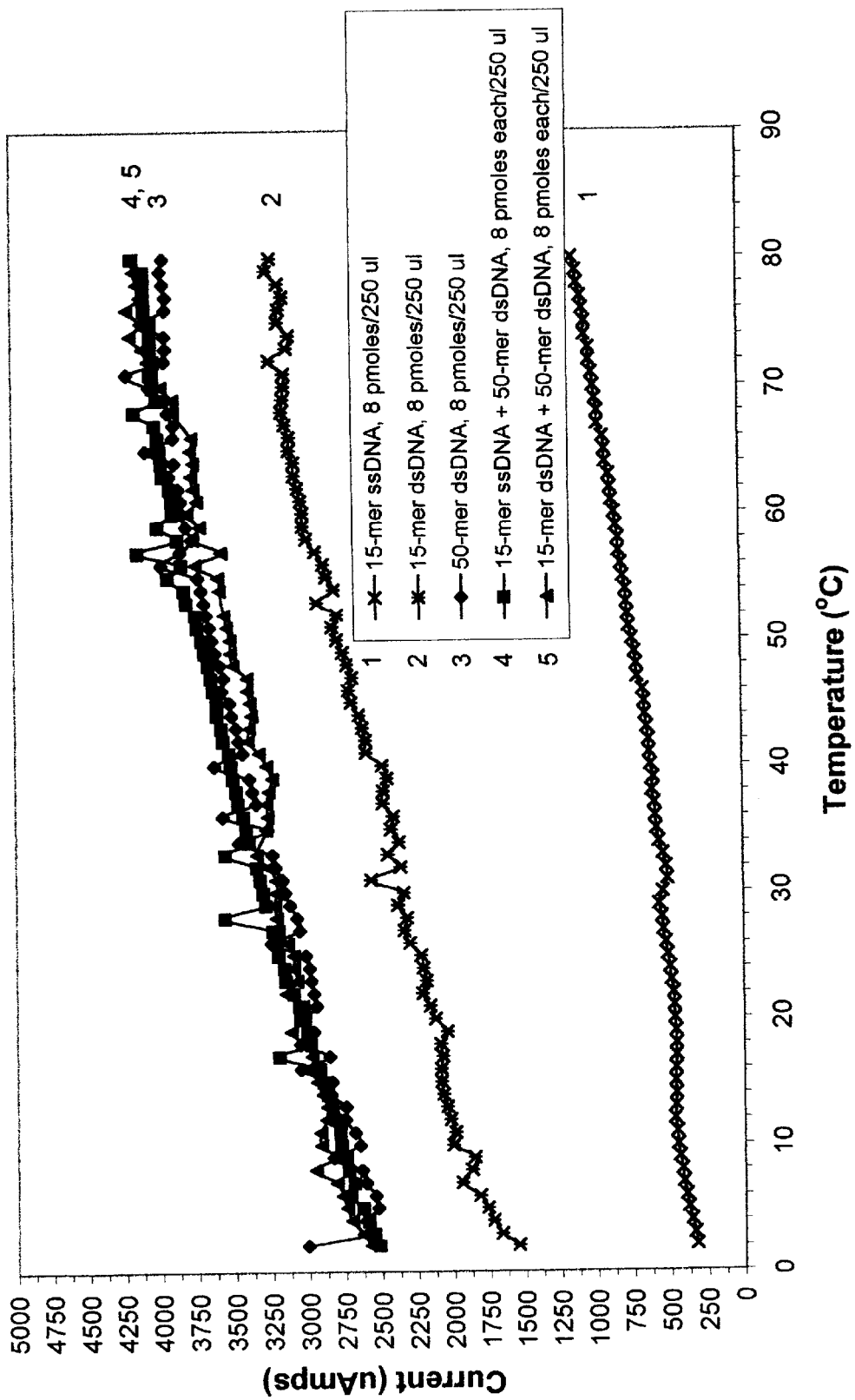
Fig. 26A. Comparison of IPA of mixes of 50-mer dsDNA with unrelated 15-mer ssDNA or with unrelated 15-mer dsDNA during increasing temperature

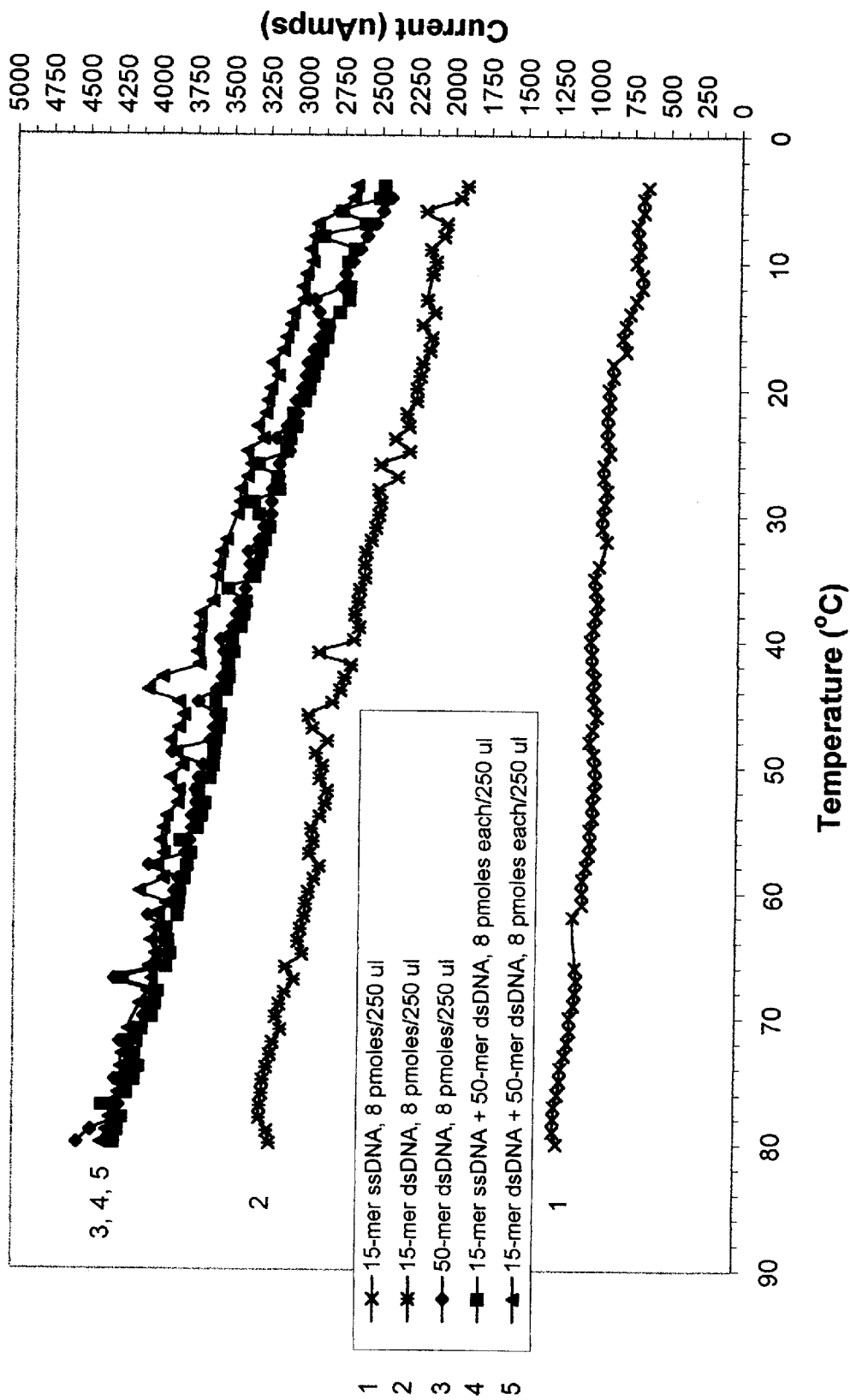

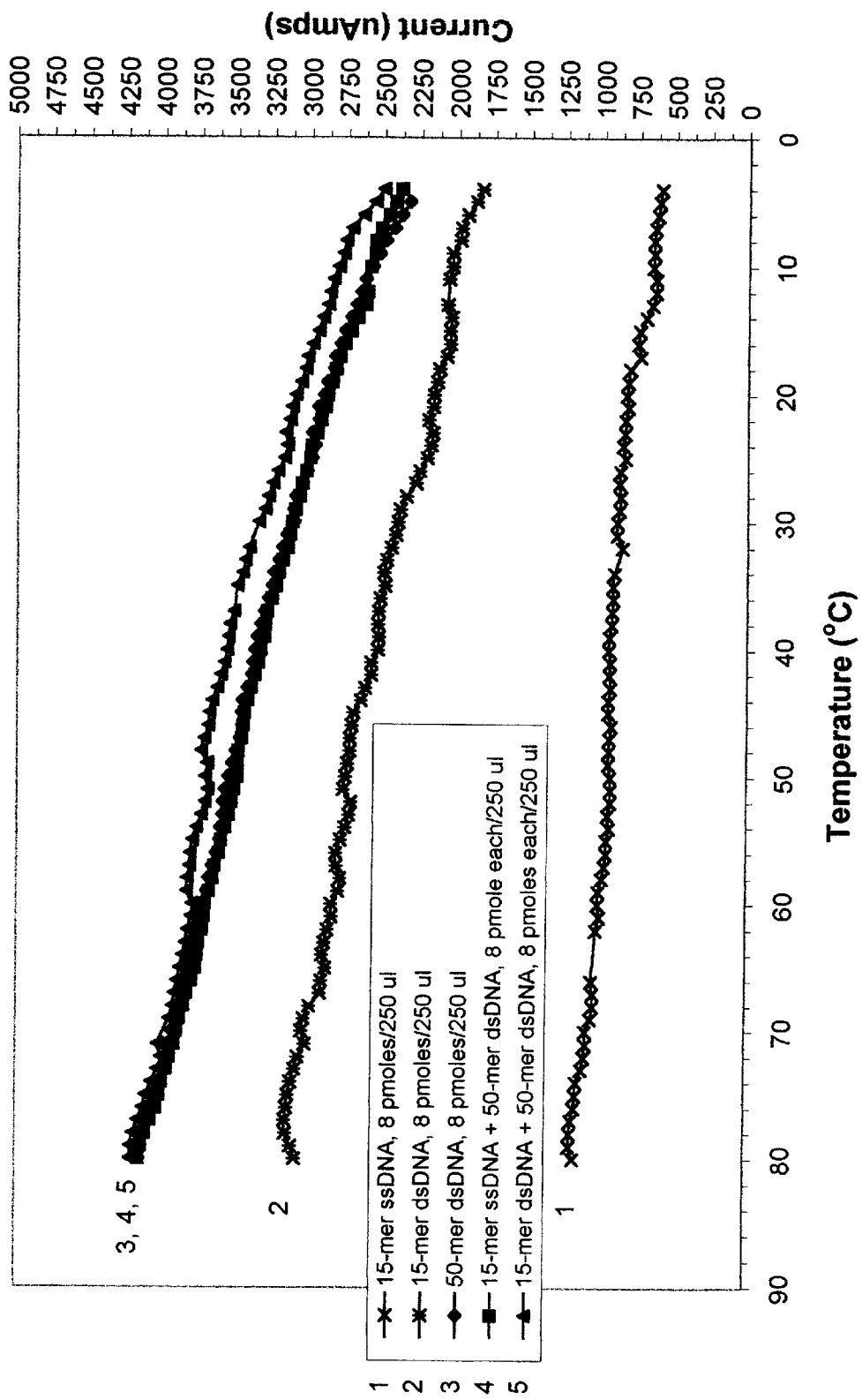

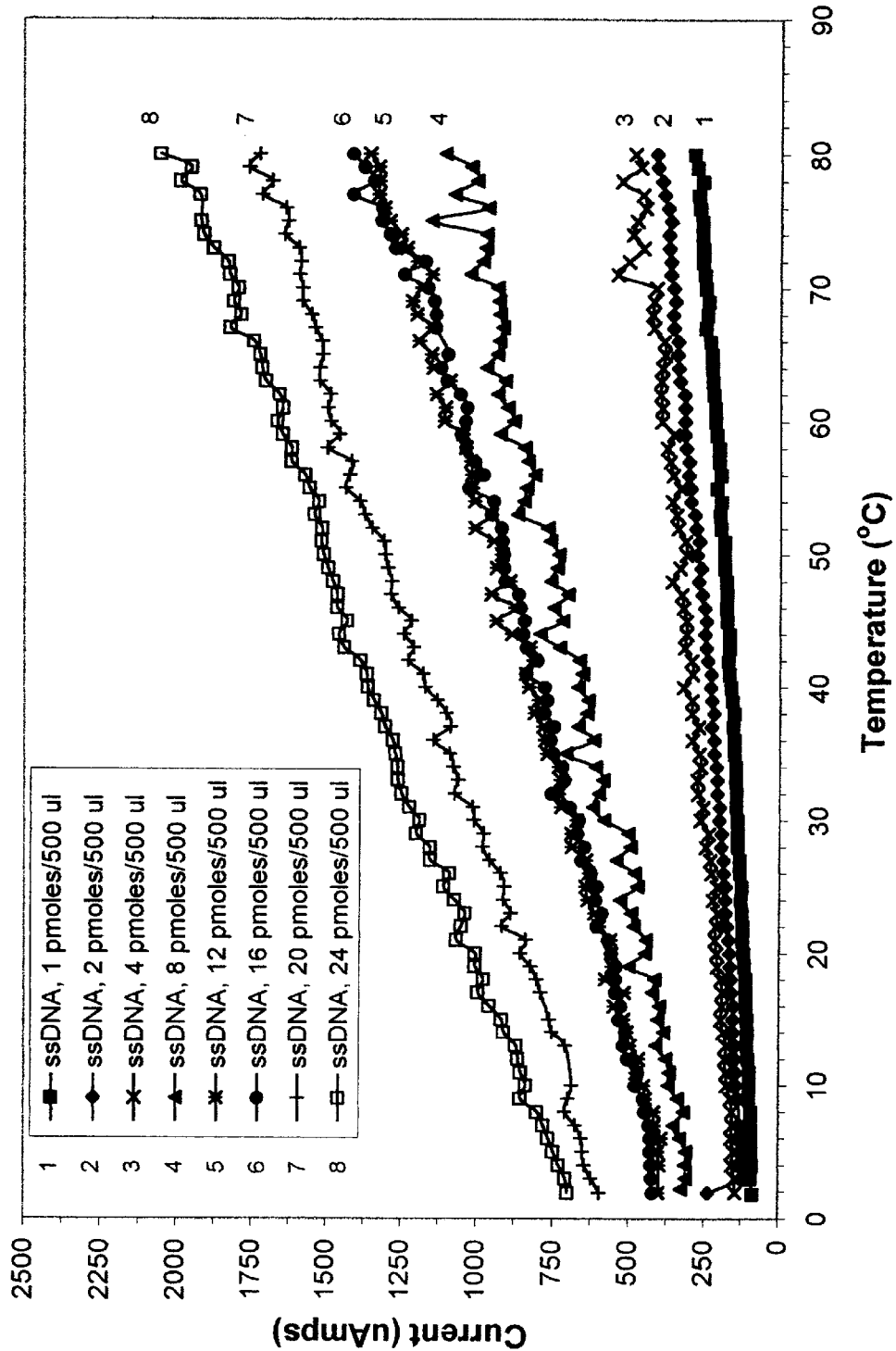
Fig. 28A. Comparison of IPA of different concentrations of 15-mer ssDNA with increasing temperature during agitation

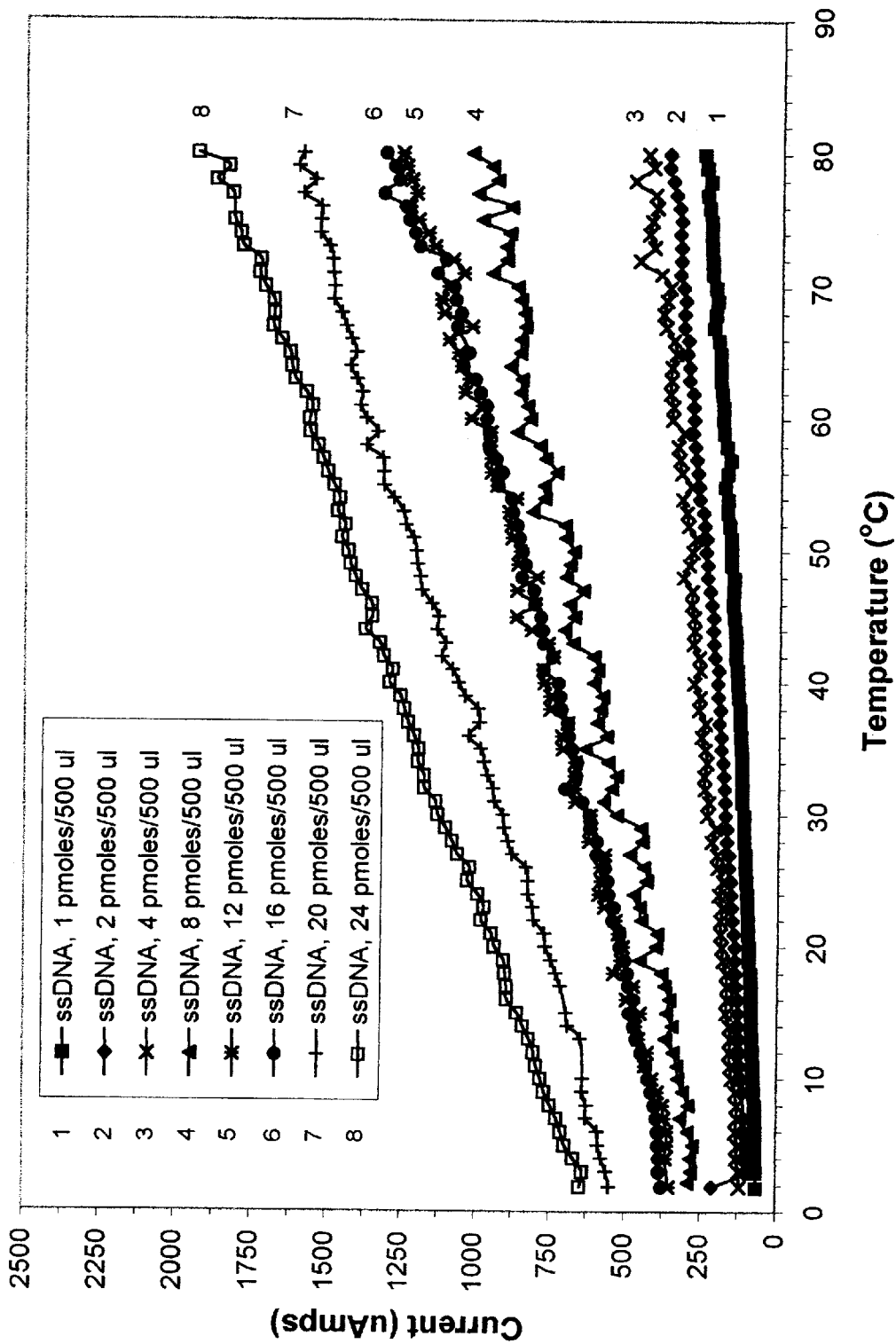

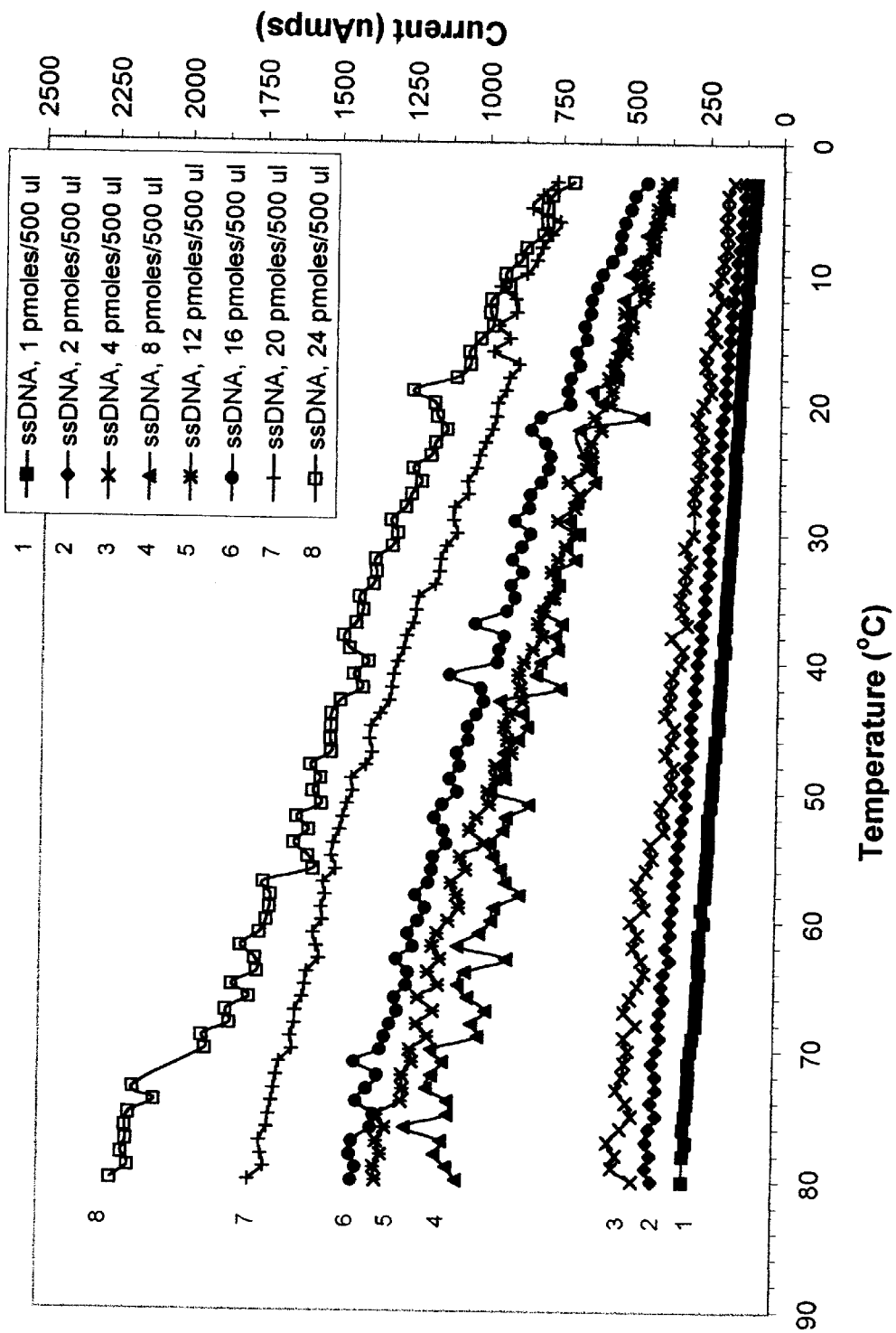
Fig. 29A. Comparison of IPA of different concentrations of 15-mer ssDNA with decreasing temperature during agitation

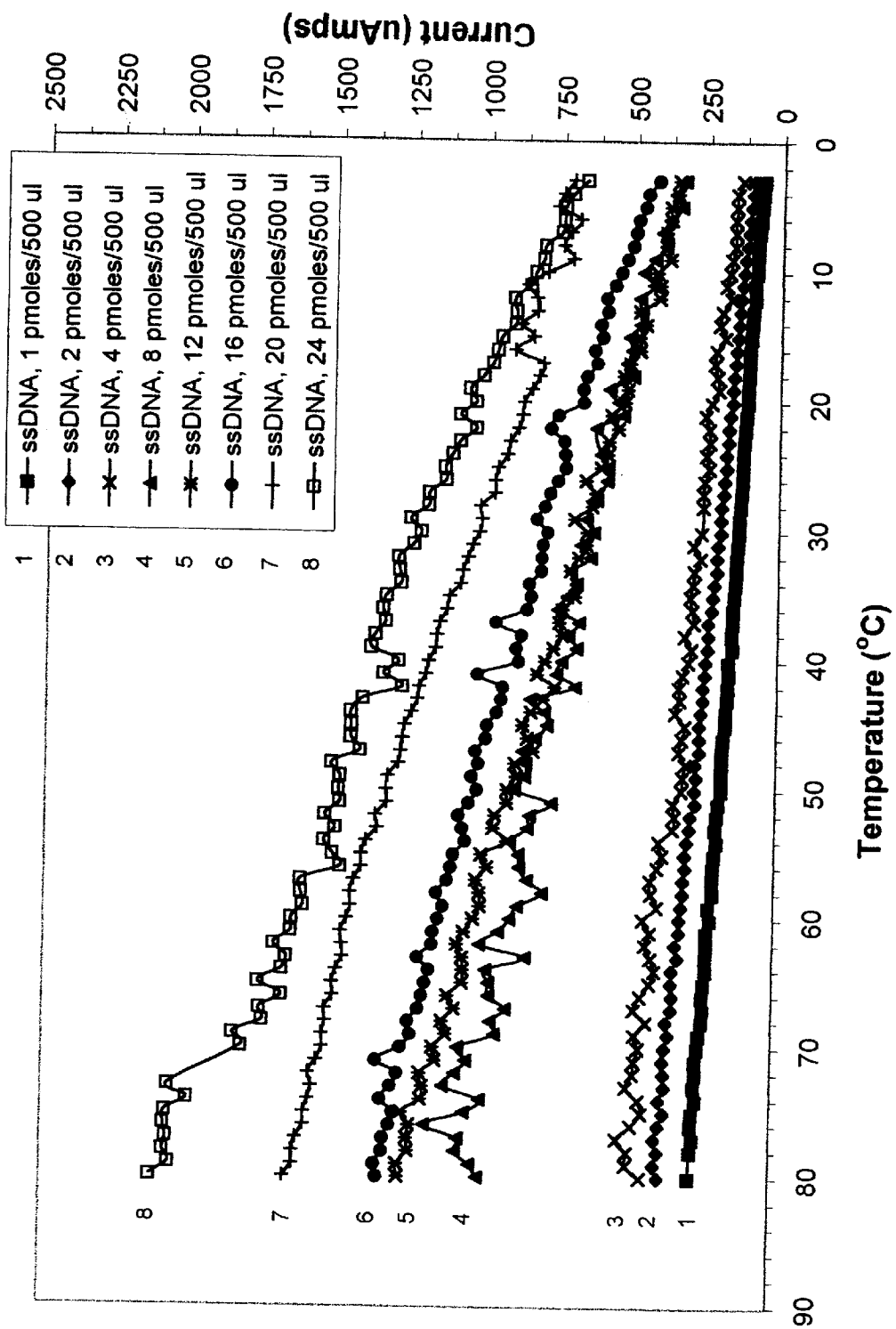
Fig. 29B. Comparison of AA of different concentrations of 15-mer ssDNA with decreasing temperature during agitation

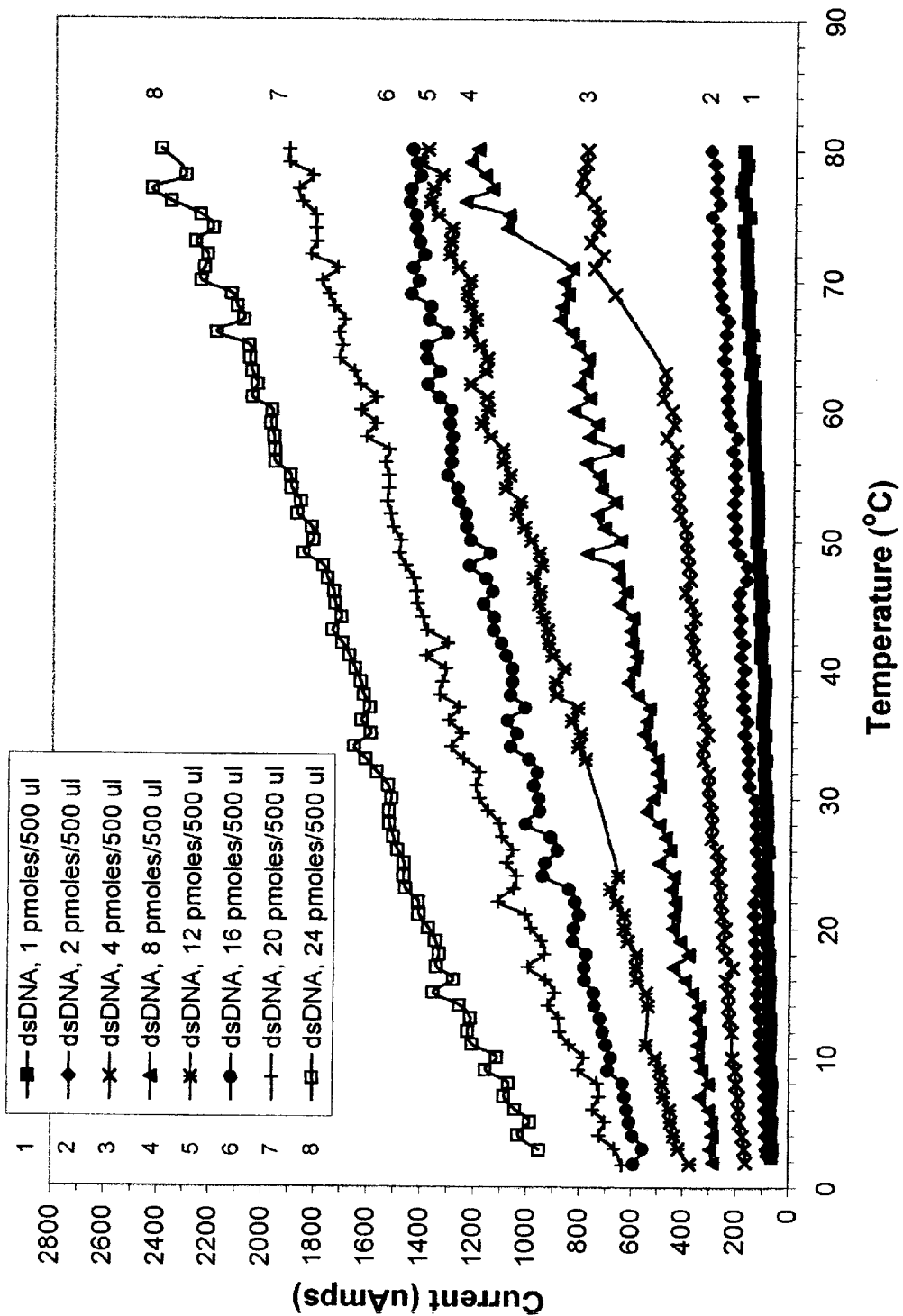
Fig. 30A. Comparison of IPA of different concentrations of 15-mer dsDNA with increasing temperature during agitation

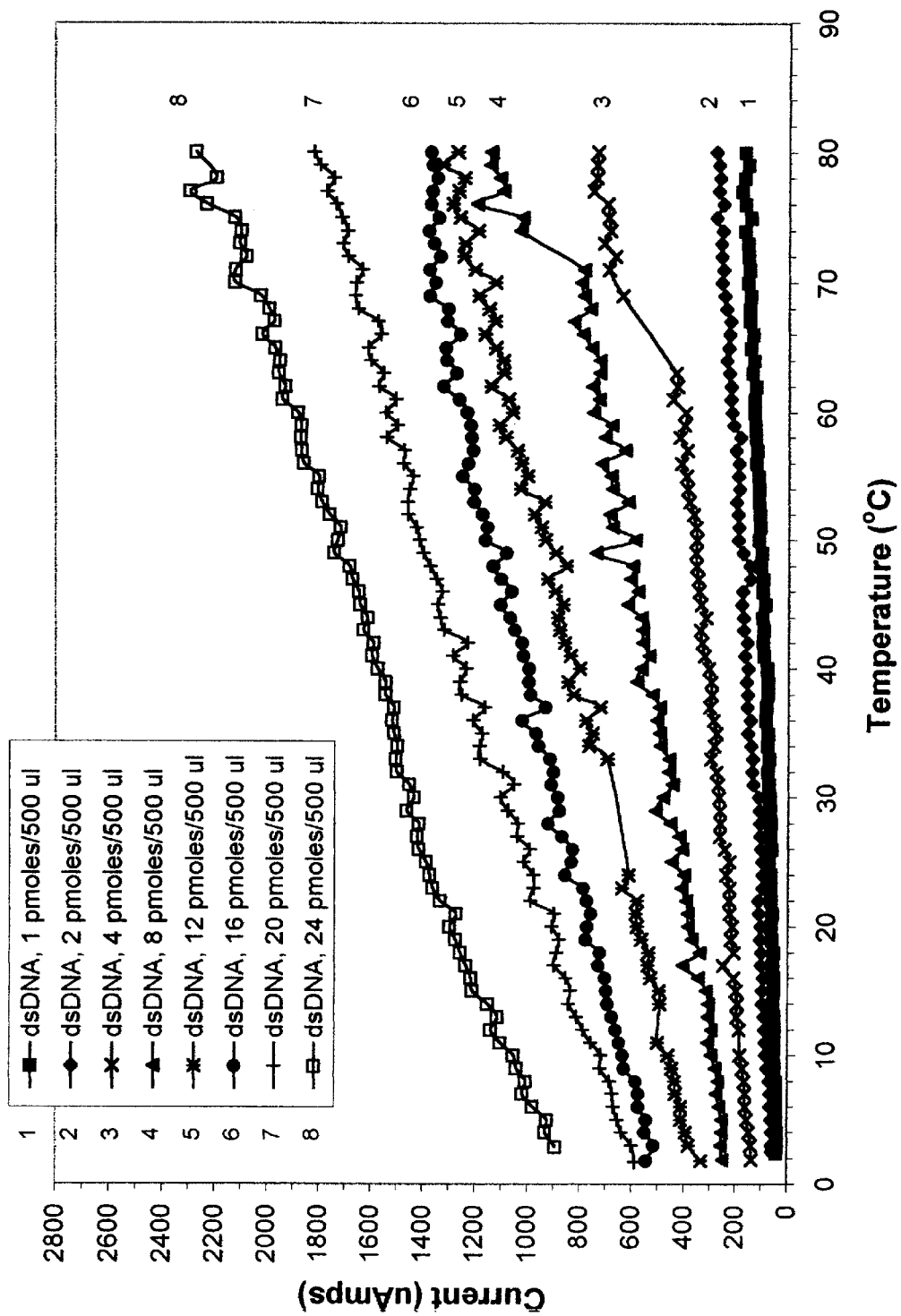
Fig. 30B. Comparison of AA of different concentrations of 15-mer dsDNA with increasing temperature during agitation

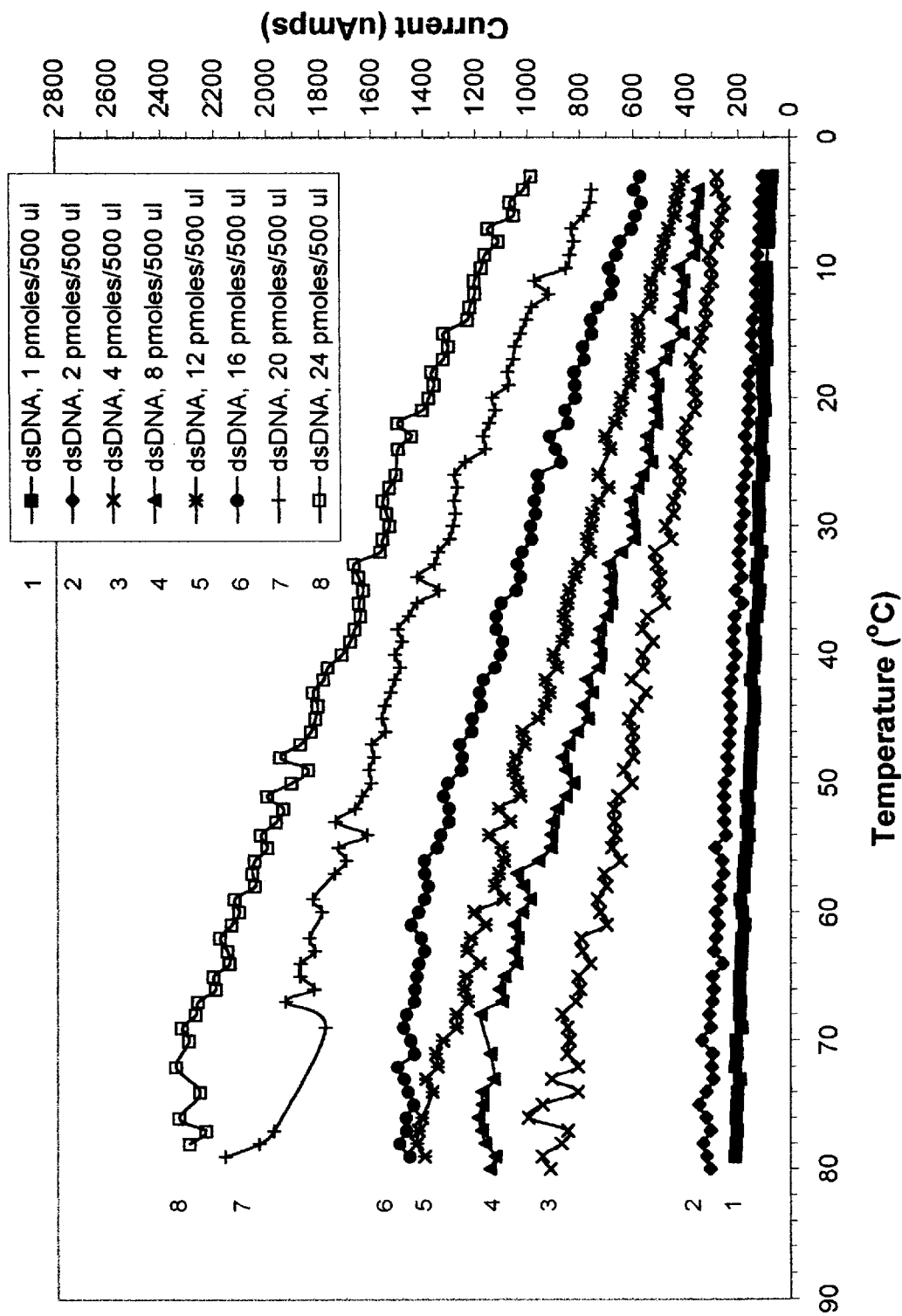
Fig. 31A. Comparison of IPA of different concentrations of 15-mer dsDNA with decreasing temperature during agitation

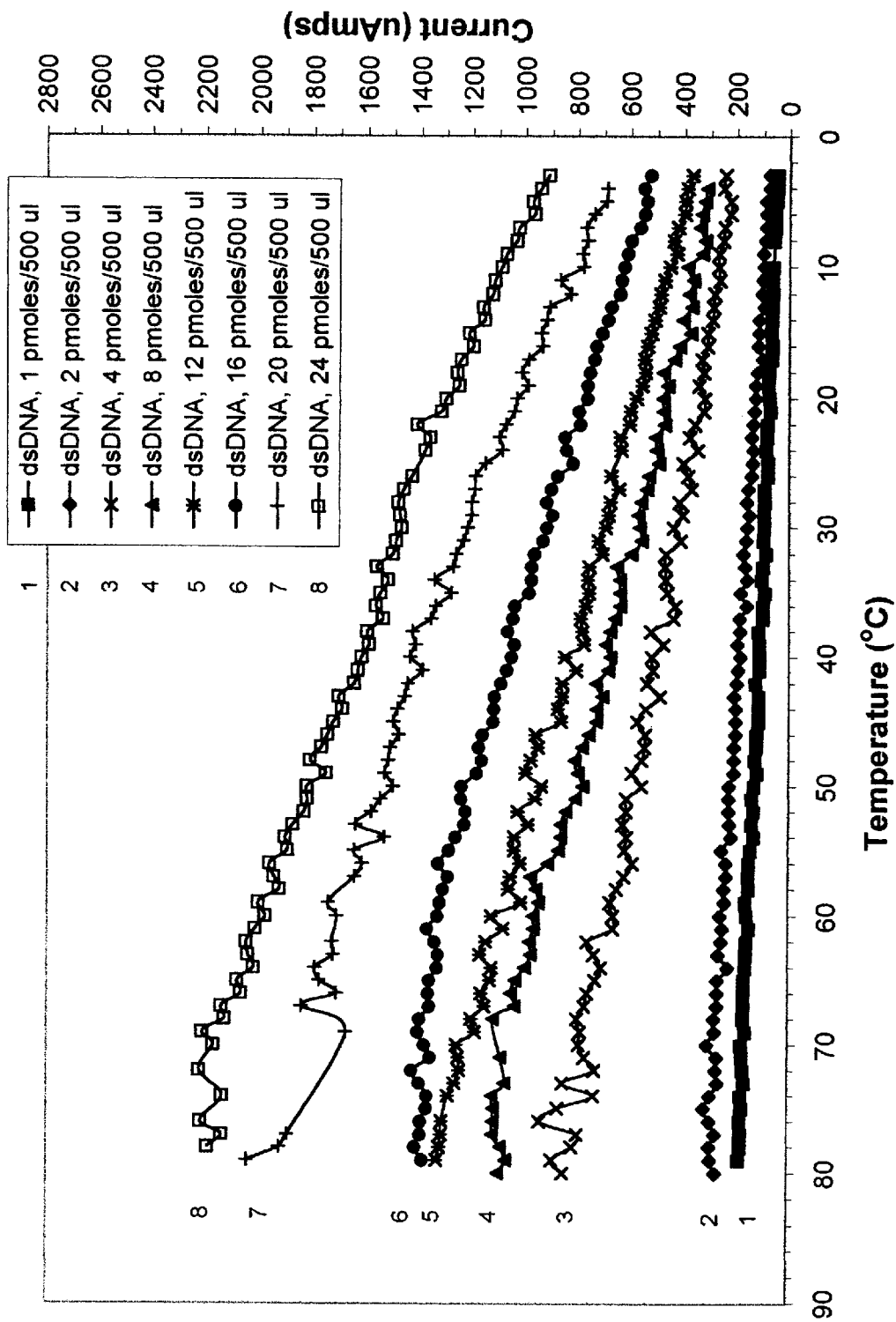
Fig. 31B. Comparison of AA of different concentrations of 15-mer dsDNA with decreasing temperature during agitation

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 1
ctgtcatctc tggtg                                                    15

<210> SEQ ID NO 2
<211> LENGTH: 50
<212> TYPE: DNA
<213> ORGANISM: Artificial Sequence
<220> FEATURE:
<223> OTHER INFORMATION: derived from exon 10 of the human cystic
      fibrosis gene

<400> SEQUENCE: 2
gagcaccatg acagacactg tcatctctgg tgtgtcctac gatgactctg              50

<210> SEQ ID NO 3
<211> LENGTH: 15
<212> TYPE: DNA
<213> ORGANISM: Artificial Sequence
<220> FEATURE:
<223> OTHER INFORMATION: derived from the Drosophila erg gene

<400> SEQUENCE: 3
cagaaaggtt tcaag                                                    15
```

AMPEROMETRIC AFFINITY ASSAY AND ELECTRICALLY STIMULATED COMPLEXES OF NUCLEIC ACIDS

CROSS-REFERENCE TO RELATED APPLICATIONS

This application is a continuation-in-part of U.S. patent application Ser. No. 09/911,047, filed Jul. 23, 2001, which is a continuation-in-part of U.S. Ser. No. 09/490,273 now U.S. Pat. No. 6,265,170 to Picard et al., filed Jan. 24, 2000, the disclosures of which are incorporated by reference herein in their entireties.

SPECIFICATION

BACKGROUND OF THE INVENTION

1. Field of Invention

The invention relates to the conductivity of nucleobase-containing sequences, such as DNA, RNA and analogues thereof, and more particularly to methods wherein the conductivities of such sequences are analyzed to reveal information about additional properties of the sequences.

2. Description of Related Art

It has been understood for a number of years that biological molecules can be isolated and characterized through the application of an electric field to a sample.

Electrophoresis is perhaps the most well-known example of an isolation and characterization technique based on the influence of electric fields on biological molecules. In gel electrophoresis, a uniform matrix or gel is formed of, for example, polyacrylamide, to which an electric field is applied. Mixtures applied to one end of the gel will migrate through the gel according to their size and interaction with the electric field. Mobility is dependent upon the unique characteristics of the substance such as conformation, size and charge. Mobilities can be influenced by altering pore sizes of the gel, such as by formation of a concentration or pH gradient, or by altering the composition of the buffer (pH, SDS, DOC, glycine, salt). One- and two-dimensional gel electrophoresis are fairly routine procedures in most research laboratories. Target substances can be purified by passage through and/or physical extraction from the gel.

In the ongoing search for more sensitive, accurate and rapid assay techniques, one research group developed an assay comprising analyzing the effects of an electric field on the fluorescent intensity of nucleic acid hybridization duplexes. See U.S. Pat. Nos. 5,846,729 to Wu et al., 6,060,242 to Nie et al. and 6,294,333 to Picard et al. The researchers indicated that the fluorescent intensity of a one base-pair mismatched duplex differed from that of a perfectly matched duplex or triplex when subjected to an electrical field. Thus, the patents purport to disclose a method for detecting a nucleotide sequence, wherein an electric field is applied to a liquid medium prior to or concurrently with a detecting step, and a change in an intensity of a fluorescent emission as a function of the electric field is detected as an indication of whether the probe is hybridized to a completely complementary nucleotide sequence or an incompletely complementary nucleotide sequence.

Others have studied the electrical properties of DNA more directly. For example, Porath et al., "Direct Measurement of Electrical Transport through DNA Molecules," 403 Nature 635 (Feb. 10, 2000), discloses the current-voltage curves measured at room temperature on a DNA molecule trapped between two metal nanoelectrodes. Current was essentially zero up to a threshold voltage of about 1–2 volts. There is no suggestion in this reference that DNA properties other than electric transport can be correlated with current flow through DNA.

U.S. Pat. No. 5,783,063 to Clarkson et al. discloses a method for estimating a property of a nucleic acid material, which property is one to which the electrical conductivity of the nucleic acid material is related. The only properties detected are the concentration of the nucleic acid material in solution and the molecular weight of the nucleic acid material. The method comprises measuring the electrical conductivity of a solution containing the nucleic acid material and estimating from the measurement the concentration or molecular weight of the nucleic acid material by reference to calibration curves.

All references cited herein are incorporated herein by reference in their entireties.

BRIEF SUMMARY OF THE INVENTION

The invention provides a method for determining an affinity of a first nucleobase-containing sequence for a second nucleobase-containing sequence, the method comprising:

providing a test medium containing the first nucleobase-containing sequence and the second nucleobase-containing sequence, wherein the first nucleobase-containing sequence and the second nucleobase-containing sequence are of different lengths;

applying a voltage across the test medium;

measuring a test electric current through the test medium; and determining the affinity by evaluating whether the test electric current is equivalent to a reference electric current of a reference medium containing a longer of the first nucleobase-containing sequence and the second nucleobase-containing sequence.

Also provided is a complex in an electrically-stimulated phase containing at least two nucleobase-containing sequences in a medium, wherein the electrical conductivity of the medium increases linearly without a plateau as the temperature of the medium approaches and exceeds a Tm of the complex.

BRIEF DESCRIPTION OF SEVERAL VIEWS OF THE DRAWINGS

The invention will be described in conjunction with the following drawings in which like reference numerals designate like elements and wherein:

FIGS. 1A, 1B, 2A, 2B, 3A, 3B, 3C, 3D, 4A, 4B, 4C and 4D are graphs of current plotted as a function of temperature;

FIGS. 5A, 5B, 6A, 6B, 7A, 7B, 8A and 8B are graphs of current plotted as a function of temperature and DNA concentration;

FIGS. 9A and 9B are graphs of current plotted as a function of DNA concentration;

FIGS. 10A, 10B, 11A, 11B, 12A, 12B, 13A, 13B, 14A, 14B, 15A and 15B are graphs of current plotted as a function of temperature and voltage;

FIGS. 16A, 16B, 17A, 17B, 18A, 18B, 19A, 19B, 20A, 20B, 21A, 21B, 22A, 22B, 23A, 23B, 24A, 24B, 25A, 25B, 26A, 26B, 27A and 27B are graphs of current plotted as a function of temperature and DNA affinity; and FIGS. 28A, 28B, 29A, 29B, 30A, 30B, 31A and 31B are graphs of current plotted as a function of temperature and DNA concentration during agitation.

DETAILED DESCRIPTION OF THE INVENTION

The invention is based on the inventor's discovery that the current flow through a medium containing nucleobase-containing sequences provides information regarding several properties of the sequences, which constitute the electron transfer pathway through the medium. These properties include the length of the sequences, the concentration of the sequences, and the affinity of one sequence for a different sequence in the medium.

The term "affinity" as used herein is intended to encompass specific associations between nucleobase-containing sequences, regardless of whether such associations occur via bonds or via some more tenuous means of specific association under conditions previously thought to preclude nucleobase-to-nucleobase binding. The term "affinity" as used herein therefore encompasses traditional notions of nucleobase-to-nucleobase binding, recently disclosed homologous base binding associations described by the inventor and his colleagues in, e.g., U.S. patent application Ser. No. 09/909,496, filed Jul. 20, 2001, and entitled "PARALLEL OR ANTIPARALLEL, HOMOLOGOUS OR COMPLEMENTARY BINDING OF NUCLEIC ACIDS OR ANALOGUES THEREOF TO FORM DUPLEX, TRIPLEX OR QUADRUPLEX COMPLEXES", and other forms of specific associations between adjacent nucleobase-containing sequences.

Accordingly, the types of affinity that can be detected by the invention are not particularly limited. For example, the invention can detect bonding of two to four nucleobase-containing sequences in parallel or antiparallel relation to one another, wherein specific bonding is through homologous base pairing preference and/or Watson-Crick base pairing preference.

Applying a voltage through the medium in which the nucleobase-containing sequences are contained, and measuring the resulting electric current can indicate the affinity of a first nucleobase-containing sequence present in the medium for a second nucleobase-containing sequence also present in the medium. The inventor has discovered the following relationships between electric current flow and nucleobase-containing sequence to nucleobase-containing sequence affinity. When two single-stranded nucleobase-containing sequences (e.g., ssDNA) of differing lengths have affinity for each other under the test conditions, the test current ($C_T$) flowing through a test medium containing an equimolar mixture of the sequences is substantially equivalent (i.e., within experimental error) to the current ($C_L$) of a reference medium containing the longer sequence in the absence of the shorter sequence. When two such single-stranded nucleobase-containing sequences have no affinity for each other under the test conditions, the test current is substantially equivalent to the sum of the current ($C_L$) of a reference medium containing the longer sequence in the absence of the shorter sequence, plus the current ($C_S$) of a reference medium containing the shorter sequence in the absence of the longer sequence. When two double-stranded nucleobase-containing sequences (e.g., dsDNA) of differing lengths have affinity for each other under the test conditions, the test current ($C_T$) flowing through a test medium containing an equimolar mixture of the sequences is substantially equivalent (i.e., within experimental error) to the sum of the current ($C_L$) of a reference medium containing the longer sequence in the absence of the shorter sequence, plus the current ($C_S$) of a reference medium containing the shorter sequence in the absence of the longer sequence. When two such double-stranded sequences have no affinity for each other under the test conditions, the test current is substantially equivalent to the current ($C_L$) of a reference medium containing the longer sequence in the absence of the shorter sequence. These relationships (which also apply to nucleobase-containing sequences other than DNA) are further illustrated in the following table.

| Longer Sequence | Shorter Sequence | Affinity | Current ($C_T$) |
| --- | --- | --- | --- |
| SsDNA | SsDNA | Yes | $C_L$ |
| SsDNA | SsDNA | No | $\sim C_L + C_S$ |
| DsDNA | DsDNA | Yes | $\sim C_L + C_S$ |
| DsDNA | DsDNA | No | $C_L$ |

The current detected is a function of a number of properties of the sequences being assayed (as discussed above) and the media, as well as the voltage applied across the media. The voltage is applied to the sample prior to or concurrent with measuring current flow. The amount of voltage to be applied to the medium containing the nucleobase-containing sequences varies, but should be selected such that a current can be detected. In certain preferred embodiments, the voltage is about 1V to about 30V, preferably 3V to 27V. The voltage can be DC or AC. The voltage can be pulsed or applied constantly over a desired period of time. The voltage is typically applied across the medium through a pair of metal electrodes submerged in the medium.

If desired, a calibration curve can be generated, wherein the magnitude of the measured signal (e.g., preferably electric current, or a related electrical parameter, such as resistance) is a function of the affinity between the sequences of interest.

Unlike certain prior art methods, the assay of the invention is preferably homogeneous. The assay can be conducted without separating affinity complexed nucleobase-containing sequences from uncompleted sequences prior to detecting the magnitude of the measured signal. The assay does not require a gel separation step, thereby allowing a great increase in testing throughput. Quantitative analyses are simple and accurate. Consequently the assay saves time and expense, and can be easily automated. Furthermore, it enables affinity-altering variables such as buffer, pH, ionic concentration, temperature, incubation time, sequence concentration, intercalator concentration, sequence length and possible cofactor requirements to be rapidly determined.

The assay can be conducted in e.g., a solution within a well, on an impermeable surface or on a biochip.

Suitable nucleobase-containing sequences for use in the inventive assay include, e.g., nucleic acids having deoxyribose phosphate or ribose phosphate backbones (e.g., DNA, RNA, mRNA, hnRNA, rRNA, tRNA or cDNA) or a nucleic acid analogue. Preferred nucleic acid analogues contain an uncharged or partially charged backbone (i.e., a backbone having a charge that is not as negative as a native DNA backbone), and include, e.g., PNA and LNA.

It is preferred that the two nucleobase-containing sequences whose affinity for each other is being studied be of differing lengths. The difference in length must preferably be sufficiently large such that a current through a medium containing the shorter of the two sequences is detectably lower than a current through a medium containing the longer of the two sequences. As shown in the Examples below, a 35-base difference in sequence length is suitable; however, lesser or greater differences in length can be readily selected by one skilled in the art using the instant disclosure as a guide. The absolute (as opposed to relative) length of each sequence is not particularly limited.

The assay of the invention can be performed over a wide variety of temperatures, such as, e.g., from 2° C. to 85° C. Certain prior art assays require measurements at elevated temperatures (e.g. 35° C. or greater), adding cost and delay to the assay. On the other hand, the invention can be conducted at room temperature or below (e.g., at a temperature below 25° C.).

The inventive assay is extremely sensitive, thereby obviating the need to conduct PCR amplification of the target. Conductivity measurements can distinguish samples having as little as about 1 pmole of each sequence in 40 microliters. Decreasing the sample volume would permit the use of even smaller amounts of sequences. It should go without saying that the foregoing values are not intended to suggest that the method cannot detect higher concentrations.

The test (or reference) medium can be $H_2O$ alone or it can be any conventional medium known to be suitable for preserving nucleotides. See, e.g., Sambrook et al., "Molecular Cloning: A Lab Manual," Vol. 2 (1989). For example, the liquid medium can comprise nucleotides, water, and buffers.

The inventive assay can be used to, e.g., determine the affinity of a first nucleobase-containing sequence for a second nucleobase-containing sequence.

The invention will be illustrated in more detail with reference to the following Examples, but it should be understood that the present invention is not deemed to be limited thereto.

EXAMPLES

Example 1

Example 1 demonstrates the conductivity of DNA oligonucleotides in a homogeneous solution and examines the change in conductivity as a function of temperature throughout a temperature range from 2° C. to 80° C. Sense and antisense 15-mer ssDNA sequences, possessing a 53% GC content, were synthesized on a DNA synthesizer (Expedite 8909, PerSeptive Biosystems) and purified by HPLC. SsDNA oligonucleotides were dissolved in $ddH_2O$ and diluted to a concentration of 1 pmole/$\mu$l. Equimolar amounts of complementary oligonucleotides were denatured at 95° C. for 10 minutes and allowed to anneal gradually in the presence of 10 mM Tris, pH 7.5, 1 mM EDTA and 100 mM NaCl, as the temperature cooled to 21° C. over 1.5 hours. DsDNA oligonucleotides were diluted in $ddH_2O$ to a concentration of 1 pmole/$\mu$l.

Sequence for the sense strand of the wild-type 15-mer DNA (SEQ ID NO:1): 5'-CTG TCA TCT CTG GTG-3'.

Sequence for the antisense strand of the wild-type 15-mer DNA (SEQ ID NO:1): 5'-CAC CAG AGA TGA CAG-3'.

Eight pmoles of the sense strand of SEQ ID NO:1 were tested in a final volume of 500 $\mu$l $ddH_2O$ in a 1.1 cm cuvette. The cuvette was placed in a programmable Peltier block (PTP-6 digital temperature controller) in a PE Spectrophotometer, model Lambda Bio10. Two platinum electrodes, 2 mm apart, were introduced into the test medium. Three mm of each electrode was submerged in the liquid. Nine volts of DC current were applied for 500 msec periodically to the test medium as the temperature of the Peltier block and consequently the test medium was raised from 2° C. to 80° C. Readings of amperometric flow through the test medium were taken at every 1° C. increase in temperature. A temperature probe was placed directly in a test medium in an adjacent cuvette in the Peltier block to measure temperature of the test medium at the time of amperometric assessment. Measurements were taken at about 30 second intervals between each 500 msec application of 9 volts. Amperometric values were acquired on software custom designed by Dr. William Kwong (George Brown College, Toronto, Canada). Measurements were taken of the initial peak amperometric flow (IPA) and then of the average amperometric flow (AA) during the final 400 msec of the 500 msec period during which the voltage was applied to the test medium at each temperature. FIGS. 1A and 1B plot the IPA and AA measurements taken, respectively, between 2° C. and 80° C. in a single experiment wherein the test medium was steadily heated. FIGS. 2A and 2B plot the IPA and AA values of the same test medium, respectively achieved, as consecutive measurements were taken of the test medium as the temperature was reduced from 80° C. to 2° C. The test medium was maintained at 80° C. for about 2 minutes before the series of measurements with decreasing temperature was commenced. FIGS. 1 and 2 also show the amperometric flow observed in a control sample consisting of $ddH_2O$ alone.

The data in FIGS. 1 and 2 demonstrated that a test medium comprising ssDNA in $ddH_2O$ is far more conductive of electricity than is $ddH_2O$ alone. Conductance values increased with increasing temperature and declined with decreasing temperature. The relationship between amperometric flow of the test medium containing ssDNA and temperature of the test medium was generally linear. Sequence variation in the ssDNA produce significantly different conductance values at all temperatures (data not shown). There were however idiosyncratic temperature phases in which the amperometric flow deviated from the general trend. For instance, the rate of change in conductance of the test medium containing ssDNA between 2° C. and 20° C. was greater than that between 20° C. and 80° C. Comparison of the IPA and AA values revealed that the IPA was almost always a higher value than the AA. With increasing temperature there arose a widening gap between the IPA values and the AA values generated by the test medium containing ssDNA. This difference between IPA and AA values was maintained as the temperature declined from 80° C. to 2° C. A more linear pattern was observed for the IPA and AA values under conditions of declining temperature.

Surprisingly, and contrary to the teaching in certain prior art, the amperometric flow values of the test medium containing ssDNA observed with decreasing temperature bore little relationship to those observed with increasing temperature (compare FIGS. 1 and 2). This hysteretic effect was most pronounced at low temperatures where the values recorded at temperatures during declining temperature measurements were noticeably higher and bore little resemblance to the values recorded at the same temperatures during increasing temperature measurements. The cause of this hysteretic effect is currently unknown. Thus it is important to take account of the history of the sample when detecting the conductance characteristics of nucleic acids with special reference to the temperatures to which they are subjected and the voltages to which they have been subjected. Nothing in the data suggested that there was substantial migration of the DNA to either electrode. No accumulation of DNA was observed at the electrode. Reversal of the polarity of the electrodes did not affect the conductance values obtained in repetitions of the experiments (data not shown).

The conductance of the test medium comprising 8 pmoles of the 15-mer annealed dsDNA (SEQ ID NO:1) in 500 µl of ddH$_2$O was then examined as a function of temperature following consecutive 500 msec applications of 9 volts (FIGS. 3A, 3B, 4A and 4B). The test medium containing dsDNA was more conductive of electricity than was the test medium containing a like amount of ssDNA. Conductance values for the test medium containing dsDNA increased with increasing temperature and declined with decreasing temperature primarily in a linear fashion and with less low temperature idiosyncrasy than did the test medium containing ssDNA. Unexpectedly, the linear progression of amperometric flow within the dsDNA was not disrupted as the temperature of the test medium passed through 45° C., the T$_m$ of the 15-mer dsDNA. Even though conversion from duplex DNA to ssDNA, and vice versa, ought to have occurred within the temperature range tested (2° C. to 80° C.), the originally duplex complementary ssDNA strands appear to have remained in a duplex form or at least in very close proximity to each other during the serial application of voltage, so as to result in no interruption of the linear progression of IPA and AA values. The IPA values throughout were slightly higher than the AA values. The hysteretic effect observed between data points generated during increasing temperature as opposed to the data points generated during decreasing temperature was not as pronounced when the conductance of a test medium containing dsDNA was being measured than when a test medium containing ssDNA was being tested. The test medium containing the dsDNA produced similar conductance values at 2° C. both at the start and at the end of the sequence of temperature variations. It appears that the application of the voltage served to keep the duplex strands from separating at temperatures above the T$_m$ of the duplex.

Four pmoles of the sense strand of the 15-mer SEQ ID NO:1 were tested in combination with four pmoles of the antisense strand of the 15-mer SEQ ID NO:1 in a test medium comprising a final volume of 500 µl ddH$_2$O. The test media were heated from 2° C. to 80° C. and cooled from 80° C. to 2° C., with IPA and AA readings taken at 1° C. intervals following 500 msec applications of 9 Volts of DC voltage as described above. The IPA and AA values obtained for the test medium containing the mix of the two antiparallel complementary 15-mer ssDNAs during increasing temperatures are shown in FIGS. 3C and 3D, respectively. The IPA and AA values produced by this test medium during decreasing temperatures are shown in FIGS. 4C and 4D, respectively.

Conductance values for the test medium containing the mix of the two antiparallel complementary 15-mer ssDNAs increased with increasing temperature primarily in a linear fashion and appeared to comprise the additive IPA and AA values attributable to 4 pmoles of each ssDNA in the test medium. At any given temperature, these amperometric values for the test medium containing the two non-annealed ssDNAs of SEQ ID NO:1 (FIGS. 3C and 3D) were lower than those observed for the test medium containing the annealed dsDNA of SEQ ID NO:1 (FIGS. 3A and 3B), though the test media contained like masses of nucleotides. While conductance values for the test medium containing the original dsDNA of SEQ ID NO:1 declined linearly as the temperature was decreased from 8° C. to 2° C. (FIGS. 4A and 4B), an altered conductance pattern was observed for the test medium containing the mix of antiparallel complementary strands of SEQ ID NO:1 during declining temperature measurements (FIGS. 4C and 4D). IPA and AA values for the test medium containing the mix of the two ssDNA strands declined linearly from 80° C. to 48° C., plateaued during the temperature decrease from 48° C. to 38° C., and then resumed their linear decline as the temperature was reduced from 38° C. to 2° C. (FIGS. 4C and 4D). The plateau of conductance values at temperatures near the T$_m$ of SEQ ID NO:1 appears indicative of the two strands of SEQ ID NO:1 annealing during the period when the temperature declined. The amperometric values for the test medium containing the mix of the two ssDNAs between 38° C. to 2° C. (FIGS. 4C and 4D) were very similar to those for the dsDNA between 38° C. to 2° C. (FIGS. 4A and 4B). This pattern of amperometric flow observed for the two antiparallel complementary ssDNA strands during the period of temperature decline from 80° C. to 2° C. (FIGS. 4C and 4D), strongly suggest that the complementary bases of the two ssDNAs were not bound to one another prior to the apparent annealing phase. By comparison, the non-disrupted linear IPA and AA values observed for the test medium containing the previously annealed dsDNA (SEQ ID NO:1) between 80° C. to 2° C. (FIGS. 4A and 4B), reinforces the proposal that the duplex remained intact at elevated temperatures or at least that the separated complementary ssDNA strands remained in very close proximity to each other at temperatures above the T$_m$ of SEQ ID NO:1 so as to continue to accomplish electron transfer through the medium in a temperature dependent fashion.

The linearity of conductance of the test medium containing 8 pmoles of the sense strand of SEQ ID NO:1 observed as the temperature declined from 80° C. to 18° C. (FIGS. 2A and 2B) indicated that parallel homologous binding between identical strands was not occurring. Parallel homologous binding would be expected to give rise to a conductance plateau.

Example 2

Example 2 examines the effect of varying DNA concentration on the conductivity of the test medium as a function of temperature. One, two, four, eight, twelve, sixteen, twenty and twenty-four pmoles of the sense strand of SEQ ID NO:1 were each tested in a test medium comprising a final volume of 500 µl ddH$_2$O. The test media were heated from 2° C. to 80° C. and cooled from 80° C. to 20° C., with IPA and AA readings taken at 1° C. intervals following 500 msec applications of 9 Volts of DC voltage as described in Example 1. The IPA and AA values obtained for the test media containing ssDNA during increasing temperatures are shown in FIGS. 5A and 5B, respectively. The IPA and AA values obtained for the test media containing ssDNA during decreasing temperatures are shown in FIGS. 6A and 6B, respectively.

Test media with the ssDNA concentrations of 1 pmole/500 µl and 2 pmoles/500 µl exhibited the greatest deviations from linearity of conductance as the temperature was increased from 2° C. to 80° C. (FIGS. 5A and 5B). Unexpectedly a phase of increasing resistance was clearly exhibited between 37° C. to 43° C. during increasing temperature measurements of the test media containing the lowest ssDNA concentrations. This is at variance with the teaching of the prior art. As the ssDNA concentration was increased, this decline in conductance within this temperature range was progressively eliminated such that when the test medium contained 12 pmoles/500 µl of ssDNA a return to systematic linearity of conductance was observed during increasing temperature measurements (FIG. 5). No similar divergences in linearity of conductance were observed for test media bearing low concentrations of ssDNA during decreasing temperature measurements. The decrease in amperometric flow of the test media of this experiment was primarily linear with decreasing temperature for all the ssDNA concentrations examined (FIG. 6). This example illustrates that general rules respecting duplex nucleic acid conductance cannot be applied to single stranded nucleic acids without specific observation and calibration.

Increasing the ssDNA concentration in the test medium resulted in a progressive increase in amperometric flow at any given temperature. Between 2° C. to 18° C. the increase in conductance as a function of ssDNA concentration was somewhat variable (FIGS. 5 and 6). Between 18° C. to 80° C. a direct relationship between ssDNA concentration and amperometric flow was observed (FIG. 5). Although the increase in conductance of the test media was, contrary to the prior art, not proportionate to the increase in ssDNA concentration, in that doubling the ssDNA concentration did not result in a doubling of the amperometric flow, a linear relationship was observed. This linear relationship between ssDNA concentration in the test media and IPA or AA values is shown at 70° C. in FIGS. 9A and 9B, respectively. As the test medium concentration of the ssDNA was increased, the rate of change in conductance of the test medium with increasing temperature was progressively increased (FIGS. 5A and 5B).

Four, eight, twelve, twenty and twenty-four pmoles of the 15-mer annealed dsDNA (SEQ ID NO:1) were each tested in a test medium comprising a final volume of 500 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained for the test media containing dsDNA during increasing temperatures are shown in FIGS. 7A and 7B, respectively. The IPA and AA values obtained for the test media containing dsDNA during decreasing temperatures are shown in FIGS. 8A and 8B, respectively.

Test media containing dsDNA were more conductive of electricity than were test media containing the identical concentrations of ssDNA (compare FIGS. 5 and 7). Conductance values increased with increasing temperature and declined with decreasing temperature primarily in a linear fashion. Conversion from duplex DNA to ssDNA, and vice versa, would be expected to occur at certain elevated temperatures in the absence of periodic electrification of the sample. The serial application of voltage in this experiment appears to have resulted in the originally duplex complementary nucleic acid strands remaining intact or at least in very close proximity to each other, so as to result in no interruption of the linear progression of IPA and AA values (FIGS. 7 and 8).

As the concentration of the dsDNA was increased, the test media produced an increase in the amperometric flow at all temperatures (FIGS. 7 and 8). The rate of change in conductance during temperature variation increased slightly with increasing dsDNA concentration.

The hysteretic effect observed when the IPA and AA values were compared during increasing or decreasing temperature measurements were less pronounced for the test media containing dsDNA concentrations than for those bearing comparable ssDNA concentrations (FIGS. 5–8).

Example 3

Example 3 examines the change in amperometric flow of test media containing ssDNA or dsDNA as a function of temperature when different amounts of voltage are applied. The test media (250 µl) were heated from 2° C. to 80° C. and cooled from 80° C. to 2° C., with IPA and AA readings taken at 1° C. intervals following 500 msec applications of 3, 5, 9, 18 or 27 Volts of DC voltage, as described in Example 1. The IPA and AA values obtained for ddH$_2$O alone during increasing temperatures are shown in FIGS. 10A and 10B, respectively. The IPA and AA values obtained for ddH$_2$O alone during decreasing temperatures are shown in FIGS. 1A and 1B, respectively. Minor increases in amperometric flow through ddH$_2$O were observed with increased DC voltage application.

Eight pmoles of the sense strand of SEQ ID NO:1 in the test medium made it much more responsive to change in applied voltage. The IPA and AA values produced by the test medium containing the ssDNA during increasing temperatures are shown in FIGS. 12A and 12B, respectively. The IPA and AA values produced by the test medium containing the ssDNA during decreasing temperatures are shown in FIGS. 13A and 13B, respectively.

Linearity of conductance as a function of increasing or decreasing temperature was observed for the test media containing ssDNA at every DC voltage applied, especially at the lower voltages (FIGS. 12 and 13). The hysteretic effect observed when the IPA and AA values of the test medium containing ssDNA were compared during increasing or decreasing temperature measurements were less pronounced when lower voltages were applied.

Increasing the applied voltage resulted in a progressive increase in amperometric flow of the test medium containing ssDNA at any given temperature (FIGS. 12 and 13). The increase in conductance of this test medium was however not proportionate or linear to the increase in applied voltage, contrary to certain teachings of the prior art. The IPA and AA levels of the test medium containing ssDNA, although significantly higher than those of ddH$_2$O alone, were very similar and relatively low upon the application of 3 V or 5 V. 9 V and 18 V applications to the test medium containing ssDNA resulted in significant increases in IPA and AA levels. Treatment with 27 V produced a substantial increase in IPA and AA levels. The rate of change in conductance of the test medium containing ssDNA observed at any selected temperature increased as the level of applied voltage was increased.

The change in amperometric flow of a test medium comprising 8 pmoles of the 15-mer annealed dsDNA (SEQ ID NO:1) in 250 µl ddH$_2$O was then examined as a function of temperature when different amounts of voltage were applied. The IPA and AA values obtained for the test medium containing dsDNA during increasing temperatures are shown in FIGS. 14A and 14B, respectively. The IPA and AA values obtained for the test medium containing dsDNA during decreasing temperatures are shown in FIGS. 15A and 15B, respectively.

At every DC voltage tested, the test medium containing dsDNA was more conductive of electricity than was the test medium containing comparable concentrations of ssDNA (compare FIGS. 12 and 13 with FIGS. 14 and 15). Regardless of the level of DC voltage applied, the IPA and AA values for the test medium containing dsDNA were primarily linear with increasing or decreasing temperature. Variation of IPA and AA levels obtained during increasing temperatures compared to those obtained during decreasing temperatures were apparent only at the higher voltages. Since there was no disruption of the linearity of conductance of the test medium containing dsDNA when heated from 2°

C. to 80° C. and cooled from 80° C. to 2° C., the duplex DNA either did not melt or the denatured complementary ssDNA strands appear to have remained in very close proximity to each other at every voltage application, even at 27 V, so as to sustain the electron pathway initially constituted by the dsDNA at low temperatures when the experiment began.

Progressive increases in amperometric flow of the test medium containing dsDNA were observed with the application of increasing voltage (FIGS. 14 and 15). Treatment with 3 V or 5 V resulted in relatively low IPA and AA levels of this test medium. Dramatic augmentation of conductance was observed upon application of 9 V, 18 V or 27 V to this test medium. The increase in amperometric flow of the test medium containing dsDNA was however not proportionate or linear to the increase in applied voltage. As the voltage increased, the rate of change in conductance during temperature variation increased, most noticeably at the highest voltages tested.

Example 4

Example 4 examines electron transport preferences in test media comprising different populations of related or unrelated ssDNA or dsDNA. The ssDNA and dsDNA sequences tested in Examples 1 to 3 were 15-mer in length. Example 4 also examines the effect of varied length of the ssDNA and dsDNA sequences on conductivity in the test media as a function of temperature.

Sense and antisense 50-mer ssDNA sequences, possessing a 53% GC content, were synthesized on a DNA synthesizer, purified by HPLC, annealed and diluted in ddH$_2$O to a concentration of 1 pmole/µl as described in Example 1. Sequence ID NO:2 was a 50-mer wild-type dsDNA designed to comprise a central 15 bp segment perfectly homologous to SEQ ID NO:1.

Sequence for the sense strand of the 50-mer dsDNA (SEQ ID NO:2): 5'-GAG CAC CAT GAC AGA CAC TGT CAT CTC TGG TGT GTC CTA CGA TGA CTC TG-3'.

Sequence for the antisense strand of the 50-mer dsDNA (SEQ ID NO:2): 5'-CAG AGT CAT CGT AGG ACA CAC CAG AGA TGA CAG TGT CTG TCA TGG TGC TC-3'.

Sense and antisense 15-mer ssDNA sequences, possessing a 40% GC content, were synthesized on a DNA synthesizer, purified by HPLC, annealed and diluted in ddH$_2$O to a concentration of 1 pmole/µl as described in Example 1. Sequence ID NO:3 was a 15-mer dsDNA, derived from the Drosophila erg gene, whose sequence was unrelated to SEQ ID NO:1.

Sequence for the sense strand of the 15-mer dsDNA (SEQ ID NO:3): 5'-CAG AAA GGT TTC AAG-3'.

Sequence for the antisense strand of the 15-mer dsDNA (SEQ ID NO:3): 5'-CTT GAA ACC TTT CTG-3'.

Test media comprising eight pmoles of the sense strands of the 15-mer SEQ ID NO:1 or 50-mer SEQ ID NO:2, or eight pmoles of the 15-mer dsDNA (SEQ ID NO:1) or 50-mer dsDNA (SEQ ID NO:2) were each tested in a final volume of 250 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained for the test media containing the ssDNA or dsDNA during increasing temperatures are shown in FIGS. 16A and 16B, respectively. The IPA and AA values obtained for the test media containing the ssDNA or dsDNA during decreasing temperatures are shown in FIGS. 17A and 17B, respectively.

Linearity of conductance as a function of temperature was observed for all the test media tested, irrespective of DNA sequence length. The complementary ssDNA strands of the 15-mer or 50-mer dsDNA sequences appear to have remained in duplex form or in close proximity to each other at elevated temperatures, as evidenced by the non-interruption of the linear progression of IPA and AA values in the test media (FIGS. 16 and 17). This suggests that the electron pathway established at low temperatures through the dsDNA, was maintained at high temperatures.

The test media containing dsDNA was more conductive of electricity than was the test media containing ssDNA at the same oligonucleotide length (FIGS. 16 and 17). Sequence variation in the duplex nucleic acid can produce significantly different conductance values at all temperatures (data not shown). Increasing the length of the ssDNA from a 15-mer to a 50-mer oligonucleotide resulted in approximately a 2.3-fold increase in amperometric flow values during increasing temperature measurements (FIG. 16) and a slightly greater difference in amperometric flow values during decreasing temperature measurements (FIG. 17). The difference in conductance observed between a test medium comprising 15-mer dsDNA and one comprising 50-mer dsDNA ranged from 2-fold to 3.4-fold, depending on temperature or whether measurements were taken as the temperature increased or decreased (FIGS. 16 and 17). The prior art took no account as to whether a measurement taken at a certain temperature was taken after the temperature had been raised or lowered to the testing temperature.

Eight pmoles of the sense strands of the 15-mer SEQ ID NO:1 or 50-mer SEQ ID NO:2 were each tested individually or in combination in test media having a final volume of 250 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained from the test media containing 15-mer ssDNA, 50-mer ssDNA or the mix of the parallel homologous 15-mer and 50-mer ssDNAs during increasing temperatures are shown in FIGS. 18A and 18B, respectively. The IPA and AA values obtained from the same three samples during decreasing temperatures are shown in FIGS. 19A and 19B, respectively.

Test media containing eight pmoles of the antisense strand of the 15-mer SEQ ID NO:1 or the sense strand of the 50-mer SEQ ID NO:2 were each tested individually or in combination in a final volume of 250 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained from the test media containing 15-mer ssDNA, 50-mer ssDNA or the mix of the antiparallel complementary 15-mer and 50-mer ssDNAs during increasing temperatures are shown in FIGS. 20A and 20B, respectively. The IPA and AA values obtained from the same three samples during decreasing temperatures are shown in FIGS. 21A and 21B, respectively.

The IPA and AA values for the test media containing the mix of the parallel homologous or antiparallel complementary 15-mer and 50-mer ssDNAs were slightly greater than those for the test medium containing the 50-mer ssDNA alone during increasing temperature measurements (FIGS. 18 and 20). During decreasing temperature measurements the IPA and AA values for the test media containing the mix of the parallel homologous or antiparallel complementary 15-mer and 50-mer ssDNAs were very close to those for the test medium containing the 50-mer ssDNA alone (FIGS. 19 and 21). These small increases in conductance were lower than would be expected if the conductance values of the 15-mer ssDNA and 50-mer ssDNA were simply added, and lower than would be expected for dsDNA conductance. It appears that in the presence of ssDNAs of varying length in the test medium, which have an affinity for one another, the amperometric flow preferentially depends upon electron transport through the ssDNA species of greatest length. This detectable relationship appears to hold true for ssDNA nucleic acids whose affinity for each other is based on either a homologous preference or a Watson-Crick preference.

Test media comprising eight pmoles of the antisense strand of the 15-mer SEQ ID NO:3 or the sense strand of the 50-mer SEQ ID NO:2 were each tested individually or in combination in a final volume of 250 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained from the test media containing the 15-mer ssDNA, 50-mer ssDNA or the mix of the unrelated 15-mer and 50-mer ssDNAs during increasing temperatures are shown in FIGS. 22A and 22B, respectively. The IPA and AA values obtained from the three test media during decreasing temperatures are shown in FIGS. 23A and 23B, respectively.

The presence of totally unrelated 15-mer and 50-mer ssDNA sequences in the test medium resulted in IPA and AA values significantly greater than that observed from the test medium containing the ssDNA sequence of longest length alone (i.e. the sense strand of the 50-mer SEQ ID NO:2) (FIGS. 22 and 23). In the absence of potential binding between the two ssDNA sequences, the conductance levels of the test medium containing the mixed ssDNA sequences appeared to comprise conductance levels approximating the sum of the conductance levels observed from the test media containing each individual ssDNA sequence separately. The amperometric levels achieved however were not strictly additive, especially during the increasing temperature measurements (FIGS. 22A and 22B). The rate of change in conductance for the test medium containing the mix of the unrelated 15-mer and 50-mer ssDNA sequences was the same as that for the test medium containing the 50-mer ssDNA sequence alone, during both increasing and decreasing temperature measurements (FIGS. 22 and 23), which suggests that the 15-mer ssDNA played no important role in electron transfer through that test medium containing other nucleic acids.

The conductance of test media containing an equimolar population of complementary 15-mer ssDNA and 50-mer dsDNA sequences or an equimolar population of homologous 15-mer dsDNA and 50-mer dsDNA sequences was examined next. Eight pmoles of the 50-mer dsDNA (SEQ ID NO:2) and eight pmoles of the sense strand of the 15-mer SEQ ID NO:1 or eight pmoles of the 15-mer dsDNA (SEQ ID NO:1) were each tested individually or in combination in test media having a final volume of 250 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained from the test media containing 15-mer ssDNA, 15-mer dsDNA, 50-mer dsDNA or the mix of the 15-mer ssDNA or 15-mer dsDNA with the 50-mer dsDNA during increasing temperatures are shown in FIGS. 24A and 24B, respectively. The IPA and AA values obtained from the same five test media during decreasing temperatures are shown in FIGS. 25A and 25B, respectively.

A test medium containing an equimolar population of complementary 15-mer ssDNA and 50-mer dsDNA sequences produced IPA and AA values that were nearly identical to those produced by the test medium containing 50-mer dsDNA sequences alone, during both increasing and decreasing temperature measurements (FIGS. 24 and 25). This suggested that binding between the ssDNA and dsDNA sequences had not occurred under the test conditions of the experiment. The conductance appeared substantially attributable to the longer 50-mer dsDNA as the amperometric flow values of the test medium containing the mixed population were nearly identical to those of the test medium containing the 50-mer dsDNA alone.

However a test medium containing an equimolar population of homologous 15-mer dsDNA and 50-mer dsDNA sequences unexpectedly produced IPA and AA values that were slightly greater than those observed with a test medium containing the 50-mer dsDNA sequences alone, during both increasing and decreasing temperature measurements (FIGS. 24 and 25). The increase in conductance observed in the test medium consisting of this mixed population when compared to that observed with the test medium containing the 50-mer dsDNA alone was close to the difference in conductance observed between the test media composed of the 15-mer ssDNA and the 15-mer dsDNA sequences (at least as to measurements taken during increasing temperature) (FIGS. 24 and 25). This suggests that the conductance produced by the test medium comprising the mixed population of the homologous 15-mer dsDNA sequences and the 50-mer dsDNA sequences depended upon a specific interaction by the contained 15-mer and 50-mer duplexes to augment electron transport through the test medium.

The conductance of test media containing an equimolar population of unrelated 15-mer ssDNA and 50-mer dsDNA sequences or an equimolar population of unrelated 15-mer dsDNA and 50-mer dsDNA sequences was examined next. Test media containing eight pmoles of the 50-mer dsDNA (SEQ ID NO:2) and eight pmoles of the antisense strand of the 15-mer SEQ ID NO:3 or eight pmoles of the 15-mer dsDNA (SEQ ID NO:3) were each tested individually or in combination in a final volume of 250 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained from the test media containing 15-mer ssDNA, 15-mer dsDNA, 50-mer dsDNA or the mix of the 15-mer ssDNA or 15-mer dsDNA with the unrelated 50-mer dsDNA during increasing temperatures are shown in FIGS. 26A and 26B, respectively. The IPA and AA values obtained from the same five test media during decreasing temperatures are shown in FIGS. 27A and 27B, respectively.

A test medium with an equimolar population of unrelated 15-mer ssDNA and 50-mer dsDNA sequences produced IPA and AA values that were nearly identical to those produced by the test medium composed of 50-mer dsDNA sequences alone, during both increasing and decreasing temperature measurements (FIGS. 26 and 27). In the absence of potential binding between the unrelated ssDNA and dsDNA sequences contained in the sample, the amperometric flow of the mixed population appeared to be attributable to that of the 50-mer dsDNA sequence alone.

A test medium containing an equimolar population of unrelated 15-mer dsDNA and 50-mer dsDNA sequences produced IPA and AA values that were very similar to those produced by the test medium comprising 50-mer dsDNA sequences alone, during increasing temperature measurements (FIG. 26). During decreasing temperature measurements the test medium consisting of an equimolar population of unrelated 15-mer dsDNA and 50-mer dsDNA sequences produced IPA and AA values that were marginally greater than that produced by the test medium composed of 50-mer dsDNA sequences alone (FIG. 27). These results suggest that the 50-mer dsDNA sequences were the preferred or dominant electron transport pathway within the mixed population of unrelated 15-mer dsDNA and 50-mer dsDNA sequences, despite the high level of conductance observed in the test medium comprising the 15-mer dsDNA (SEQ ID NO:3) alone (FIGS. 26 and 27). The level of conductance of the test medium consisting of the 15-mer dsDNA (SEQ ID NO:3) was unusually high in comparison to the level of conductance observed from the test medium containing the antisense strand of SEQ ID NO:3 (FIGS. 26 and 27) or with the sense strand of SEQ ID NO:3 (data not shown), and seemed to be characteristic for this particular 15-mer dsDNA sequence. The reason for the enhanced conductance of this 15-mer dsDNA sequence in the test medium is not known.

The level of conductance of the test medium comprising the sense strand of SEQ ID NO:3 was significantly lower than that of the test medium comprising the antisense strand of SEQ ID NO:3 (data not shown), despite the presence of four guanine bases in the former strand and only two guanine bases in the latter strand. This observation contradicts the view that electron transport is dependent upon or favored by guanine base content within a DNA strand, which would predict higher levels of conductance from test media containing DNA strands possessing a higher guanine content. Giese, "Charge Hopping Through DNA." Journal of Biomolecular Structure and Dynamics, Mendel-Brno edition June, 2000, and Giese et al., "Direct Observation." Nature 412, Jul. 19, 2001, p. 318.

Example 5

Example 5 examines the change in amperometric flow of various concentrations of ssDNA or dsDNA as a function of temperature when the test media was subjected to a mechanical agitation. Teflon coated stir bars, 2 mm in length and 2 mm in width, (Sigma-Aldrich, Inc., Saint Louis, Mo., USA) were placed at the bottom of the test cuvettes, which were positioned on top of a magnetic stirrer. When the magnetic stirrer (Model PC 420, manufactured by Corning and purchased from VWR Can Lab, Mississauga, ON, Canada) was set at speed 7, the stir bars spun at approximately 550 rpm. The stir bars did not come in contact with the two electrodes in the test medium.

Test media comprising one, two, four, eight, twelve, sixteen, twenty or twenty-four pmoles of the sense strand of SEQ ID NO:1 were each tested in a final volume of 500 µl ddH$_2$O. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained for the test media containing ssDNA during increasing temperatures and continuous agitation are shown in FIGS. 28A and 28B, respectively. The IPA and AA values obtained for the test media containing ssDNA during decreasing temperatures and continuous agitation are shown in FIGS. 29A and 29B, respectively.

Under conditions of continuous agitation of the test media, conductance values for the test media containing ssDNA increased with increasing temperature and declined with decreasing temperature (FIGS. 28 and 29). Turbulence caused from the constant spinning did however result in random fluctuations in linearity of conductance of the test media comprising ssDNA throughout the entire temperature ranged tested. These fluctuations in conductance were especially noticeable during decreasing temperatures where linearity of conductance was the norm in static test media containing ssDNA.

Comparison of IPA and AA values at any given temperature between identical ssDNA concentrations in static or agitated test media consistently demonstrated lower values of conductance for ssDNA present in the agitated test media (compare FIGS. 5 and 28, and FIGS. 6 and 29).

Test media with increased ssDNA concentration produced progressively increased amperometric flow. While a linear relationship between ssDNA concentration and IPA or AA values of the test media was observed in static test media (FIGS. 5, 6 and 9), this was not the case in agitated test media (FIGS. 28 and 29). Small increases in amperometric flow were produced by the test media in which the concentration of ssDNA varied from 1 pmole/500 µl to 4 pmoles/500 µl during continuous stirring. A significant increase in conductance was observed when the ssDNA concentration of the test medium was increased to 8 pmoles/500 µl during agitation. The levels of conductance of the test media comprising ssDNA concentrations of 12 pmoles/500 µl or 16 pmoles/500 µl were nearly identical during increasing temperature measurements under conditions of agitation. The levels of amperometric flow of the test media containing 8 pmoles/500 µl, 12 pmoles/500 µl and 16 pmoles/500 µl ssDNA concentrations seemed to cluster together during decreasing temperature measurements during agitation. Continuous stirring of the test media muted test media conductance as a function of increased ssDNA concentration. More discrimination between test media levels of conductance was observed when the concentration of comprised ssDNA increased from 16 pmoles/500 µl to 24 pmoles/500 µl during agitation, although random divergence in linearity of conductance was still evident.

We propose that application of low levels of voltage in bulk solution appears to organize DNA into an electron pathway between the electrodes. This electron pathway appears to persist over time in the face of Brownian motion, which increases or decreases with temperature. This organization is disrupted during continuous agitation of the test medium such that the electron flow through the test medium is facilitated to a much lesser extent by the DNA and becomes erratic. Rates of reduction in conductance caused by continuous agitation of the test medium are not identical for every incremental change in DNA concentration.

Test media comprising one, two, four, eight, twelve, sixteen, twenty or twenty-four pmoles of the 15-mer annealed dsDNA (SEQ ID NO:1) were then each tested in a final volume of 500 µl ddH$_2$O under conditions of continuous agitation as described above. The test media were heated from 2° C. to 80° C. and cooled from 80° C. to 2° C., with IPA and AA readings taken at 1° C. intervals following 500 msec applications of 9 Volts of DC voltage as described in Example 1. The IPA and AA values obtained for the test media containing dsDNA during increasing temperatures and continuous agitation are shown in FIGS. 30A and 30B, respectively. The IPA and AA values obtained for the test media containing dsDNA during decreasing temperatures and continuous agitation are shown in FIGS. 31A and 31B, respectively.

Conductance values for the test media containing dsDNA increased with increasing temperature and declined with decreasing temperature (FIGS. 30 and 31), suggesting that dsDNA was able to facilitate electron transport during continuous agitation of the test media much better than were test media containing identical concentrations of ssDNA. Random fluctuations in conductance caused by the turbulence induced by the spinning were observed. Unexpectedly and strikingly, continuous agitation of the test media did not disrupt the linearity of the amperometric flow of the test media containing the dsDNA, as the test medium approached, exceeded or retreated from 45° C., the $T_m$ of the 15-mer dsDNA. Conversion from duplex DNA to ssDNA, and vice versa, would be expected to occur in the vicinity of the $T_m$ of the duplex DNA in the absence of periodic electrification of the sample. The serial application of voltage in this experiment appears to have resulted in the duplex DNA either remaining intact in spite of the agitation and temperature increase above the $T_m$, or the separated complementary ssDNA strands remained in such close proximity to each other in the agitated test media, so as to facilitate electron transport in a manner consistent with amperometric values facilitated by the duplex DNA at lower temperatures (FIGS. 30 and 31).

Lower IPA and AA values were observed for the test media containing the dsDNA under conditions of continuous agitation than for the identical concentrations of dsDNA present in unstirred test media (compare FIGS. 7 and 30, and FIGS. 8 and 31). A progressive increase in amperometric flow of the test media was observed as the comprised dsDNA concentration was increased (FIGS. 30 and 31). This increase in conductance with increased dsDNA concentration was however not linear in the agitated test media, as it was in the unstirred test media. Clustering of conductance values as observed with test media containing certain ssDNA concentrations during agitation were not observed for test media containing comparable concentrations of dsDNA during both increasing and decreasing temperature measurements.

While the invention has been described in detail and with reference to specific examples thereof, it will be apparent to one skilled in the art that various changes and modifications can be made therein without departing from the spirit and scope thereof.

What is claimed is:

1. A method for determining an affinity of a first nucleobase-containing sequence for a second nucleobase-containing sequence, said method comprising:

providing a test medium containing said first nucleobase-containing sequence and said second nucleobase-containing sequence, wherein said first nucleobase-containing sequence and said second nucleobase-containing sequence are of different lengths;

applying a voltage across said test medium;

measuring a test electric current through said test medium; and determining said affinity by evaluating whether said test electric current is equivalent to a reference electric current of a reference medium containing a longer of said first nucleobase-containing sequence and said second nucleobase-containing sequence.

2. The method of claim 1, wherein said first nucleobase-containing sequence and said second nucleobase-containing sequence are single-stranded, and said first nucleobase-containing sequence has no affinity for said second nucleobase-containing sequence when said test electric current is more than said reference electric current.

3. The method of claim 1, wherein said first nucleobase-containing sequence and said second nucleobase-containing sequence are single-stranded, and said first nucleobase-containing sequence has affinity for said second nucleobase-containing sequence when said test electric current is equivalent to said reference electric current.

4. The method of claim 3, wherein said affinity is parallel homologous bonding, antiparallel homologous bonding, parallel complementary bonding or antiparallel complementary bonding.

5. The method of claim 3, wherein said affinity is non-bonding association.

6. The method of claim 1, wherein said first nucleobase-containing sequence and said second nucleobase-containing sequence are double-stranded, and said first nucleobase-containing sequence has no affinity for said second nucleobase-containing sequence when said test electric current is equivalent to said reference electric current.

7. The method of claim 1, wherein said first nucleobase-containing sequence and said second nucleobase-containing sequence are double-stranded, and said first nucleobase-containing sequence has affinity for said second nucleobase-containing sequence when said test electric current is more than said reference electric current.

8. The method of claim 7, wherein said affinity is parallel homologous bonding, antiparallel homologous bonding, parallel complementary bonding or antiparallel complementary bonding.

9. The method of claim 7, wherein said affinity is non-bonding association.

* * * * *